United States Patent
Horvath et al.

(10) Patent No.: US 10,470,927 B2
(45) Date of Patent: Nov. 12, 2019

(54) AB EXTERNO INTRAOCULAR SHUNT PLACEMENT

(71) Applicant: AqueSys, Inc., Aliso Viejo, CA (US)

(72) Inventors: Christopher Horvath, Mission Viejo, CA (US); Laszlo O. Romoda, San Clemente, CA (US)

(73) Assignee: AqueSys, Inc., Aliso Viejo, CA (US)

( * ) Notice: Subject to any disclaimer, the term of this patent is extended or adjusted under 35 U.S.C. 154(b) by 466 days.

(21) Appl. No.: 15/172,090

(22) Filed: Jun. 2, 2016

(65) Prior Publication Data
US 2016/0354244 A1    Dec. 8, 2016

Related U.S. Application Data

(60) Provisional application No. 62/170,338, filed on Jun. 3, 2015, provisional application No. 62/279,585, filed on Jan. 15, 2016.

(51) Int. Cl.
*A61F 9/007* (2006.01)
*A61F 9/00* (2006.01)
*A61B 17/34* (2006.01)

(52) U.S. Cl.
CPC ........ *A61F 9/00781* (2013.01); *A61F 9/0017* (2013.01); *A61B 17/3468* (2013.01); *A61B 2017/3492* (2013.01); *A61F 2009/0052* (2013.01)

(58) Field of Classification Search
CPC ............... A61F 9/0017; A61F 9/00781; A61F 2009/0052; A61B 17/3468; A61B 2017/3492
See application file for complete search history.

(56) References Cited

U.S. PATENT DOCUMENTS

| | | |
|---|---|---|
| 3,788,327 A | 1/1974 | Donowitz et al. |
| 3,960,150 A | 6/1976 | Hussain et al. |
| 4,090,530 A | 5/1978 | Lange |
| 4,402,308 A | 9/1983 | Scott |
| 4,562,463 A | 12/1985 | Lipton |
| 4,583,117 A | 4/1986 | Lipton et al. |
| 4,700,692 A | 10/1987 | Baumgartner |

(Continued)

FOREIGN PATENT DOCUMENTS

| | | |
|---|---|---|
| CN | 201668585 U | 12/2010 |
| GB | 2 296 663 A | 7/1996 |

(Continued)

OTHER PUBLICATIONS

Coran, (editor in chief), "Pediatric Surgery," Elsevier Saunders, published Feb. 14, 2012, 7th Edition, vol. 1, Chapter 128, pp. 1673-1697.

(Continued)

*Primary Examiner* — George J Ulsh
(74) *Attorney, Agent, or Firm* — Nathan S. Smith; Danny Mansour; Morgan, Lewis & Bockius LLP

(57) ABSTRACT

Placing an intraocular shunt ab externo into an eye can include inserting the shunt into the eye and either before and/or after insertion, ballooning a target outflow region of the eye to permit an outflow end of the shunt to be enveloped within the ballooned target outflow region. An injector docking device can optionally be used to guide insertion of the needle and shunt into the eye.

18 Claims, 34 Drawing Sheets

(56) References Cited

U.S. PATENT DOCUMENTS

| | | |
|---|---|---|
| 4,722,724 A | 2/1988 | Schocket |
| 4,744,362 A | 5/1988 | Grundler |
| 4,750,901 A | 6/1988 | Molteno |
| 4,787,885 A | 11/1988 | Binder |
| 4,804,382 A | 2/1989 | Turina et al. |
| 4,820,626 A | 4/1989 | Williams et al. |
| 4,826,478 A | 5/1989 | Schocket |
| 4,836,201 A | 6/1989 | Patton et al. |
| 4,848,340 A | 7/1989 | Bille et al. |
| 4,863,457 A | 9/1989 | Lee |
| 4,902,292 A | 2/1990 | Joseph |
| 4,911,161 A | 3/1990 | Schechter |
| 4,915,684 A | 4/1990 | MacKeen et al. |
| 4,934,363 A | 6/1990 | Smith et al. |
| 4,936,825 A | 6/1990 | Ungerleider |
| 4,946,436 A | 8/1990 | Smith |
| 4,968,296 A | 11/1990 | Ritch et al. |
| 4,978,352 A | 12/1990 | Fedorov et al. |
| 5,041,081 A | 8/1991 | Odrich |
| 5,057,098 A | 10/1991 | Zelman |
| 5,071,408 A | 12/1991 | Ahmed |
| 5,092,837 A | 3/1992 | Ritch et al. |
| 5,098,426 A | 3/1992 | Sklar et al. |
| 5,098,443 A | 3/1992 | Parel et al. |
| 5,162,641 A | 11/1992 | Fountain |
| 5,178,604 A | 1/1993 | Baerveldt et al. |
| 5,180,362 A | 1/1993 | Worst |
| 5,201,750 A | 4/1993 | Hocherl et al. |
| 5,207,660 A | 5/1993 | Lincoff |
| 5,275,622 A | 1/1994 | Lazarus |
| 5,290,295 A | 3/1994 | Querals et al. |
| 5,300,020 A | 4/1994 | L'Esperance, Jr. |
| 5,333,619 A | 8/1994 | Burgio |
| 5,338,291 A | 8/1994 | Speckman et al. |
| 5,342,370 A | 8/1994 | Simon et al. |
| 5,360,339 A | 11/1994 | Rosenberg |
| 5,368,015 A | 11/1994 | Wilk |
| 5,370,607 A | 12/1994 | Memmen |
| 5,399,951 A | 3/1995 | Lavallee et al. |
| 5,410,638 A | 4/1995 | Colgate et al. |
| 5,443,505 A | 8/1995 | Wong et al. |
| 5,472,439 A | 12/1995 | Hurd |
| 5,476,445 A | 12/1995 | Baerveldt et al. |
| 5,516,522 A | 5/1996 | Peyman et al. |
| 5,520,631 A | 5/1996 | Nordquist et al. |
| 5,558,629 A | 9/1996 | Baerveldt et al. |
| 5,558,630 A | 9/1996 | Fisher |
| 5,573,544 A | 11/1996 | Simon et al. |
| 5,601,094 A | 2/1997 | Reiss |
| 5,651,782 A | 7/1997 | Simon et al. |
| 5,656,026 A | 8/1997 | Joseph |
| 5,665,093 A | 9/1997 | Atkins et al. |
| 5,665,114 A | 9/1997 | Weadock et al. |
| 5,670,161 A | 9/1997 | Healy et al. |
| 5,676,679 A | 10/1997 | Simon et al. |
| 5,688,562 A | 11/1997 | Hsiung |
| 5,695,474 A | 12/1997 | Daugherty |
| 5,702,414 A | 12/1997 | Richter et al. |
| 5,704,907 A | 1/1998 | Nordquist et al. |
| 5,707,376 A | 1/1998 | Kavteladze et al. |
| 5,722,948 A | 3/1998 | Gross |
| 5,763,491 A | 6/1998 | Brandt et al. |
| 5,824,072 A | 10/1998 | Wong |
| 5,868,697 A | 2/1999 | Richter et al. |
| 5,908,449 A | 6/1999 | Bruchman et al. |
| 5,932,299 A | 8/1999 | Katoot |
| 5,938,583 A | 8/1999 | Grimm |
| 5,964,747 A | 10/1999 | Eaton et al. |
| 5,968,058 A | 10/1999 | Richter et al. |
| 6,007,511 A | 12/1999 | Prywes |
| 6,007,578 A | 12/1999 | Schachar |
| 6,050,970 A | 4/2000 | Baerveldt |
| 6,086,543 A | 7/2000 | Anderson et al. |
| 6,102,045 A | 8/2000 | Nordquist et al. |
| 6,146,366 A | 11/2000 | Schachar |
| 6,159,218 A | 12/2000 | Aramant et al. |
| 6,165,210 A | 12/2000 | Lau et al. |
| 6,203,513 B1 | 3/2001 | Yaron et al. |
| 6,228,023 B1 | 5/2001 | Zaslavsky et al. |
| 6,228,873 B1 | 5/2001 | Brandt et al. |
| 6,261,256 B1 | 7/2001 | Ahmed |
| 6,264,665 B1 | 7/2001 | Yu et al. |
| 6,280,468 B1 | 8/2001 | Schachar |
| 6,309,374 B1 * | 10/2001 | Hecker .............. A61F 9/007 604/117 |
| 6,413,540 B1 | 7/2002 | Yaacobi |
| 6,450,937 B1 | 9/2002 | Mercereau et al. |
| 6,468,283 B1 | 10/2002 | Richter et al. |
| 6,471,666 B1 | 10/2002 | Odrich |
| 6,483,930 B1 | 11/2002 | Musgrave et al. |
| 6,510,600 B2 | 1/2003 | Yaron et al. |
| 6,514,238 B1 | 2/2003 | Hughes |
| 6,524,275 B1 | 2/2003 | Lynch et al. |
| 6,533,768 B1 | 3/2003 | Hill |
| 6,544,249 B1 | 4/2003 | Yu et al. |
| 6,558,342 B1 | 5/2003 | Yaron et al. |
| 6,595,945 B2 | 7/2003 | Brown |
| 6,638,239 B1 | 10/2003 | Bergheim et al. |
| 6,699,210 B2 | 3/2004 | Williams et al. |
| 6,726,664 B2 | 4/2004 | Yaron et al. |
| D490,152 S | 5/2004 | Myall et al. |
| 6,736,791 B1 | 5/2004 | Tu et al. |
| 6,752,753 B1 | 6/2004 | Hoskins et al. |
| 6,780,164 B2 | 8/2004 | Bergheim et al. |
| 6,881,198 B2 | 4/2005 | Brown |
| 6,936,053 B1 | 8/2005 | Weiss |
| 6,939,298 B2 | 9/2005 | Brown et al. |
| 6,955,656 B2 | 10/2005 | Bergheim et al. |
| 7,008,396 B1 | 3/2006 | Straub |
| 7,037,335 B2 | 5/2006 | Freeman et al. |
| 7,041,077 B2 | 5/2006 | Shields |
| 7,094,225 B2 | 8/2006 | Tu et al. |
| 7,118,547 B2 | 10/2006 | Dahan |
| 7,135,009 B2 | 11/2006 | Tu et al. |
| 7,163,543 B2 | 1/2007 | Smedley et al. |
| 7,186,232 B1 | 3/2007 | Smedley et al. |
| 7,207,980 B2 | 4/2007 | Christian et al. |
| 7,273,475 B2 | 9/2007 | Tu et al. |
| 7,291,125 B2 | 11/2007 | Coroneo |
| 7,297,130 B2 | 11/2007 | Bergheim et al. |
| 7,331,984 B2 | 2/2008 | Tu et al. |
| 7,431,709 B2 | 10/2008 | Pinchuk et al. |
| 7,431,710 B2 | 10/2008 | Tu et al. |
| 7,458,953 B2 | 12/2008 | Peyman |
| 7,481,816 B2 | 1/2009 | Richter et al. |
| 7,488,303 B1 | 2/2009 | Haffner et al. |
| 7,563,241 B2 | 7/2009 | Tu et al. |
| 7,594,899 B2 | 9/2009 | Pinchuk et al. |
| 7,625,384 B2 | 12/2009 | Eriksson et al. |
| 7,670,310 B2 | 3/2010 | Yaron et al. |
| 7,708,711 B2 | 5/2010 | Tu et al. |
| 7,722,549 B2 | 5/2010 | Nakao |
| 7,815,592 B2 | 10/2010 | Coroneo |
| 7,824,372 B1 | 11/2010 | Kurup |
| 7,837,644 B2 | 11/2010 | Pinchuk et al. |
| 7,850,638 B2 | 12/2010 | Coroneo |
| 7,857,782 B2 | 12/2010 | Tu et al. |
| 7,867,186 B2 | 1/2011 | Haffner et al. |
| 7,867,205 B2 | 1/2011 | Bergheim et al. |
| 7,879,001 B2 | 2/2011 | Haffner et al. |
| 7,879,079 B2 | 2/2011 | Tu et al. |
| 7,892,282 B2 | 2/2011 | Shepherd |
| 7,951,155 B2 | 5/2011 | Smedley et al. |
| 8,007,459 B2 | 8/2011 | Haffner et al. |
| 8,062,244 B2 | 11/2011 | Tu et al. |
| 8,075,511 B2 | 12/2011 | Tu et al. |
| 8,109,896 B2 | 2/2012 | Nissan et al. |
| 8,118,768 B2 | 2/2012 | Tu et al. |
| 8,128,588 B2 | 3/2012 | Coroneo |
| 8,167,939 B2 | 5/2012 | Silvestrini et al. |
| 8,172,899 B2 | 5/2012 | Silvestrini et al. |
| 8,262,726 B2 | 9/2012 | Silvestrini et al. |
| 8,267,882 B2 | 9/2012 | Euteneuer et al. |
| 8,273,050 B2 | 9/2012 | Bergheim et al. |

(56) References Cited

U.S. PATENT DOCUMENTS

| | | |
|---|---|---|
| 8,277,437 B2 | 10/2012 | Saal et al. |
| 8,308,701 B2 | 11/2012 | Horvath et al. |
| 8,313,454 B2 | 11/2012 | Yaron et al. |
| 8,333,742 B2 | 12/2012 | Bergheim et al. |
| 8,337,393 B2 | 12/2012 | Silverstrini et al. |
| 8,337,445 B2 | 12/2012 | Tu et al. |
| 8,337,509 B2 | 12/2012 | Schieber et al. |
| 8,348,877 B2 | 1/2013 | Tu et al. |
| 8,377,122 B2 | 2/2013 | Silvestrini et al. |
| 8,425,449 B2 | 4/2013 | Wardle et al. |
| 8,444,589 B2 | 5/2013 | Silvestrini |
| 8,460,242 B2 | 6/2013 | Paques et al. |
| 8,486,000 B2 | 7/2013 | Coroneo |
| 8,486,086 B2 | 7/2013 | Yaron et al. |
| 8,506,515 B2 | 8/2013 | Burns et al. |
| 8,512,404 B2 | 8/2013 | Frion et al. |
| 8,529,492 B2 | 9/2013 | Clauson et al. |
| 8,529,494 B2 | 9/2013 | Euteneuer et al. |
| 8,535,333 B2 | 9/2013 | de Juan, Jr. et al. |
| 8,545,430 B2 | 10/2013 | Silvestrini |
| 8,551,166 B2 | 10/2013 | Schieber et al. |
| 8,574,294 B2 | 11/2013 | Silvestrini et al. |
| 8,579,846 B2 | 11/2013 | Tu et al. |
| 8,585,629 B2 | 11/2013 | Grabner et al. |
| 8,663,303 B2 | 3/2014 | Horvath et al. |
| 8,721,702 B2 | 5/2014 | Romoda et al. |
| 8,758,290 B2 | 6/2014 | Horvath et al. |
| 8,765,210 B2 | 7/2014 | Romoda et al. |
| 8,801,766 B2 | 8/2014 | Reitsamer et al. |
| 8,828,070 B2 | 9/2014 | Romoda et al. |
| 8,852,136 B2 | 10/2014 | Horvath et al. |
| 8,852,137 B2 | 10/2014 | Horvath et al. |
| 8,852,256 B2 | 10/2014 | Horvath et al. |
| 8,974,511 B2 | 3/2015 | Horvath et al. |
| 9,017,276 B2 | 4/2015 | Horvath et al. |
| 9,044,301 B1 | 6/2015 | Pinchuk et al. |
| 9,095,411 B2 | 8/2015 | Horvath et al. |
| 9,095,413 B2 | 8/2015 | Romoda et al. |
| 9,192,516 B2 | 11/2015 | Horvath et al. |
| 9,271,869 B2 | 3/2016 | Horvath et al. |
| 9,283,116 B2 | 3/2016 | Romoda et al. |
| 9,326,891 B2 | 5/2016 | Horvath et al. |
| 9,393,153 B2 | 7/2016 | Horvath |
| 2001/0025150 A1 | 9/2001 | de Juan et al. |
| 2001/0056254 A1 | 12/2001 | Cragg et al. |
| 2002/0099434 A1 | 7/2002 | Buscemi et al. |
| 2002/0133168 A1 | 9/2002 | Smedley et al. |
| 2002/0177856 A1 | 11/2002 | Richter et al. |
| 2002/0193725 A1 | 12/2002 | Odrich |
| 2003/0015203 A1 | 1/2003 | Makower et al. |
| 2003/0050574 A1 | 3/2003 | Krueger |
| 2003/0060752 A1 | 3/2003 | Bergheim et al. |
| 2003/0060763 A1 | 3/2003 | Penfold et al. |
| 2003/0079329 A1 | 5/2003 | Yaron et al. |
| 2003/0093084 A1 | 5/2003 | Nissan et al. |
| 2003/0097053 A1 | 5/2003 | Itoh |
| 2003/0181848 A1 | 9/2003 | Bergheim et al. |
| 2003/0187383 A1 | 10/2003 | Weber et al. |
| 2003/0187384 A1 | 10/2003 | Bergheim et al. |
| 2003/0236483 A1 | 12/2003 | Ren |
| 2003/0236484 A1 | 12/2003 | Lynch et al. |
| 2004/0077987 A1 | 4/2004 | Rapacki et al. |
| 2004/0147870 A1 | 7/2004 | Burns et al. |
| 2004/0199130 A1 | 10/2004 | Chornenky et al. |
| 2004/0210185 A1 | 10/2004 | Tu et al. |
| 2004/0210209 A1 | 10/2004 | Yeung et al. |
| 2004/0215133 A1 | 10/2004 | Weber et al. |
| 2004/0216749 A1 | 11/2004 | Tu |
| 2004/0236343 A1 | 11/2004 | Taylor et al. |
| 2004/0254519 A1 | 12/2004 | Tu et al. |
| 2004/0254520 A1 | 12/2004 | Porteous et al. |
| 2004/0254521 A1 | 12/2004 | Simon |
| 2004/0260227 A1 | 12/2004 | Lisk et al. |
| 2005/0049578 A1 | 3/2005 | Tu et al. |
| 2005/0101967 A1 | 5/2005 | Weber et al. |
| 2005/0143363 A1 | 6/2005 | De Juan et al. |
| 2005/0209549 A1 | 9/2005 | Bergheim et al. |
| 2005/0246023 A1 | 11/2005 | Yeung |
| 2005/0267398 A1 | 12/2005 | Protopsaltis et al. |
| 2005/0271704 A1 | 12/2005 | Tu et al. |
| 2005/0277864 A1 | 12/2005 | Haffner et al. |
| 2006/0052721 A1 | 3/2006 | Dunker et al. |
| 2006/0064112 A1 | 3/2006 | Perez |
| 2006/0074375 A1 | 4/2006 | Bergheim et al. |
| 2006/0084907 A1 | 4/2006 | Bergheim et al. |
| 2006/0089607 A1 | 4/2006 | Chen |
| 2006/0106370 A1 | 5/2006 | Baerveldt et al. |
| 2006/0116625 A1 | 6/2006 | Renati et al. |
| 2006/0149194 A1 | 7/2006 | Conston et al. |
| 2006/0155238 A1 | 7/2006 | Shields |
| 2006/0155300 A1 | 7/2006 | Stamper et al. |
| 2006/0173397 A1 | 8/2006 | Tu et al. |
| 2006/0173446 A1 | 8/2006 | Dacquay et al. |
| 2006/0195055 A1 | 8/2006 | Bergheim et al. |
| 2006/0195056 A1 | 8/2006 | Bergheim et al. |
| 2006/0200113 A1 | 9/2006 | Haffner et al. |
| 2006/0241411 A1 | 10/2006 | Field et al. |
| 2006/0241749 A1 | 10/2006 | Tu et al. |
| 2007/0005016 A1 | 1/2007 | Williams |
| 2007/0027537 A1 | 2/2007 | Castillejos |
| 2007/0093783 A1 | 4/2007 | Kugler et al. |
| 2007/0118065 A1 | 5/2007 | Pinchuk et al. |
| 2007/0141116 A1 | 6/2007 | Pinchuk et al. |
| 2007/0172903 A1 | 7/2007 | Toner et al. |
| 2007/0191863 A1 | 8/2007 | De Juan et al. |
| 2007/0202186 A1 | 8/2007 | Yamamoto et al. |
| 2007/0263172 A1 | 11/2007 | Mura |
| 2007/0276316 A1 | 11/2007 | Haffner et al. |
| 2007/0282244 A1 | 12/2007 | Tu et al. |
| 2007/0282245 A1 | 12/2007 | Tu et al. |
| 2007/0293872 A1 | 12/2007 | Peyman |
| 2008/0015633 A1 | 1/2008 | Abbott et al. |
| 2008/0045878 A1 | 2/2008 | Bergheim et al. |
| 2008/0057106 A1 | 3/2008 | Erickson et al. |
| 2008/0108933 A1 | 5/2008 | Yu et al. |
| 2008/0147001 A1 | 6/2008 | Al-Marashi et al. |
| 2008/0181929 A1 | 7/2008 | Robinson et al. |
| 2008/0183121 A2 | 7/2008 | Smedley et al. |
| 2008/0249467 A1 | 10/2008 | Burnett et al. |
| 2008/0281277 A1 | 11/2008 | Thyzel |
| 2008/0312661 A1 | 12/2008 | Downer et al. |
| 2009/0036818 A1 | 2/2009 | Grahn et al. |
| 2009/0043321 A1 | 2/2009 | Conston et al. |
| 2009/0124973 A1 | 5/2009 | D'Agostino et al. |
| 2009/0137983 A1 | 5/2009 | Bergheim et al. |
| 2009/0138081 A1 | 5/2009 | Bergheim et al. |
| 2009/0182421 A1 | 7/2009 | Silvestrini et al. |
| 2009/0209910 A1 | 8/2009 | Kugler et al. |
| 2009/0216106 A1 | 8/2009 | Takii |
| 2009/0264813 A1 | 10/2009 | Chang |
| 2009/0270890 A1 | 10/2009 | Robinson et al. |
| 2009/0281520 A1 | 11/2009 | Highley et al. |
| 2009/0287136 A1 | 11/2009 | Castillejos |
| 2010/0004581 A1 | 1/2010 | Brigatti et al. |
| 2010/0010416 A1 | 1/2010 | Juan, Jr. et al. |
| 2010/0063478 A1 | 3/2010 | Selkee |
| 2010/0098772 A1 | 4/2010 | Robinson et al. |
| 2010/0100104 A1 | 4/2010 | Yu et al. |
| 2010/0119696 A1 | 5/2010 | Yu et al. |
| 2010/0121248 A1 | 5/2010 | Yu et al. |
| 2010/0121249 A1 | 5/2010 | Yu et al. |
| 2010/0134759 A1 | 6/2010 | Silvestrini et al. |
| 2010/0137981 A1 | 6/2010 | Silvestrini et al. |
| 2010/0173866 A1 | 7/2010 | Hee et al. |
| 2010/0185138 A1 | 7/2010 | Yaron et al. |
| 2010/0191103 A1 | 7/2010 | Stamper et al. |
| 2010/0191224 A1 | 7/2010 | Butcher |
| 2010/0241102 A1* | 9/2010 | Ma ............... A61F 9/0017 604/506 |
| 2010/0249691 A1 | 9/2010 | Van Der Mooren et al. |
| 2010/0274259 A1 | 10/2010 | Yaron et al. |
| 2010/0328606 A1 | 12/2010 | Peyman |
| 2011/0009874 A1 | 1/2011 | Wardle et al. |
| 2011/0028883 A1 | 2/2011 | Juan, Jr. et al. |

(56) References Cited

U.S. PATENT DOCUMENTS

| | | |
|---|---|---|
| 2011/0028884 A1 | 2/2011 | Coroneo |
| 2011/0046536 A1 | 2/2011 | Stegmann et al. |
| 2011/0087149 A1 | 4/2011 | Coroneo |
| 2011/0087150 A1 | 4/2011 | Coroneo |
| 2011/0087151 A1 | 4/2011 | Coroneo |
| 2011/0092878 A1 | 4/2011 | Tu et al. |
| 2011/0098627 A1 | 4/2011 | Wilcox |
| 2011/0098629 A1 | 4/2011 | Juan, Jr. et al. |
| 2011/0105987 A1 | 5/2011 | Bergheim et al. |
| 2011/0105990 A1 | 5/2011 | Silvestrini |
| 2011/0118745 A1 | 5/2011 | Yu et al. |
| 2011/0118835 A1 | 5/2011 | Silvestrini et al. |
| 2011/0230890 A1 | 9/2011 | Thyzel |
| 2011/0234976 A1 | 9/2011 | Kocaoglu et al. |
| 2011/0306915 A1 | 12/2011 | de Juan, Jr. et al. |
| 2012/0078158 A1 | 3/2012 | Haffner et al. |
| 2012/0109040 A1 | 5/2012 | Smedley et al. |
| 2012/0123315 A1 | 5/2012 | Horvath et al. |
| 2012/0123316 A1 | 5/2012 | Horvath et al. |
| 2012/0123317 A1 | 5/2012 | Horvath et al. |
| 2012/0123430 A1 | 5/2012 | Horvath et al. |
| 2012/0123433 A1 | 5/2012 | Horvath et al. |
| 2012/0123434 A1 | 5/2012 | Grabner et al. |
| 2012/0123435 A1 | 5/2012 | Romoda et al. |
| 2012/0123436 A1 | 5/2012 | Reitsamer et al. |
| 2012/0123437 A1 | 5/2012 | Horvath et al. |
| 2012/0123438 A1 | 5/2012 | Horvath et al. |
| 2012/0123439 A1 | 5/2012 | Romoda et al. |
| 2012/0123440 A1 | 5/2012 | Horvath et al. |
| 2012/0165720 A1 | 6/2012 | Horvath et al. |
| 2012/0165721 A1 | 6/2012 | Grabner et al. |
| 2012/0165722 A1 | 6/2012 | Horvath et al. |
| 2012/0165723 A1 | 6/2012 | Horvath et al. |
| 2012/0165933 A1 | 6/2012 | Haffner et al. |
| 2012/0197175 A1 | 8/2012 | Horvath et al. |
| 2012/0220917 A1 | 8/2012 | Silvestrini et al. |
| 2012/0226150 A1 | 9/2012 | Balicki et al. |
| 2012/0253258 A1 | 10/2012 | Tu et al. |
| 2012/0310137 A1 | 12/2012 | Silvestrini |
| 2013/0006164 A1 | 1/2013 | Yaron et al. |
| 2013/0018295 A1 | 1/2013 | Haffner et al. |
| 2013/0018296 A1 | 1/2013 | Bergheim et al. |
| 2013/0110125 A1 | 5/2013 | Silvestrini et al. |
| 2013/0149429 A1 | 6/2013 | Romoda et al. |
| 2013/0150770 A1 | 6/2013 | Horvath et al. |
| 2013/0158462 A1 | 6/2013 | Wardle et al. |
| 2013/0184631 A1 | 7/2013 | Pinchuk |
| 2013/0231603 A1 | 9/2013 | Wardle et al. |
| 2013/0245532 A1 | 9/2013 | Tu |
| 2013/0245573 A1 | 9/2013 | de Juan, Jr. et al. |
| 2013/0253404 A1 | 9/2013 | Tu |
| 2013/0253405 A1 | 9/2013 | Tu |
| 2013/0253406 A1 | 9/2013 | Horvath et al. |
| 2013/0253528 A1 | 9/2013 | Haffner et al. |
| 2013/0267887 A1 | 10/2013 | Kahook et al. |
| 2013/0281817 A1 | 10/2013 | Schaller et al. |
| 2013/0281908 A1 | 10/2013 | Schaller et al. |
| 2013/0281910 A1 | 10/2013 | Tu |
| 2013/0310930 A1 | 11/2013 | Tu et al. |
| 2014/0018720 A1 | 1/2014 | Horvath et al. |
| 2014/0066833 A1 | 3/2014 | Yaron et al. |
| 2014/0081195 A1 | 3/2014 | Clauson et al. |
| 2014/0135916 A1 | 5/2014 | Clauson et al. |
| 2014/0180189 A1 | 6/2014 | Horvath et al. |
| 2014/0213958 A1 | 7/2014 | Clauson et al. |
| 2014/0236065 A1 | 8/2014 | Romoda et al. |
| 2014/0236066 A1 | 8/2014 | Horvath et al. |
| 2014/0236067 A1 | 8/2014 | Horvath et al. |
| 2014/0243730 A1 | 8/2014 | Horvath |
| 2014/0272102 A1 | 9/2014 | Romoda et al. |
| 2014/0275923 A1 | 9/2014 | Haffner et al. |
| 2014/0276332 A1 | 9/2014 | Crimaldi et al. |
| 2014/0277349 A1 | 9/2014 | Vad |
| 2014/0287077 A1 | 9/2014 | Romoda et al. |
| 2014/0303544 A1 | 10/2014 | Haffner et al. |
| 2014/0323995 A1 | 10/2014 | Clauson et al. |
| 2014/0343476 A1 | 11/2014 | Penhasi |
| 2014/0371651 A1 | 12/2014 | Pinchuk |
| 2015/0005689 A1 | 1/2015 | Horvath et al. |
| 2015/0011926 A1 | 1/2015 | Reitsamer et al. |
| 2015/0038893 A1 | 2/2015 | Haffner et al. |
| 2015/0045714 A1 | 2/2015 | Horvath et al. |
| 2015/0057591 A1 | 2/2015 | Horvath et al. |
| 2015/0133946 A1 | 5/2015 | Horvath et al. |
| 2015/0148729 A1 | 5/2015 | Pinchuck et al. |
| 2015/0238687 A1 | 8/2015 | Novakovic et al. |
| 2015/0290035 A1 | 10/2015 | Horvath et al. |
| 2015/0374545 A1 | 12/2015 | Horvath et al. |
| 2016/0135993 A1 | 5/2016 | Horvath et al. |
| 2016/0135994 A1 | 5/2016 | Romoda et al. |
| 2016/0158063 A1 | 6/2016 | Romoda et al. |
| 2016/0250071 A1 | 9/2016 | Horvath et al. |
| 2016/0256317 A1 | 9/2016 | Horvath et al. |
| 2016/0256318 A1 | 9/2016 | Horvath et al. |
| 2016/0256319 A1 | 9/2016 | Horvath et al. |
| 2016/0256320 A1 | 9/2016 | Horvath et al. |
| 2016/0256323 A1 | 9/2016 | Horvath et al. |
| 2016/0278982 A1 | 9/2016 | Horvath et al. |
| 2016/0354244 A1 | 12/2016 | Horvath et al. |
| 2016/0354245 A1 | 12/2016 | Horvath et al. |
| 2017/0172797 A1 | 6/2017 | Horvath et al. |
| 2017/0172798 A1 | 6/2017 | Horvath et al. |
| 2017/0172799 A1 | 6/2017 | Horvath |
| 2017/0348150 A1 | 12/2017 | Horvath et al. |

FOREIGN PATENT DOCUMENTS

| | | |
|---|---|---|
| JP | 2009-542370 A | 12/2009 |
| JP | 2014-100576 | 5/2014 |
| RU | 2313315 C2 | 12/2007 |
| WO | WO-98/23237 A1 | 6/1998 |
| WO | WO-2000/056255 | 9/2000 |
| WO | WO-2002/74052 A2 | 9/2002 |
| WO | WO-2007/087061 A2 | 8/2007 |
| WO | WO-2008/005873 A2 | 1/2008 |
| WO | WO 2011/155922 | 12/2011 |
| WO | WO 2016/159999 | 10/2016 |
| WO | WO 2016/196841 | 12/2016 |

OTHER PUBLICATIONS

Quere, "Fluid Coating on a Fiber," Annu. Rev. Fluid Mech. 1999, 31:347-84.

Horvath, U.S. Appl. No. 15/703,802, "Intraocular Shunt Implantation," filed Sep. 13, 2017.

Horvath, U.S. Appl. No. 15/807,503, "Manually Adjustable Intraocular Flow Regulation," filed Nov. 8, 2017.

Moster et al., "Glaucoma Filtration Device: A More Standardized Surgical Experience," Ophthalmology Times, Apr. 1, 2012, pp. 1-12.

\* cited by examiner

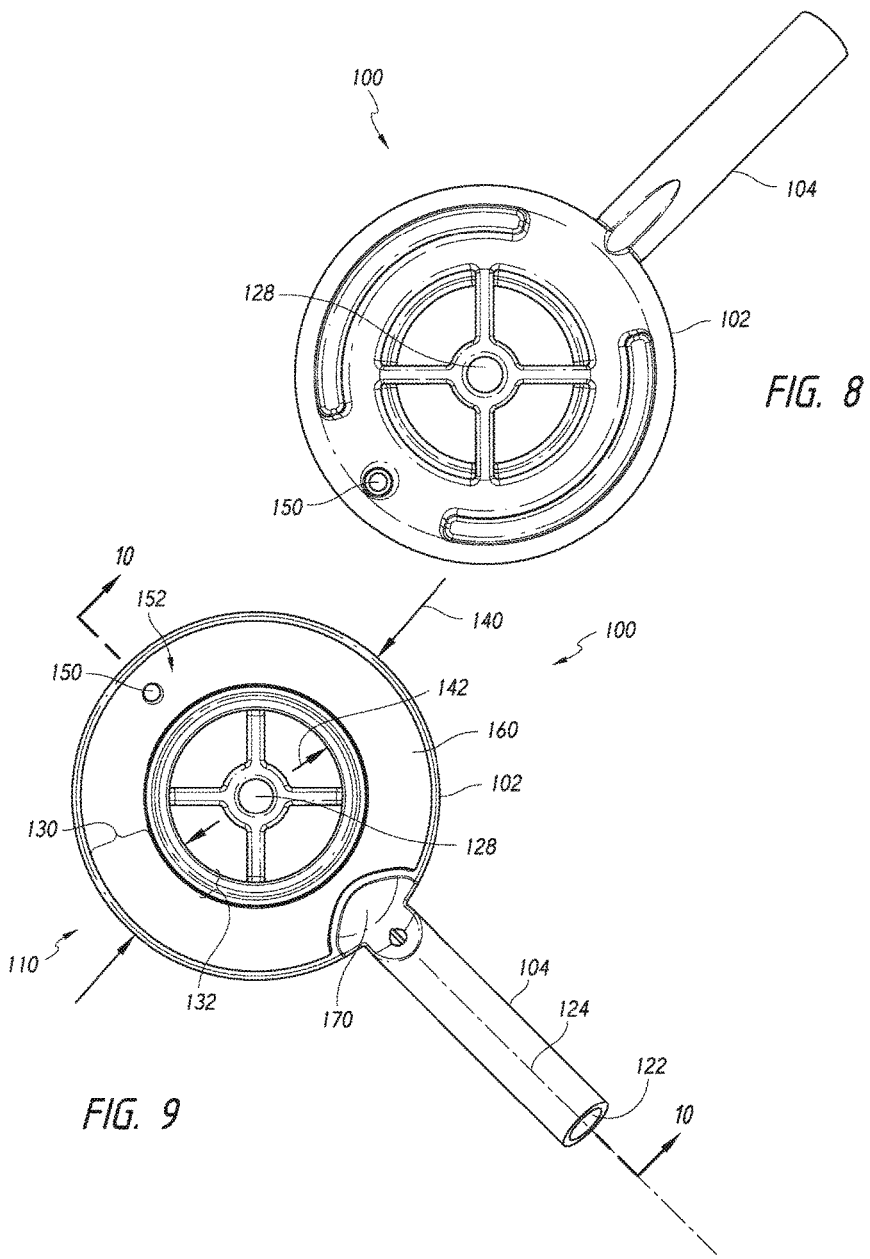

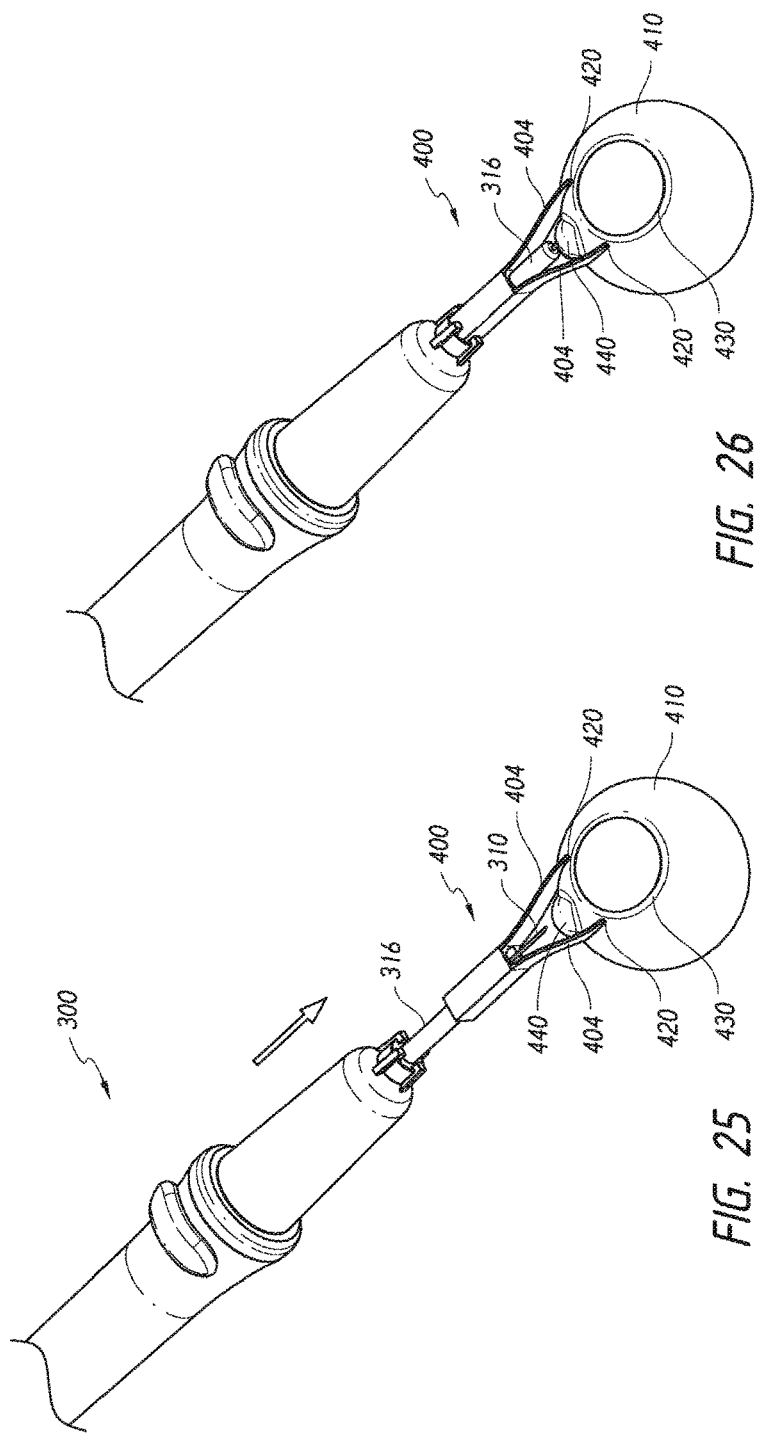

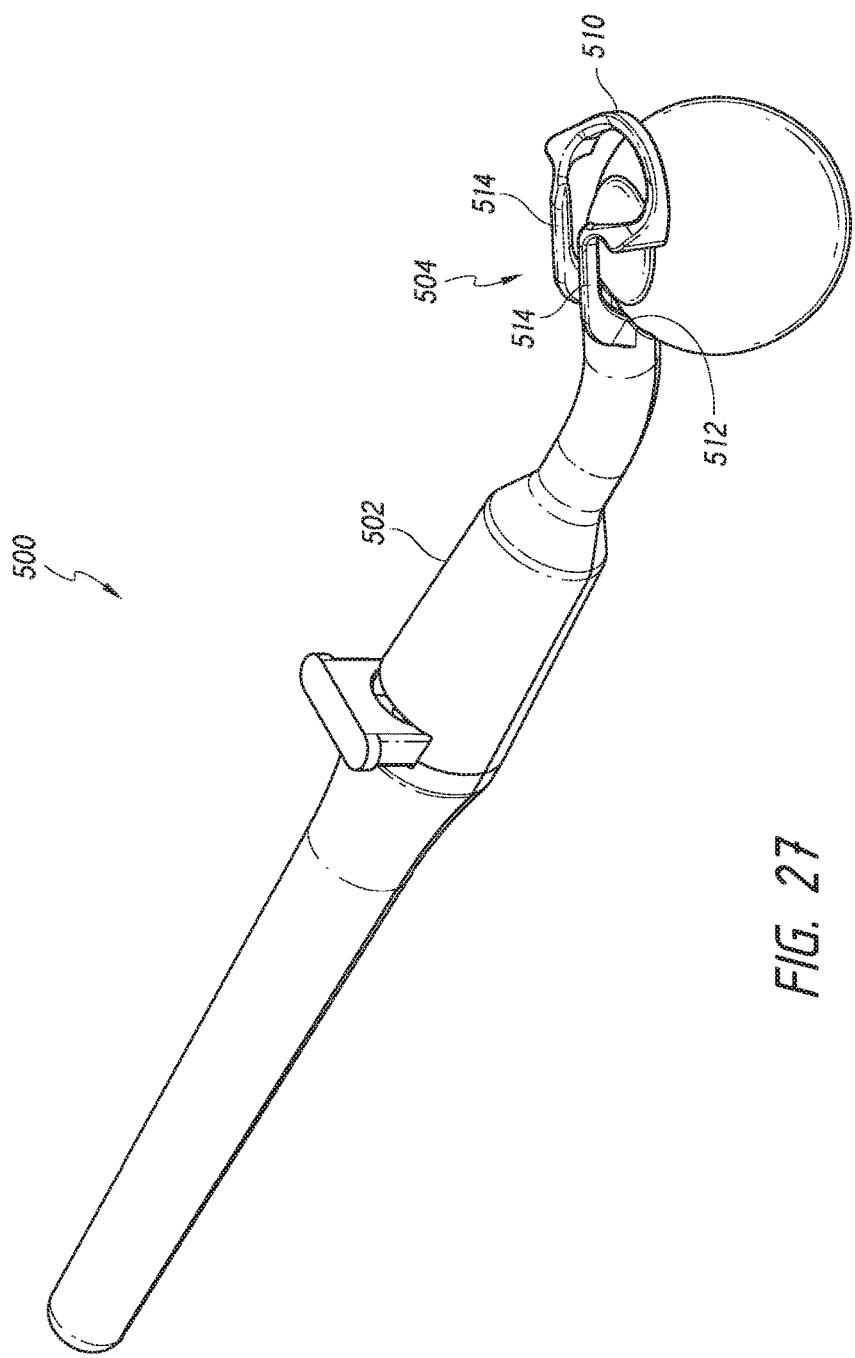

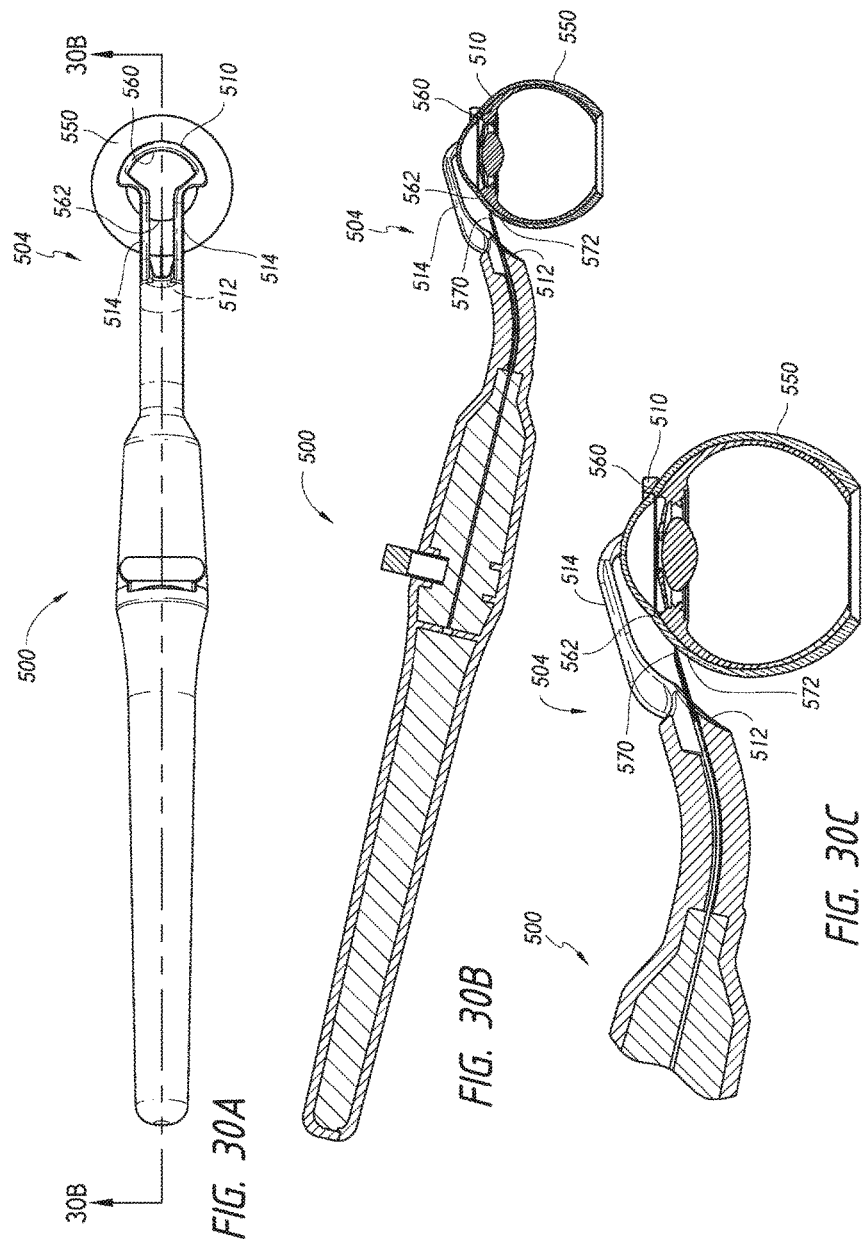

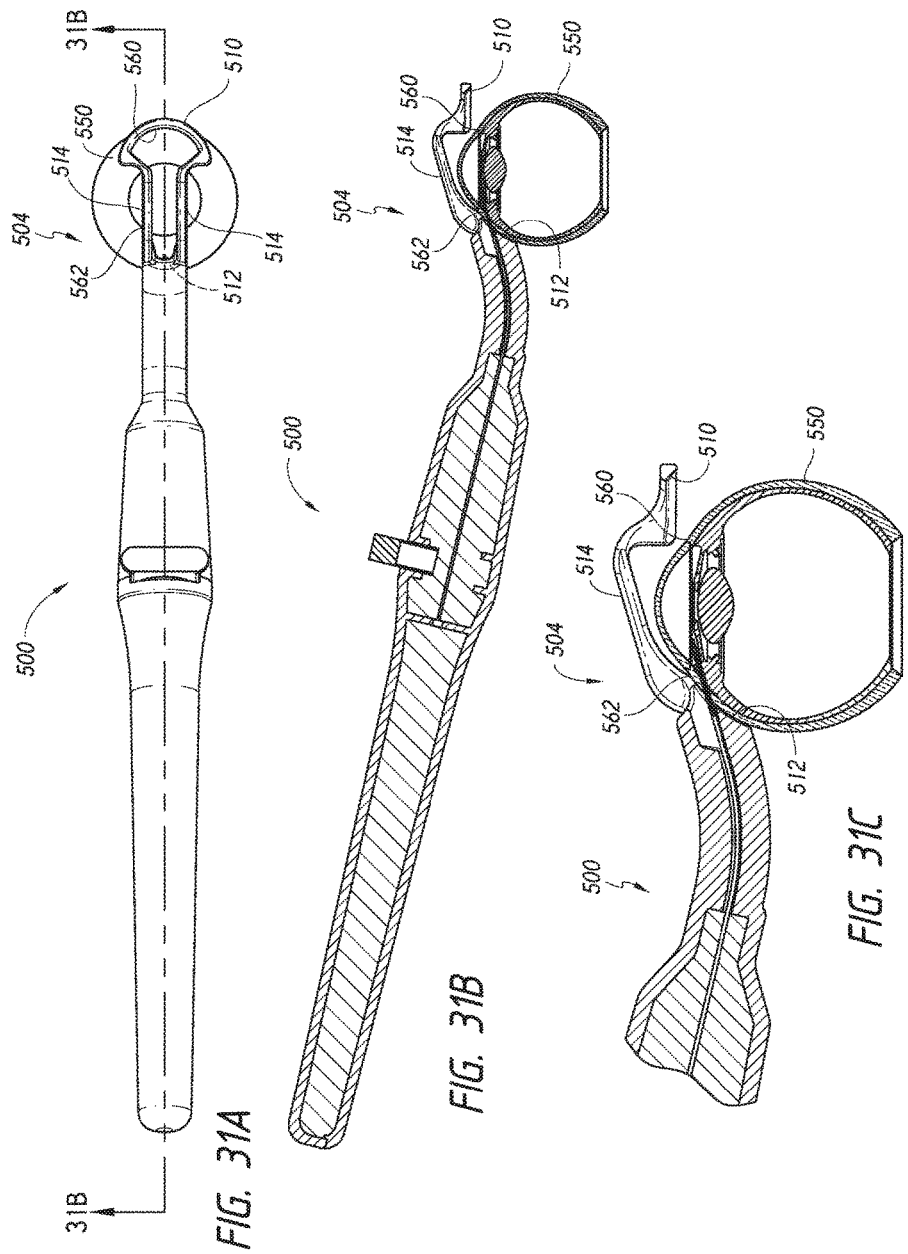

AB EXTERNO INTRAOCULAR SHUNT PLACEMENT

CROSS-REFERENCE TO RELATED APPLICATIONS

This application claims the benefit of U.S. Patent Application No. 62/170,338, filed on Jun. 3, 2015, and of U.S. Patent Application No. 62/279,585, filed on Jan. 15, 2016, the entirety of each of which is incorporated herein by reference.

FIELD OF THE INVENTIONS

The present disclosure generally relates to devices and ab externo methods of implanting an intraocular shunt into an eye.

BACKGROUND

Glaucoma is a disease in which the optic nerve is damaged, leading to progressive, irreversible loss of vision. It is typically associated with increased pressure of the fluid (i.e., aqueous humor) in the eye. Untreated glaucoma leads to permanent damage of the optic nerve and resultant visual field loss, which can progress to blindness. Once lost, this damaged visual field cannot be recovered. Glaucoma is the second leading cause of blindness in the world, affecting 1 in 200 people under the age of fifty, and 1 in 10 over the age of eighty for a total of approximately 70 million people worldwide.

In conditions of glaucoma, the pressure of the aqueous humor in the eye (anterior chamber) increases and this resultant increase of pressure can cause damage to the vascular system at the back of the eye and especially to the optic nerve. The treatment of glaucoma and other diseases that lead to elevated pressure in the anterior chamber involves relieving pressure within the anterior chamber to a normal level.

The importance of lowering intraocular pressure (IOP) in delaying glaucomatous progression has been well documented. When drug therapy fails, or is not tolerated, surgical intervention is warranted. Surgical filtration methods for lowering intraocular pressure by creating a fluid drainage pathway between the anterior chamber and an area of lower pressure have been described. Intraocular shunts can be positioned in the eye to drain fluid from the anterior chamber to locations such as the sub-Tenon's space, the subconjunctival space, the episcleral vein, the suprachoroidal space, Schlemm's canal, and the intrascleral space.

Methods of implanting intraocular shunts are known in the art. Shunts may be implanted using an ab externo approach (entering through the conjunctiva and inwards through the sclera) or an ab interno approach (entering through the cornea, across the anterior chamber, through the trabecular meshwork and sclera).

Positioning of an intraocular shunt to drain fluid into the intrascleral space is promising because it avoids contact with the conjunctiva and the suprachoroidal space. Avoiding contact with the conjunctiva and choroid is important because it reduces irritation, inflammation and tissue reaction, which can lead to fibrosis and reduce the outflow potential of the subconjunctival and suprachoroidal space. The conjunctiva itself plays a critical role in glaucoma filtration surgery. A less irritated and healthy conjunctiva allows drainage channels to form and less opportunity for inflammation and scar tissue formation. Intrascleral shunt placement safeguards the integrity of the conjunctiva and choroid, but may provide only limited outflow pathways that may affect the long term IOP lowering efficacy.

SUMMARY

Traditional ab externo approaches are shown for example in Nissan et al. (U.S. Pat. No. 8,109,896), Tu et al. (U.S. Pat. No. 8,075,511), and Haffner et al. (U.S. Pat. No. 7,879,001), the content of each of which is incorporated by reference herein in its entirety.

In such traditional surgeries, a distal end of a deployment device or injector is used to make a scleral flap or slit to access the eye. The conjunctiva can be dissected or pulled away from the sclera to expose the sclera. In some instances, this can allow the surgeon to cut and separate a small flap of the sclera away from the underlying sclera. A needle can then be inserted into the eye below the scleral flap to access the anterior angle of the eye. The needle is then withdrawn, leaving a scleral slit behind.

Thereafter, a silicone tube with sufficient stiffness is manually pushed through the scleral slit from the outside so that the distal tube ends distal to the trabecular meshwork in the anterior chamber of the eye. In some instances, the scleral flap can be repositioned over the proximal end of the tube and sutures can be used to re-secure the flap and conjunctiva. In other instances where only the conjunctiva is dissected, the proximal end of the tube can be positioned to exit the sclera, lay on top of it, and be connected to a plate that is fixated by sutures to the outside scleral surface (and within a pocket underlying the conjunctiva) far away (>10 mm) from the limbus.

Some of the problems associated with this surgery include the necessity to cauterize to avoid significant bleeding and the large size of the remaining silicone tube and plate. Due to the obtrusive nature of the silicone tube and plate, these can eventually cause the conjunctiva to erode, requiring a scleral graft to be placed over the silicone tube and plate.

The present disclosure provides various new methods and device concepts for an ab externo implantation of an intraocular shunt, such as a gel shunt. Some embodiments disclosed herein provide an associated injector docking device for maintaining, securing, or fixing a position of an injector relative to the eye during eye surgery. One of the aims is to create a simple and safe procedure that can be performed in an office setting. These new ab externo approaches provided by some embodiments can use a deployment device or injector similar in operation to the current XEN Injector produced by Applicant. Further, these new ab externo approaches can be implemented using the injector by itself or by using the injector in combination with one or more injector docking devices.

According to some embodiments, ab externo procedures are provided herein that enable an outflow end of a shunt to be deployed under/into any of a variety of outflow regions without making a scleral flap or otherwise requiring a conjunctival dissection. Thus, the outflow end of the shunt can be positioned in target outflow regions including the subconjunctival space or over-Tenon's space (between Tenon's and conjunctiva), the suprascleral or sub-Tenon's space (between Tenon's and sclera), the intra-Tenon's space (between layers of Tenon's capsule, or in the intra-Tenon's adhesion space), the choroidal and suprachoroidal space, the intrascleral space (between layers of sclera), Schlemm's canal, the vitreous space, the episcleral vein, or the supraciliary space. According to some embodiments disclosed herein, any of these target outflow regions can be ballooned to create an outflow reservoir or space. As discussed herein, the ballooning can be done via an injection of a basic salt solution ("BSS"), a viscoelastic, an anti-metabolite, a drug-eluting solution, water, and/or a combination thereof. Further, in accordance with some embodiments in which the outflow end of the shunt is placed in the intra-Tenon's adhesion space, the Tenon adhesions remain intact, just as they would for an ab interno approach. Thus, a needle of a shunt injector can pierce conjunctiva, sclera, and in some embodiments, Tenon's capsule, as it is advanced into the eye to position the shunt within the eye without creating a scleral flap or conjunctival dissection. For example, the shunt can provide fluid communication between the anterior chamber and a desired target outflow region.

In accordance with some embodiments, a surgeon can inject a fluid ab externo into the target outflow region to create a bleb in order to facilitate positioning of an outflow end of a shunt within the target outflow region. In some embodiments, the bleb can be created after the shunt is implanted into the eye and the injector is removed. However, in some embodiments, the bleb can be created prior to implantation of the shunt. Further, the bleb can be created prior to implantation of the shunt and reinflated after the shunt has been implanted.

For example, a surgeon can insert a shunt through a bleb such that an inflow or distal end of the shunt is positioned in a region of higher pressure in the eye (e.g., the anterior chamber) and an outflow or proximal end of the shunt is positioned in a region of lower pressure in the eye (e.g., the outflow proximal end of the shunt is positioned within the bleb in the target outflow region). Once the shunt is in position, the bleb can eventually deflate and collapse against the outflow end of the shunt, thereby positioning the outflow end of the shunt against the contour of the eye. Thereafter, the shunt can provide a drainage pathway from the region of higher pressure to the target outflow region.

Advantageously, some embodiments therefore provide methods and devices that place an intraocular shunt ab externo into the eye without requiring a low gauge silicone tube or diffusion plate attached to the tube, as used in the prior art. Instead, according to some embodiments, a higher gauge needle and intraocular shunt can be placed without causing significant trauma to the eye. The shunt can be inserted through the target outflow region and ejected from the needle such that an inflow end of the shunt resides in the anterior chamber of the eye and an outflow end of the needle resides in the target outflow region.

Moreover, in some embodiments, a surgeon can use an injector docking device to facilitate positioning and maintaining an orientation of the shunt relative to one or more aspects of the eye. The injector docking device can optionally comprise one or more structures that can facilitate positioning of the injector docking device onto or around the eye. Optionally, the injector docking device can comprise one or more features that can secure the injector docking device relative to the eye once a desired position has been achieved. In some embodiments, such features can be selectively activated once the injector docking device is in a desired position. Such features can include vacuum suction and/or surface friction elements (such as ridges, micro-hooks, or other such elements that can increase the surface contact and/or friction between the injector docking device and the eye). In some embodiments, suction and mechanical engagement can be used alone or together to enable the injector docking device to be coupled to or removably affixed to the eye.

The subject technology is illustrated, for example, according to various aspects described below. Various examples of aspects of the subject technology are described as numbered clauses (1, 2, 3, etc.) for convenience. These are provided as examples and do not limit the subject technology. It is noted that any of the dependent clauses may be combined in any combination, and placed into a respective independent clause, e.g., Clause 1 or Clause 13. The other clauses can be presented in a similar manner.

Clause 1. An injector docking device for placing an intraocular shunt into an eye, the device comprising: a needle support component having proximal and distal portions and a longitudinal needle axis extending between the proximal and distal portions, the support component being configured such that, when coupled to an intraocular shunt inserter, the proximal or distal portion supports the inserter to align a needle of the inserter with the longitudinal needle axis; and an eye-contacting surface disposed on the distal portion of the needle support component, the eye-contacting surface being positionable against the eye to permit a clinician to align the device relative to an indicium of the eye thereby aligning the needle relative to the eye.

Clause 2. The docking device of Clause 1, wherein the eye-contacting surface comprises at least one arcuate surface for alignment of the docking device relative to an indicium of the eye and alignment of the needle axis to the eye.

Clause 3. The docking device of Clause 2, wherein the eye-contacting surface is at least partially concave.

Clause 4. The docking device of the preceding Clauses, wherein the docking device comprises a body width that increases from the proximal portion to the distal portion.

Clause 5. The docking device of the preceding Clauses, wherein the distal portion flares outwardly.

Clause 6. The docking device of the preceding Clauses, wherein the eye-contacting surface extends proximally from the distal portion toward the proximal portion.

Clause 7. The docking device of the preceding Clauses, wherein the eye-contacting surface extends from an arcuate edge of the distal portion, the arcuate edge being positionable adjacent to a corneal limbus of the eye for aligning the device relative to the eye.

Clause 8. The docking device of the preceding Clauses, wherein the eye-contacting surface extends proximally from a distal end of the needle support component.

Clause 9. The docking device of the preceding Clauses, wherein the distal portion comprises a ring-shaped component.

Clause 10. The docking device of the preceding Clauses, wherein the distal portion comprises a half-ring component.

Clause 11. The docking device of the preceding Clauses, wherein when coupled with the inserter, the needle of the inserter is coaxial with the longitudinal needle axis.

Clause 12. The docking device of the preceding Clauses, wherein the support component is detachable from an intraocular shunt inserter.

Clause 13. The docking device of the preceding Clauses, wherein the support component surrounds at least a portion of the needle.

Clause 14. The docking device of the preceding Clauses, wherein the needle support component comprises an elongate shaft and a needle port extending therethrough.

Clause 15. The docking device of Clause 14, wherein the needle port extends through the eye-contacting surface.

Clause 16. The docking device of the preceding Clauses, wherein the needle axis extends through the eye-contacting surface.

Clause 17. The docking device of the preceding Clauses, wherein eye-contacting surface comprises a blunt face positionable against the eye, the blunt face having a surface area of at least about 5 mm2.

Clause 18. The docking device of the preceding Clauses, wherein eye-contacting surface comprises a blunt face positionable against the eye, the blunt face having a surface area of at least about 10 mm2.

Clause 19. The docking device of the preceding Clauses, wherein eye-contacting surface comprises a single, continuous surface through which the needle axis passes.

Clause 20. The docking device of the preceding Clauses, wherein a portion of the needle support component is transparent to facilitate visualization of the needle or an indicium of the eye.

Clause 21. The docking device of Clause 1, further comprising an annular body coupled to the needle support component, the annular body comprising the eye-contacting surface.

Clause 22. An injector docking device for placing an intraocular shunt into an eye, the device comprising: an annular body; an eye-contacting portion formed on a first side of the annular body, the eye-contacting portion extending about a central axis of the body; and a needle support component extending from the annular body, the needle support component comprising a needle port, the needle port defining a needle axis extending toward the eye-contacting portion.

Clause 23. An injector docking device for placing an intraocular shunt into an eye, the docking device comprising: an arcuate body comprising an eye-contacting portion formed on a first side of the arcuate body; and a needle support component coupled to the arcuate body, the needle support component comprising a needle port, the needle port defining a needle axis extending toward the eye-contacting portion.

Clause 24. The docking device of Clause 23, wherein the arcuate body comprises an annular structure.

Clause 25. The docking device of any of Clauses 23-24, wherein the arcuate body comprises first and second components.

Clause 26. The docking device of Clause 25, wherein the first and second components are coupled together via a bridge, the first component spaced apart from the second component, the first component comprising a semicircular shape.

Clause 27. The docking device of Clause 26, wherein the needle axis extends through the second component toward the first component.

Clause 28. The docking device of any of Clauses 26-27, wherein the needle axis does not intersect with the bridge.

Clause 29. The docking device of any of Clauses 23-28, wherein the eye-contacting portion comprises a scleral contact surface and a corneal contact surface, the scleral contact surface defining a first radius of curvature, the corneal contact surface defining a second radius of curvature different than the first radius of curvature.

Clause 30. The docking device of Clause 29, wherein the first radius of curvature is greater than the second radius of curvature.

Clause 31. The docking device of any of Clauses 29-30, wherein the scleral contact surface and the corneal contact surface meet at a limbus ridge, the limbus ridge comprising a circular protrusion extending in a direction away from the eye-contacting portion.

Clause 32. The docking device of any of Clauses 23-31, wherein the needle support component comprises a shaft having the needle port extending therethrough, the needle port comprising a lumen within the shaft.

Clause 33. The docking device of any of Clauses 23-32, wherein the eye-contacting portion comprises an adhesion component for coupling the injector docking device to the eye.

Clause 34. The docking device of Clause 33, wherein the adhesion component comprises a plurality of spikes.

Clause 35. The docking device of any of Clauses 33-34, wherein the adhesion component comprises a channel for applying vacuum pressure to a surface of the eye.

Clause 36. The docking device of Clause 35, wherein the channel extends along a scleral contact surface of the body.

Clause 37. The docking device of any of Clauses 35-36, wherein the channel extends along a corneal contact surface of the body.

Clause 38. The docking device of any of Clauses 35-37, further comprising a vacuum port in fluid communication with the channel, the vacuum port extending from an upper portion of the body opposite the first side.

Clause 39. The docking device of any of Clauses 23-38, wherein the arcuate body extends about a central axis, and wherein needle axis extends at an angle of between about 48 degrees to about 98 degrees with respect to the central axis.

Clause 40. The docking device of any of Clauses 23-39, wherein the arcuate body extends about a central axis, and wherein the needle axis extends at an angle of between about 65 degrees to about 75 degrees with respect to the central axis.

Clause 41. The docking device of any of Clauses 23-40, wherein the arcuate body extends about a central axis, and wherein the needle axis extends at an angle of about 70 degrees with respect to the central axis.

Clause 42. The docking device of any of Clauses 23-41, wherein the arcuate body extends about a central axis, and wherein the needle axis extends toward the central axis.

Clause 43. The docking device of Clause 42, wherein the needle axis intersects with the central axis.

Clause 44. The docking device of any of Clauses 23-43, further comprising an alignment aperture extending through the body from an upper portion of the body to the eye-contacting portion.

Clause 45. The docking device of Clause 44, wherein the alignment aperture defines a diameter of between about 8 mm to about 15 mm.

Clause 46. The docking device of Clause 44, wherein the alignment aperture defines a diameter of between about 11.5 mm to about 12.5 mm.

Clause 47. The docking device of Clause 44, wherein the alignment aperture defines a diameter of about 12 mm.

Clause 48. The docking device of any of Clauses 23-47, further comprising a bleb pocket adjacent to the needle port, the bleb pocket comprising a concavity extending into the body from the eye-contacting portion toward an upper portion of the body.

Clause 49. The docking device of Clause 48, wherein the needle port comprises an outlet, the outlet being disposed along the bleb pocket.

Clause 50. An intraocular inserter comprising a handle component and the injector docking device of any of Clauses 1-49.

Clause 51. An injector docking device for placing an intraocular shunt into an eye, the injector docking device comprising: a body comprising first and second eye-contacting components coupled together via a bridge, the first eye-contacting component spaced apart from the second eye-contacting component, the first eye-contacting component comprising a semicircular shape; and a needle support component coupled to the second eye-contacting component of the body, the needle support component comprising a needle port, the needle port defining a needle axis extending through the second eye-contacting component toward the first eye-contacting component.

Clause 52. The docking device of Clause 51, wherein the needle axis does not intersect with the bridge.

Clause 53. The docking device of any of Clauses 51-52, wherein the first eye-contacting component comprises a plurality of spikes for coupling the injector docking device to the eye.

Clause 54. The docking device of any of Clauses 51-53, wherein the first eye-contacting component comprises a channel for applying vacuum pressure to a surface of the eye.

Clause 55. The docking device of Clause 54, wherein the channel extends along a scleral contact surface of the first eye-contacting component.

Clause 56. The docking device of any of Clauses 54-55, wherein the channel extends along a corneal contact surface of the first eye-contacting component.

Clause 57. The docking device of any of Clauses 54-56, further comprising a vacuum port in fluid communication with the channel, the vacuum port extending from an upper portion of the body.

Clause 58. The docking device of any of Clauses 51-57, further comprising an alignment aperture extending through the bridge.

Clause 59. The docking device of any of Clauses 51-58, further comprising a bleb pocket in the second eye-contacting component adjacent to the needle port, the bleb pocket comprising a concavity extending into the second eye-contacting component.

Clause 60. The docking device of Clause 59, wherein the needle port comprises an outlet, the outlet being disposed along the bleb pocket.

Clause 61. The docking device of any of Clauses 51-60, wherein the needle support component comprises a shaft having the needle port extending therethrough, the needle port comprising a lumen within the shaft.

Clause 62. An intraocular inserter comprising a handle component and the injector docking device of any of Clauses 51-61.

Clause 63. An injector docking device for placing an intraocular shunt into an eye, the docking device comprising: a body comprising an annular eye-contacting component; and a needle support component coupled to the annular eye-contacting component of the body, the needle support component comprising a needle port, the needle port defining a needle axis extending toward the annular eye-contacting component.

Clause 64. The docking device of Clause 63, wherein the annular eye-contacting component comprises a gap adjacent to the needle support component, the needle port extending to the gap toward a central axis of the annular eye-contacting component.

Clause 65. The docking device of any of Clauses 63-64, wherein the annular eye-contacting portion comprises a scleral contact surface and a corneal contact surface, the scleral contact surface defining a first radius of curvature, the corneal contact surface defining a second radius of curvature different than the first radius of curvature.

Clause 66. The docking device of Clause 65, wherein the first radius of curvature is greater than the second radius of curvature.

Clause 67. The docking device of any of Clauses 65-66, wherein the scleral contact surface and the corneal contact surface meet at a limbus ridge, the limbus ridge comprising a circular protrusion extending in a direction away from the eye-contacting portion.

Clause 68. The docking device of any of Clauses 63-67, wherein the needle support component comprises a shaft having the needle port extending therethrough, the needle port comprising a lumen within the shaft.

Clause 69. The docking device of any of Clauses 63-68, wherein the annular eye-contacting portion comprises an adhesion component for coupling the injector docking device to the eye.

Clause 70. The docking device of Clause 69, wherein the adhesion component comprises a plurality of spikes.

Clause 71. The docking device of any of Clauses 69-70, wherein the adhesion component comprises a channel for applying vacuum pressure to a surface of the eye.

Clause 72. The docking device of Clause 71, wherein the channel extends along a scleral contact surface of the body.

Clause 73. The docking device of any of Clauses 71-72, wherein the channel extends along a corneal contact surface of the body.

Clause 74. The docking device of any of Clauses 71-73, further comprising a vacuum port in fluid communication with the channel, the vacuum port extending from an upper portion of the body.

Clause 75. The docking device of any of Clauses 63-74, wherein the annular eye-contacting component extends about a central axis, and wherein needle axis extends at an angle of between about 48 degrees to about 98 degrees with respect to the central axis.

Clause 76. The docking device of any of Clauses 63-75, wherein the annular eye-contacting component extends about a central axis, and wherein the needle axis extends at an angle of between about 65 degrees to about 75 degrees with respect to the central axis.

Clause 77. The docking device of any of Clauses 63-76, wherein the annular eye-contacting component extends about a central axis, and wherein the needle axis extends at an angle of about 70 degrees with respect to the central axis.

Clause 78. The docking device of any of Clauses 63-77, wherein the annular eye-contacting component extends about a central axis, and wherein the needle axis extends toward the central axis.

Clause 79. The docking device of Clause 63, wherein the needle axis intersects with the central axis.

Clause 80. The docking device of any of Clauses 63-79, further comprising an alignment aperture extending through the body from an upper portion of the body to the eye-contacting portion.

Clause 81. The docking device of Clause 80, wherein the alignment aperture defines a diameter of between about 8 mm to about 15 mm.

Clause 82. The docking device of Clause 80, wherein the alignment aperture defines a diameter of between about 11.5 mm to about 12.5 mm.

Clause 83. The docking device of Clause 80, wherein the alignment aperture defines a diameter of about 12 mm.

Clause 84. The docking device of any of Clauses 63-83, further comprising a bleb pocket adjacent to the needle port, the bleb pocket comprising a concavity extending into the body from the eye-contacting portion toward an upper portion of the body.

Clause 85. The docking device of Clause 84, wherein the needle port comprises an outlet, the outlet being disposed along the bleb pocket.

Clause 86. An intraocular inserter comprising a handle component and the injector docking device of any of Clauses 63-86.

Clause 87. An injector docking device for placing an intraocular shunt into an eye, the injector docking device comprising: a body comprising an elongate eye-contacting component having at least one tip portion for contacting the eye; and a needle support component coupled to the elongate eye-contacting component of the body, the needle support component comprising a needle port, the needle port defining a needle axis extending in a direction of the at least one tip portion elongate eye-contacting component.

Clause 88. The docking device of Clause 87, wherein the elongate eye-contacting component comprises a pair of prongs having proximal ends coupled to the needle support component, the proximal ends thereof being spaced apart by a gap and having the needle port extending to the gap.

Clause 89. The docking device of Clause 88, wherein the pair of prongs diverges to increase a size of the gap in a direction away from the needle support component.

Clause 90. The docking device of any of Clauses 87-89, wherein the needle support component comprises a shaft having the needle port extending therethrough, the needle port comprising a lumen within the shaft.

Clause 91. The docking device of any of Clauses 87-89, wherein the elongate eye-contacting portion comprises an adhesion component for coupling the injector docking device to the eye.

Clause 92. The docking device of Clause 91, wherein the adhesion component comprises a plurality of spikes.

Clause 93. The docking device of any of Clauses 91-92, wherein the adhesion component comprises a channel for applying vacuum pressure to a surface of the eye.

Clause 94. The docking device of Clause 93, wherein the channel extends along a scleral contact surface of the body.

Clause 95. The docking device of any of Clauses 93-94, wherein the channel extends along a corneal contact surface of the body.

Clause 96. The docking device of any of Clauses 93-94, further comprising a vacuum port in fluid communication with the channel, the vacuum port extending from an upper portion of the body.

Clause 97. An intraocular inserter comprising a handle component and the injector docking device of any of Clauses 87-96.

Clause 98. An inserter comprising the docking device of any of the preceding Clauses, wherein the inserter and the docking device being formed as a single, continuous piece of material.

Clause 99. An ab externo method of placing an intraocular shunt into an eye, the method comprising the steps of: determining an entry area below a corneal limbus of an eye and a target outflow region; inserting a hollow shaft into the eye at the entry area toward an anterior chamber of the eye, the shaft configured to hold an intraocular shunt; positioning an inflow end of the shunt within the anterior chamber of the eye; while maintaining the shunt inflow end in the anterior chamber, removing the shaft from the eye to release the shunt; and verifying placement of an outflow end of the shunt within the target outflow region.

Clause 100. The method of Clause 99, further comprising ballooning the target outflow region of the eye.

Clause 101. The method of Clause 100, wherein the ballooning comprises forming a bleb in the target outflow region.

Clause 102. The method of Clause 101, further comprising massaging the bleb in a direction away from the corneal limbus to reposition the outflow end of the shunt within the target outflow region.

Clause 103. The method of Clause 100, wherein the ballooning is performed prior to inserting the hollow shaft into the eye.

Clause 104. The method of Clause 103, further comprising ballooning the target outflow region after the shunt is released to reinflate the target outflow region.

Clause 105. The method of Clause 100, wherein the ballooning is performed after removing the shaft from the eye.

Clause 106. The method of any of Clauses 100-105, wherein the ballooning comprises injecting an aqueous solution into the eye.

Clause 107. The method of any of Clauses 100-105, wherein the ballooning comprises injecting a balanced salt solution, lidocaine, a healon solution, or a viscoelastic into the eye.

Clause 108. The method of any of Clauses 99-107, wherein the positioning an inflow end of the shunt comprises advancing the shaft and the shunt together in a pre-deployment configuration in which the inflow end of the shunt is positioned adjacent to a bevel of the shaft.

Clause 109. The method of any of Clauses 99-108, wherein the positioning an inflow end of the shunt comprises pushing the shunt within the shaft using a plunger rod while maintaining a relative position between the shaft and the eye.

Clause 110. The method of any of Clauses 99-109, wherein the target outflow region comprises a subconjunctival space, a sub-Tenon's space, an intra-Tenon's space, an over-Tenon's space, a suprachoroidal space, an intrascleral space, Schlemm's canal, a vitreous space, an episcleral vein, a supraciliary space, or a suprascleral space.

Clause 111. The method of any of Clauses 99-110, further comprising: positioning an injector docking device on the eye, the injector docking device comprising a needle port having a longitudinal axis; and orienting the needle port longitudinal axis to intersect with the entry area and extend toward the anterior chamber.

Clause 112. The method of Clause 111, wherein the injector docking device comprises a vacuum pocket on an eye-contacting surface thereof, the method further comprising applying suction between the injector docking device and the eye via the vacuum pocket to removably couple the injector docking device to the eye.

Clause 113. The method of any of Clauses 111-112, further comprising removably coupling the injector docking device to the eye via frictional or mechanical engagement.

Clause 114. The method of Clause 113, wherein the injector docking device comprises a plurality of spikes on an eye-contacting surface thereof, the method further comprising engaging the plurality of spikes with conjunctiva of the eye.

Clause 115. The method of any of Clauses 111-114, wherein the inserting the hollow shaft comprises inserting the hollow shaft into the needle port and advancing the shaft through the needle port into the eye via the entry area toward the anterior chamber.

Clause 116. The method of any of Clauses 111-115, wherein the injector docking device comprises a bleb pocket adjacent to the needle port, the method further comprising positioning the bleb pocket over a ballooned portion of the target outflow region.

Clause 117. The method of Clause 116, further comprising, before positioning the injector docking device on the eye, ballooning the target outflow region of the eye.

Clause 118. The method of Clause 111, wherein the injector docking device comprises an eye-contacting portion having a half-ring component, wherein the positioning comprises positioning the half-ring component against the eye.

Clause 119. The method of Clause 118, wherein the positioning comprises positioning the half-ring component adjacent to the corneal limbus.

Clause 120. The method of any of Clauses 118-119, wherein the positioning comprises positioning the half-ring component in a location opposite the target outflow region along the corneal limbus.

Clause 121. The method of any of Clauses 118-120, wherein the eye-contacting portion further comprises an abutment portion, spaced apart from the half-ring component, the method further comprising positioning the abutment portion against the eye.

Clause 122. The method of Clause 121, wherein the positioning comprises positioning the abutment portion adjacent to the target outflow region.

Clause 123. The method of Clause 121, wherein the positioning comprises positioning the half-ring component against the eye adjacent to the corneal limbus to provide an initial alignment of the hollow shaft, and, after achieving an initial alignment, moving the abutment portion into contact with the eye adjacent the target outflow region, thereby inserting the hollow shaft into the eye at the entry area.

Clause 124. The method of any of Clauses 118-123, wherein the half-ring component comprises a vacuum pocket, the method further comprising applying suction between the half-ring component and the eye via the vacuum pocket to removably couple the injector docking device to the eye.

Clause 125. The method of Clause 111, wherein the injector docking device comprises a ring-shaped structure having an eye-contacting surface configured to contact the eye, the method further comprising positioning the ring-shaped structure to place the eye-contacting surface against the eye.

Clause 126. The method of Clause 125, wherein the eye-contacting surface is positioned adjacent to the corneal limbus.

Clause 127. The method of Clause 125, wherein the eye-contacting surface is extends along a majority of the corneal limbus.

Clause 128. The method of any of Clauses 125-127, wherein the ring-shaped structure comprises a vacuum pocket, the method further comprising applying suction between the ring-shaped structure and the eye via the vacuum pocket to removably couple the injector docking device to the eye.

Clause 129. The method of Clause 111, wherein the injector docking device comprises a pair of prongs extending therefrom, the method comprising positioning tip portions of the prongs in contact with the eye to facilitate alignment of the needle port longitudinal axis relative to the entry area.

Clause 130. The method of Clause 129, wherein the positioning comprises positioning the prong tip portions against the corneal limbus of the eye.

Clause 131. The method of Clause 129, wherein the positioning comprises positioning the prong tip portions against the eye adjacent to the corneal limbus.

Clause 132. An ab externo method of placing an intraocular shunt into an eye, the method comprising the steps of: ballooning a target outflow region within an eye; positioning an injector docking device, having a needle port, against the eye, the needle port being aligned with the target outflow region; inserting a hollow shaft through the needle port to align the hollow shaft with the target outflow region, the hollow shaft housing an intraocular shunt therein; advancing the hollow shaft into the eye toward an anterior chamber of the eye; positioning an inflow end of the shunt within the anterior chamber of the eye and an outflow end of the shunt within the target outflow region; and while maintaining the longitudinal position of the shunt relative to the eye, removing the shaft from the eye to release the shunt.

Clause 133. The method of Clause 132, wherein the positioning the injector docking device comprises aligning a longitudinal axis of the needle port with the target outflow region.

Clause 134. The method of any of Clauses 132-133, wherein the ballooning comprises forming a bleb in the target outflow region.

Clause 135. The method of Clause 134, further comprising after removing the shaft from the eye, massaging the bleb in a direction away from the corneal limbus to reposition the outflow end of the shunt within the target outflow region.

Clause 136. The method of any of Clauses 132-135, wherein the ballooning is performed prior to inserting the hollow shaft into the eye.

Clause 137. The method of any of Clauses 132-136, further comprising ballooning the target outflow region after the shunt is released to reinflate the target outflow region.

Clause 138. The method of any of Clauses 132-137, wherein the ballooning is performed after removing the shaft from the eye.

Clause 139. The method of any of Clauses 132-138, wherein the ballooning comprises injecting an aqueous solution into the eye.

Clause 140. The method of any of Clauses 132-139, wherein the ballooning comprises injecting a balanced salt solution, lidocaine, a healon solution, or a viscoelastic into the eye.

Clause 141. The method of any of Clauses 132-140, wherein the positioning an inflow end of the shunt comprises advancing the shaft and the shunt together in a pre-deployment configuration in which the inflow end of the shunt is positioned adjacent to a bevel of the shaft.

Clause 142. The method of any of Clauses 132-140, wherein the positioning an inflow end of the shunt comprises pushing the shunt within the shaft using a plunger rod while maintaining a relative position between the shaft and the eye.

Clause 143. The method of any of Clauses 132-142, wherein the target outflow region comprises a subconjunctival space, a sub-Tenon's space, an intra-Tenon's space, an over-Tenon's space, a suprachoroidal space, an intrascleral space, Schlemm's canal, a vitreous space, an episcleral vein, a supraciliary space, or a suprascleral space.

Clause 144. The method of any of Clauses 132-143, wherein the injector docking device comprises a vacuum pocket on an eye-contacting surface thereof, the method further comprising applying suction between the injector docking device and the eye via the vacuum pocket to removably couple the injector docking device to the eye.

Clause 145. The method of any of Clauses 132-144, further comprising removably coupling the injector docking device to the eye via frictional or mechanical engagement.

Clause 146. The method of Clause 145, wherein the injector docking device comprises a plurality of spikes on an eye-contacting surface thereof, the method further comprising engaging the plurality of spikes with conjunctiva of the eye.

Clause 147. The method of any of Clauses 132-146, wherein the injector docking device comprises a bleb pocket adjacent to the needle port, the method further comprising positioning the bleb pocket over a ballooned portion of the target outflow region.

Clause 148. The method of Clause 147, wherein a longitudinal axis of the needle port intersects with the bleb pocket.

Clause 149. The method of any of Clauses 132-148, wherein the injector docking device comprises an eye-contacting portion having a half-ring component, wherein the positioning the injector docking device comprises positioning the half-ring component against the eye.

Clause 150. The method of Clause 149, wherein the positioning the injector docking device comprises positioning the half-ring component adjacent to the corneal limbus.

Clause 151. The method of any of Clauses 149-151, wherein the positioning the injector docking device comprises positioning the half-ring component in a location opposite the target outflow region along the corneal limbus.

Clause 152. The method of any of Clauses 149-152, wherein the eye-contacting portion further comprises an abutment portion, spaced apart from the half-ring component, the method further comprising positioning the abutment portion against the eye.

Clause 153. The method of Clause 152, wherein the positioning the abutment portion comprises positioning the abutment portion adjacent to the target outflow region.

Clause 154. The method of any of Clauses 152-153, wherein the positioning the abutment portion comprises positioning the half-ring component against the eye adjacent to the corneal limbus to provide an initial alignment of the hollow shaft, and, after achieving an initial alignment, moving the abutment portion into contact with the eye adjacent the target outflow region, thereby inserting the hollow shaft into the eye.

Clause 155. The method of any of Clauses 149-154, wherein the half-ring component comprises a vacuum pocket, the method further comprising applying suction between the half-ring component and the eye via the vacuum pocket to removably couple the injector docking device to the eye.

Clause 156. The method of any of Clauses 132-148, wherein the injector docking device comprises a ring-shaped structure having an eye-contacting surface configured to contact the eye, wherein the positioning the injector docking device comprises positioning the eye-contacting surface of the ring-shaped structure against the eye.

Clause 157. The method of Clause 156, wherein the eye-contacting surface is positioned adjacent to the corneal limbus.

Clause 158. The method of any of Clauses 156-157, wherein the eye-contacting surface is extends along a majority of the corneal limbus.

Clause 159. The method of any of Clauses 156-158, wherein the ring-shaped structure comprises a vacuum pocket, the method further comprising applying suction between the ring-shaped structure and the eye via the vacuum pocket to removably couple the injector docking device to the eye.

Clause 160. The method of any of Clauses 132-148, wherein the injector docking device comprises a pair of prongs extending therefrom, wherein the positioning the injector docking device comprises positioning tip portions of the prongs in contact with the eye to facilitate alignment of the needle port longitudinal axis relative to the target outflow region.

Clause 161. The method of Clause 160, wherein the positioning the injector docking device comprises positioning the prong tip portions against the corneal limbus of the eye.

Clause 162. The method of Clause 160, wherein the positioning the injector docking device comprises positioning the prong tip portions against the eye adjacent to the corneal limbus.

Clause 163. An ab externo method of placing an intraocular shunt into an eye, the method comprising the steps of: inserting a hollow shaft into an eye below a corneal limbus of the eye, the shaft housing an intraocular shunt; positioning an inflow end of the shunt within an anterior chamber of the eye; while maintaining the shunt inflow end in the anterior chamber, removing the shaft from the eye to release the shunt; and ballooning a target outflow region of the eye, the target outflow region being adjacent to an outflow end of the shunt, wherein the ballooning repositions the outflow end of the shunt within the eye in the target outflow region.

Clause 164. The method of Clause 163, wherein the ballooning comprises forming a bleb in the target outflow region.

Clause 165. The method of Clause 164, further comprising massaging the bleb in a direction away from the corneal limbus to reposition the outflow end of the shunt within the target outflow region.

Clause 166. The method of any of Clauses 163-165, wherein the ballooning comprises injecting an aqueous solution into the eye.

Clause 167. The method of any of Clauses 163-166, wherein the ballooning comprises injecting a balanced salt solution, lidocaine, a healon solution, or a viscoelastic into the eye.

Clause 168. The method of any of Clauses 163-167, wherein the positioning an inflow end of the shunt comprises advancing the shaft and the shunt together in a pre-deployment configuration in which the inflow end of the shunt is positioned adjacent to a bevel of the shaft.

Clause 169. The method of any of Clauses 163-168, wherein the positioning an inflow end of the shunt comprises pushing the shunt within the shaft using a plunger rod while maintaining a relative position between the shaft and the eye.

Clause 170. The method of any of Clauses 163-169, wherein the target outflow region comprises a subconjunctival space, a sub-Tenon's space, an intra-Tenon's space, an over-Tenon's space, a suprachoroidal space, an intrascleral space, Schlemm's canal, a vitreous space, an episcleral vein, a supraciliary space, or a suprascleral space.

Clause 171. The method of any of Clauses 163-170, further comprising: positioning an injector docking device on the eye, the injector docking device comprising a needle port having a longitudinal axis; and orienting the needle port longitudinal axis to intersect with the target outflow area and extend toward the anterior chamber.

Clause 172. The method of Clause 171, wherein the injector docking device comprises a vacuum pocket on an eye-contacting surface thereof, the method further comprising applying suction between the injector docking device and the eye via the vacuum pocket to removably couple the injector docking device to the eye.

Clause 173. The method of any of Clauses 171-172, further comprising removably coupling the injector docking device to the eye via frictional or mechanical engagement.

Clause 174. The method of Clause 173, wherein the injector docking device comprises a plurality of spikes on an eye-contacting surface thereof, the method further comprising engaging the plurality of spikes with conjunctiva of the eye.

Clause 175. The method of any of Clauses 171-174, wherein the inserting the hollow shaft comprises inserting the hollow shaft into the needle port and advancing the shaft through the needle port into the eye via the target outflow area toward the anterior chamber.

Clause 176. The method of any of Clauses 171-175, wherein the injector docking device comprises an eye-contacting portion having a half-ring component, wherein the positioning comprises positioning the half-ring component against the eye.

Clause 177. The method of Clause 176, wherein the positioning comprises positioning the half-ring component adjacent to the corneal limbus.

Clause 178. The method of any of Clauses 176-178, wherein the positioning comprises positioning the half-ring component in a location opposite the target outflow region along the corneal limbus.

Clause 179. The method of any of Clauses 176-179, wherein the eye-contacting portion further comprises an abutment portion, spaced apart from the half-ring component, the method further comprising positioning the abutment portion against the eye.

Clause 180. The method of Clause 179, wherein the positioning comprises positioning the abutment portion adjacent to the target outflow region.

Clause 181. The method of any of Clauses 179-180, wherein the positioning comprises positioning the half-ring component against the eye adjacent to the corneal limbus to provide an initial alignment of the hollow shaft, and, after achieving an initial alignment, moving the abutment portion into contact with the eye adjacent the target outflow region, thereby inserting the hollow shaft into the eye.

Clause 182. The method of any of Clauses 176-181, wherein the half-ring component comprises a vacuum pocket, the method further comprising applying suction between the half-ring component and the eye via the vacuum pocket to removably couple the injector docking device to the eye.

Clause 183. The method of any of Clauses 171-175, wherein the injector docking device comprises a ring-shaped structure having an eye-contacting surface configured to contact the eye, the method further comprising positioning the ring-shaped structure to place the eye-contacting surface against the eye.

Clause 184. The method of Clause 183, wherein the eye-contacting surface is positioned adjacent to the corneal limbus.

Clause 185. The method of any of Clauses 183-184, wherein the eye-contacting surface is extends along a majority of the corneal limbus.

Clause 186. The method of any of Clauses 183-185, wherein the ring-shaped structure comprises a vacuum pocket, the method further comprising applying suction between the ring-shaped structure and the eye via the vacuum pocket to removably couple the injector docking device to the eye.

Clause 187. The method of any of Clauses 171-175, wherein the injector docking device comprises a pair of prongs extending therefrom, the method comprising positioning tip portions of the prongs in contact with the eye to facilitate alignment of the needle port longitudinal axis relative to the target outflow area.

Clause 188. The method of Clause 187, wherein the positioning comprises positioning the prong tip portions against the corneal limbus of the eye.

Clause 189. The method of any of Clauses 187-188, wherein the positioning comprises positioning the prong tip portions against the eye adjacent to the corneal limbus.

Clause 190. An ab externo method of placing an intraocular shunt in an eye, the method comprising any steps of the methods of the preceding Clauses and using any of the inserters, components, or devices of the preceding Clauses.

Clause 191. A method of placing an intraocular shunt in the eye, the method comprising any steps of the methods of the preceding Clauses and wherein the shunt comprises a pharmaceutical or biological agent as a coating on an exterior surface of the shunt.

Clause 192. A method of placing an intraocular shunt in the eye, the method comprising any steps of the methods of the preceding Clauses and wherein the shunt comprises a pharmaceutical or biological agent comprises a coating on an interior surface of the shunt.

Clause 193. A method of placing an intraocular shunt in the eye, the method comprising any steps of the methods of the preceding Clauses and wherein a portion of the shunt is impregnated with a pharmaceutical or biological agent.

Clause 194. A method of placing an intraocular shunt in the eye, the method comprising any steps of the methods of the preceding Clauses and wherein the shunt comprises a time-release pharmaceutical or biological agent.

Clause 195. An injector docking device comprising any of the features of the inserters, components, or devices of the preceding Clauses.

Clause 196. An inserter for placing an intraocular shunt in an eye, comprising any of the features of the inserters, components, or devices of the preceding Clauses.

Some methods can comprise treatment with a drug or pharmaceutical, such as by implanting an intraocular shunt that has been coated and/or impregnated with a pharmaceutical and/or biological agent, by treating the eye topically with a pharmaceutical and/or biological agent, and/or by injecting a pharmaceutical and/or biological agent into the anterior chamber and/or a target outflow region, including any target outflow regions discussed or referenced herein, prior to or after releasing a shunt from the device. Suitable agents may include, for example, any of those disclosed in the following U.S. Pat. Nos. 8,785,394; 8,062,657; 7,799,336, 7,790,183; 7,033,605; 6,719,991; 6,558,686; 6,162,487; 5,902,283; 5,853,745, and 5,624,704; and U.S. Patent Publication No. 2008/0108933; the content of each of these references is incorporated by reference herein its entirety. Further examples of suitable agents include anti-mitotic pharmaceuticals such as Mitomycin-C or 5-Fluorouracil, anti-VEGF (such as Lucentis, Macugen, Avastin, VEGF or steroids), anti-coagulants, anti-metabolites, angiogenesis inhibitors, steroids, anti-inflammatories, antibiotics, brimonidine, timolol, prostaglandin analogs (such as travoprost, latanoprost, and tafluprost), prostamides (such as bimatoprost), cyclosporin, pilocarpine, corticosteroids and other steroid derivatives (such as hydrocortisone, dexamethasone, beclomethasone dipropionate, triamcinolone, triamcinolone acetate, cortisol benzoate), or other agents for treating conditions of the eye, such as glaucoma, dry eye, allergy, or conjunctivitis, to name a few.

Additional features and advantages of the subject technology will be set forth in the description below, and in part will be apparent from the description, or may be learned by practice of the subject technology. The advantages of the subject technology will be realized and attained by the structure particularly pointed out in the written description and embodiments hereof as well as the appended drawings.

It is to be understood that both the foregoing general description and the following detailed description are exemplary and explanatory and are intended to provide further explanation of the subject technology.

BRIEF DESCRIPTION OF THE DRAWINGS

Various features of illustrative embodiments of the inventions are described below with reference to the drawings. The illustrated embodiments are intended to illustrate, but not to limit, the inventions. The drawings contain the following figures:

FIG. 8 is a top plan view of the injector docking device of FIG. 6.

FIG. 9 is a bottom plan view of the injector docking device of FIG. 6.

FIGS. 25 and 26 illustrate another procedure for implanting an intraocular shunt into an eye using an injector and the injector docking device shown in FIGS. 23 and 24, according to some embodiments.

FIGS. 27-31F illustrate another injector docking device formed unitarily with an injector, as well as a related procedure for implanting an intraocular shunt into an eye, according to some embodiments.

DETAILED DESCRIPTION

Figure 1:
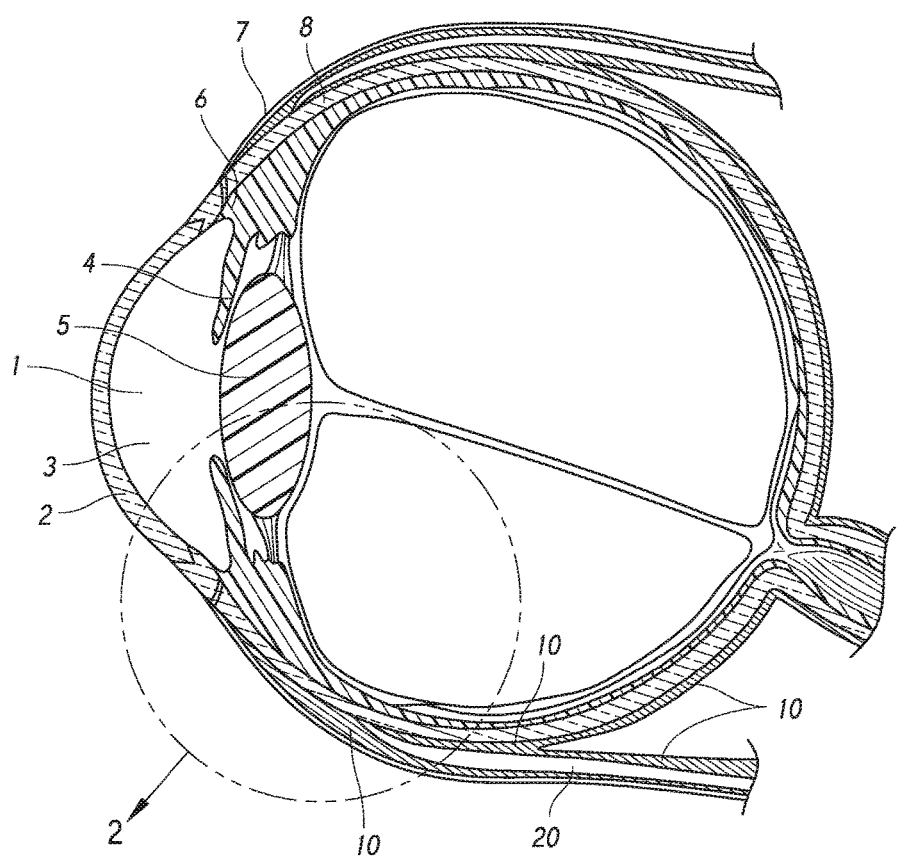
FIG. 1 is a cross-sectional diagram of the general anatomy of an eye.

In the following detailed description, numerous specific details are set forth to provide a full understanding of the subject technology. It should be understood that the subject technology may be practiced without some of these specific details. In other instances, well-known structures and techniques have not been shown in detail so as not to obscure the subject technology.

Further, while the present description sets forth specific details of various embodiments, it will be appreciated that the description is illustrative only and should not be construed in any way as limiting. Additionally, it is contemplated that although particular embodiments may be disclosed or shown in the context of ab externo procedures, such embodiments can be used in ab interno procedures. For example, although various ab externo approaches are discussed herein, any embodiment of the injector docking devices and methods described herein can be modified to provide an ab interno procedure (i.e. entering through the cornea, across the anterior chamber toward a target location) such that an outflow region of the shunt is positioned with the location of a bleb. Furthermore, various applications of such embodiments and modifications thereto, which may occur to those who are skilled in the art, are also encompassed by the general concepts described herein.

The present application discloses ab externo approaches and devices for positioning an intraocular shunt with one end (fluid entry end) placed into the anterior chamber and the other end (outflow end) placed preferably into a target outflow region, such as the subconjunctival space, without creating a conjunctival cutdown (dissection). Other possible shunt outflow locations or target outflow regions include the sub-Tenon's space (between Tenon's and sclera), the intra-Tenon's space (between layers of Tenon's capsule, or in the intra-Tenon's adhesion space), the over-Tenon's space (between Tenon's and conjunctiva), the suprachoroidal space, the intrascleral space, Schlemm's canal, the vitreous space, the episcleral vein, the supraciliary space, or the suprascleral space.

In some embodiments of the methods and devices disclosed herein, the injector can be configured to allow an intraocular shunt, such as a gel shunt (e.g., supported by a needle or shaft of the injector) to be positioned or oriented at a desired angle ("entrance angle") relative to a surface of the eye prior to implantation in order to allow the shunt outflow end to be positioned in a desired target outflow region, such as the suprachoroidal or vitreous space. For example, the injector can be manually positionable relative to the surface of the eye to allow the surgeon to adjust the entrance angle to any of a variety of angles before injecting the shunt into the eye.

Further, an injector docking device can also be used in combination with the injector to provide a fixed entrance angle, and a surgeon can select a specific injector docking device from a variety of rings having different fixed entrance angles based on a desired entrance angle. In some embodiments, the injector docking device can be removably couplable to the eye (e.g., via a vacuum force) or provide a smooth surface that can be positioned or abutted against the eye without being secured relative thereto. For example, some embodiments disclosed herein provide an associated injector docking device for maintaining, securing, or fixing a position of an injector relative to the eye during eye surgery.

Additionally, according to some embodiments, a shunt or stent can be injected into any of the nasal quadrants of the eye using an ab externo procedure. For example, the shunt can be injected in the nasal superior, nasal inferior, temporal superior, or temporal inferior quadrants.

Advantageously, using some embodiments of this procedure, a shunt can be more easily placed in every quadrant of the eye because the injector needle no longer has to traverse the entire anterior chamber (compared to ab interno approaches). Thus, ab externo procedures are disclosed herein that enable a surgeon to quickly and accurately place an intraocular shunt into any quadrant of the eye and position an outflow end of the shunt into one of a variety of outflow regions without creating a scleral flap or conjunctival dissection.

Anatomy of the Eye

FIG. 1 provides a schematic diagram of the general anatomy of the eye. An anterior aspect of the anterior chamber 1 of the eye is the cornea 2, and a posterior aspect of the anterior chamber 1 of the eye is the iris 4. Beneath the iris 4 is the lens 5. The anterior chamber 1 is filled with aqueous humor 3. The aqueous humor 3 drains into a space(s) 6 deep to the conjunctiva 7 through the trabecular meshwork (not shown in detail) of the sclera 8. The aqueous humor is drained from the space(s) 6 deep to the conjunctiva 7 through a venous drainage system (not shown).

Figure 2:
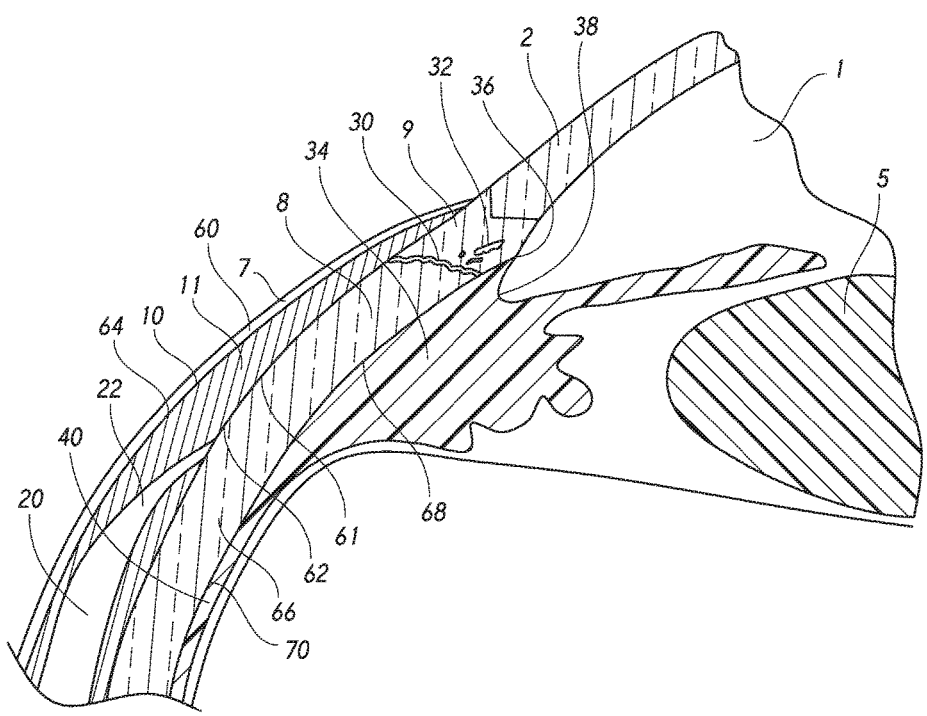
FIG. 2 is an enlarged cross-sectional diagram of the eye taken along lines 2-2 of FIG. 1.

FIG. 2 is an enlarged view of the schematic diagram of FIG. 1 taken along section lines 2-2. FIG. 2 illustrates a detail view of the sclera 8 and surrounding tissue. As shown, the conjunctiva 7 attaches to the sclera 8 at the limbus 9.

Deep to the conjunctiva 7 is Tenon's capsule 10. Tenon's capsule 10 comprises two layers (i.e., superficial and deep layers) and an intra-Tenon's adhesion space 11 that extends between the superficial and deep layers of Tenon's capsule 10. The intra-Tenon's adhesion space 11 surrounds the eye circumferentially. The intra-Tenon's adhesion space 11 can extend around the eye posterior to the limbus 9.

In the view of FIG. 2, deep to the intra-Tenon's adhesion space 11 is a rectus muscle 20. The eye has four rectus muscles (superior, inferior, lateral, and medial) that attach to sclera via a rectus tendon. FIG. 2 illustrates that the rectus muscle 20 attaches to the sclera 8 via a rectus tendon 22. For illustration purposes, the rectus tendon 22 is shown inserting onto the sclera 8. In some cases, there may not be a clear insertion point of the rectus tendon 22 onto the sclera 8, but there will be a gradual transition between the rectus tendon 22 and the intra-Tenon's adhesion space 11.

Additionally, as illustrated in FIG. 1, Tenon's capsule 10 and the intra-Tenon's adhesion space 11 is illustrated extending anteriorly relative to and superficial to the rectus muscle 20. As also shown, posterior to the rectus tendon, Tenon's capsule 10 and the intra-Tenon's adhesion space 11 also extend deep to and around the rectus muscle 20. In this region, there is a reflection of Tenon's capsule 10 and the intra-Tenon's adhesion space 11 from the rectus muscle 20 onto the globe or sclera 8. Thus, Tenon's capsule 10 and the intra-Tenon's adhesion space 11 envelop or encapsulate the rectus muscle 20.

FIG. 2 illustrates that in some locations, Tenon's capsule 10, and thus, the intra-Tenon's adhesion space 11, surrounds a rectus muscle 20. According to some embodiments of the methods disclosed herein, the intra-Tenon's adhesion space 11 can be accessed from the anterior chamber 1. Tenon's capsule 10 and the intra-Tenon's adhesion space 11 surround the eye circumferentially.

FIG. 2 also illustrates the drainage channels of the eye, including Schlemm's canal 30 and the trabecular meshwork 32, which extend through the sclera 8. Further, deep to the sclera 8, the ciliary body 34 is also shown. The ciliary body 34 transitions posteriorly to the choroid 40. Deep to the limbus 9 is a scleral spur 36. The scleral spur 36 extends circumferentially within the anterior chamber 1 of the eye.

Further, the scleral spur 36 is disposed anteriorly to the anterior chamber angle 38. Furthermore, "anterior chamber angle tissue" can refer to the eye tissue in the region extending along and/or including one or more of the cornea 2, the sclera 8, Schlemm's canal 30, the trabecular meshwork 32, the ciliary body 34, the iris 35, or the scleral spur 36.

Accordingly, for definitional purposes, the space between the conjunctiva 7 and Tenon's capsule 10 or the intra-Tenon's adhesion space 11 is referred to herein as subconjunctival space 60 (here shown as a potential space). The space between the sclera 8 and Tenon's capsule 10 or the intra-Tenon's adhesion space 11 is referred to herein as suprascleral space 61 (here shown as a potential space). Further, the space between a deep layer or surface 62 and a superficial layer or surface 64 of Tenon's capsule 10 is referred to herein as the intra-Tenon's adhesion space 11. Additionally, the space within the sclera 8 (i.e., between the superficial and deep layers or surfaces of the sclera 8) is referred to herein as intrascleral space 66 (here shown as a potential space). The space between the sclera 8 and the ciliary body 34 is referred to herein as supraciliary space 68 (here shown as a potential space). Finally, the space between the sclera 8 and the choroid 40 is referred to as suprachoroidal space 70 (here shown as a potential space). The supraciliary space 68 can be continuous with the suprachoroidal space 70.

Injectors

In accordance with some embodiments, a variety of injectors or systems known in the art may be used to perform the methods disclosed herein. In certain embodiments, deployment into the eye of an intraocular shunt can be achieved using a hollow needle or shaft configured to hold the shunt, as described herein. The needle can be coupled to an injector or be a part of the injector itself. Some of the methods disclosed herein enable a surgeon to use an injector in a "freehand" procedure (i.e., without using docking, securement, or coupling devices) to inject a shunt into the eye. However, some of the methods disclosed herein also enable a surgeon to use a "guiding" injector docking device. Optionally, the injector docking device can be temporarily affixed or secured to the eye or to the inserter itself during the procedure. Such injector docking devices can be retrofitted to existing injectors or incorporated into injector designs.

Some injectors that are suitable for placing shunts according to some embodiments include, but are not limited to, injectors described in U.S. Pat. No. 6,007,511, 6,544,249, U.S. Patent Publication No. 2008/0108933, U.S. Pat. No. 8,663,303, U.S. patent application Ser. No. 12/946,222, filed on Nov. 15, 2010, U.S. patent application Ser. No. 12/946,645, filed on Nov. 15, 2010, U.S. patent application Ser. No. 14/541,070, filed on Nov. 13, 2014, and U.S. Patent Application No. 62/170,338, filed on Jun. 3, 2015, the entire contents of each of which is incorporated by reference herein.

In some embodiments, an injector can be provided in which the injector docking device and the injector are formed unitarily, coupled with each other, or otherwise formed from a single, continuous housing or material to form a single handheld unit. Otherwise, the injector docking device can be removably coupled to the injector. For example, the injector docking device can be prepared for use with an injector, and in some embodiments as a retrofit to an existing injector.

Furthermore, in accordance with some embodiments, the injectors disclosed herein can use one, two, or more actuation mechanisms, including buttons, sliders, rotational components, and combinations thereof. For example, an injector can be configured to include two buttons, a button and a slider, two sliders, and/or rotational components. The advancement or withdrawal of a component of the injector (such as a plunger rod, needle, sleeve, or other component) can be done either through actuation of a button and/or a slider, and may be manual or use an energy stored mechanism (e.g., spring loaded actuation, electrical motor, or magnetic movement).

"Guided" Injector Docking Devices

As discussed above, some embodiments disclosed herein provide an injector docking device for maintaining, securing, or fixing a position of an injector relative to the eye during eye surgery. The injector docking device can guide or otherwise facilitate insertion of the needle into the eye when performing some embodiments of the procedures disclosed herein. The injector docking device can serve as a securement or coupling device to facilitate precise alignment or otherwise provide guided support or assistance to a deployment device or injector in placement of a shunt. For example, the injector docking device can comprise a needle or injector guidance port or bore. The injector guidance port can provide a location for the injector to be inserted in order to achieve guided precision. In some embodiments, when the injector docking device is coupled to or removably affixed to the eye, the injector guidance port can control the angle at which the needle enters the eye, the depth to which the needle penetrates, and the final location of the shunt after implantation.

Thus a "guided" delivery can be performed by creating a generally fixed spatial or geometrical relationship between the eye and the injector (and in some embodiments, having the docking device coupled to or removably affixed to the eye). This can advantageously allow the surgeon to establish a predetermined entry point for the needle on the surface of the eye, verify targeting and a pre-planned position of the shunt, and benefit from the support and guidance that the injector docking device provides to the injector as the injector is inserted into or engaged with the injector docking device. The surgeon can perform this guided procedure to advance the needle along a precise trajectory within the eye and ensure accurate placement of the shunt within the eye. As noted, in some embodiments of a guided procedure, the injector docking device is coupled to or removably affixed to the eye, using suction, frictional engagement, and/or other mechanical engagement.

FIGS. 3A-18 and 21-38C illustrate various embodiments of injector docking devices and uses thereof. In accordance with some embodiments, the injector docking device can comprise a needle support component and at least one eye-contacting surface. The needle support component can have proximal and distal portions and a longitudinal needle axis extending between the proximal and distal portions. The support component can be configured such that, when coupled to an intraocular shunt inserter, the proximal or distal portion supports the inserter to align a needle of the inserter with the longitudinal needle axis. Further, the eye-contacting surface can be disposed on the distal portion of the needle support component. The eye-contacting surface can be positionable against the eye to permit a clinician to align the device relative to an indicium or indicia of the eye thereby aligning the needle relative to the eye.

For example, FIGS. 3A-5 illustrate an embodiment of an injector docking device 72 having a body 73 and a needle support component 74 that extends from a proximal portion of the body 73 toward a distal portion thereof. A distal portion of the injector docking device 72 can comprise one or more eye-contacting surfaces 76 to facilitate alignment of the needle 92 or injector 90 relative to an eye 86. In some embodiments, the body 73 of the docking device 72 can flare outwardly from the proximal portion or needle support component 74, such that the eye-contacting surfaces 76 have a greater cross-sectional profile than the needle support component 74 of the device 72. However, in some embodiments, the body of the device can have a substantially constant cross-sectional profile, such as circular, polygonal, square, rectangular, or other non-tapering profiles. An embodiment of a device 77 having a body with a substantially constant cross-sectional profile is shown in FIG. 3B. Other than the tapering body, the features of the device 77 can be similar to those of device 72 and will not be repeated herein for brevity.

Figure 3A:
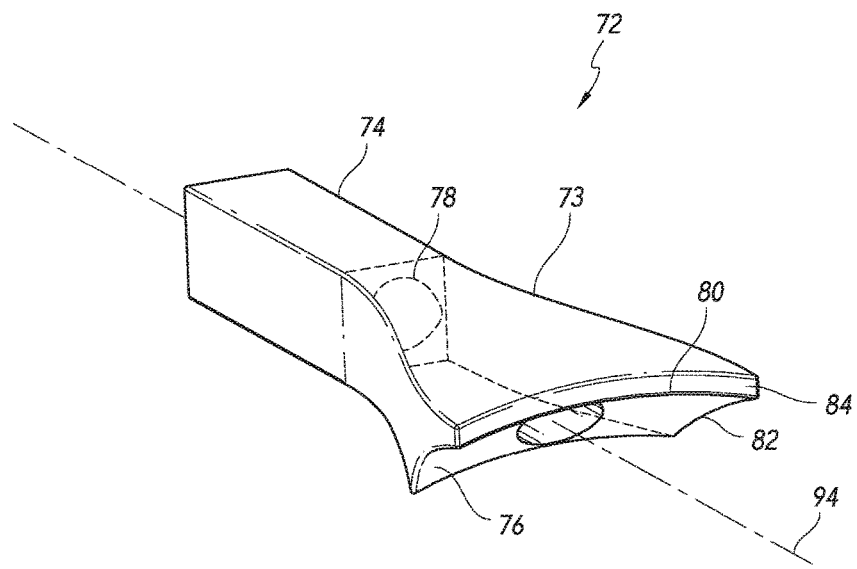
FIGS. 3A and 3B illustrate injector docking devices for use with an intraocular shunt injector, according to some embodiments.
Figure 3B:
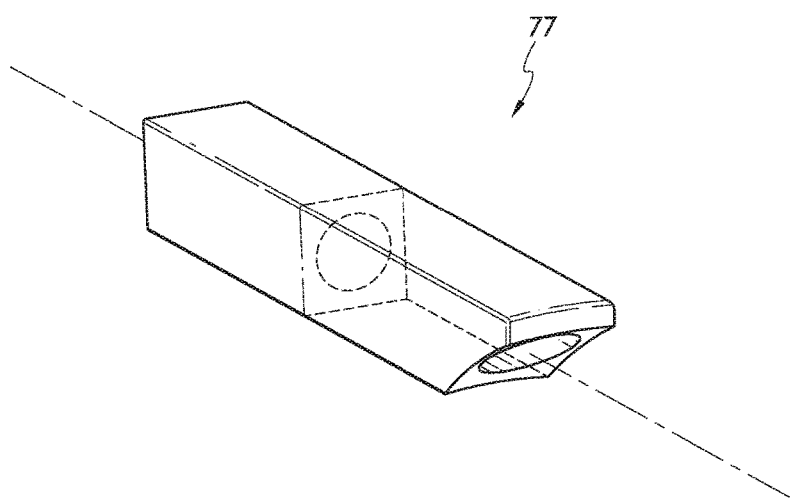
Figure 5:
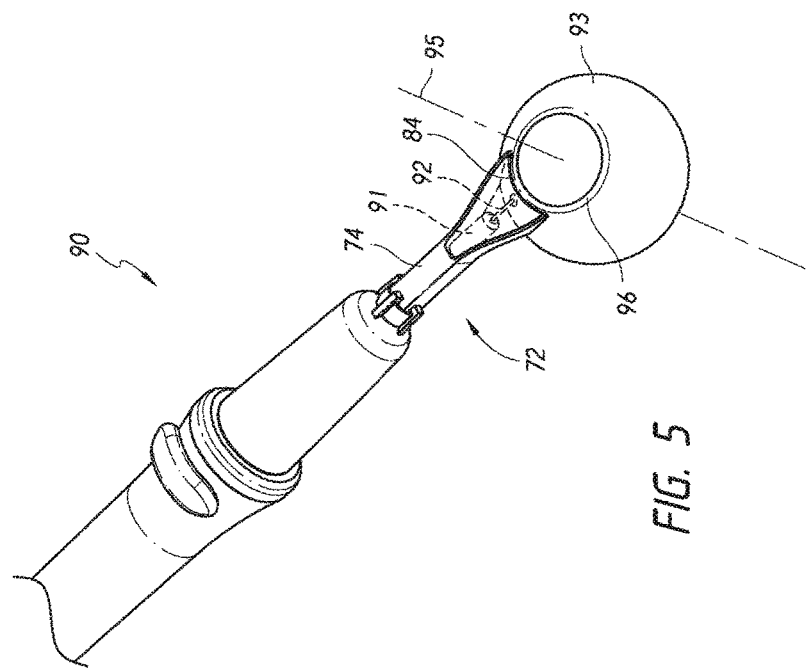
FIGS. 4 and 5 illustrate a procedure for implanting an intraocular shunt into an eye using an injector and the injector docking device shown in FIG. 3A, according to some embodiments.

As shown in FIG. 3A, the needle support component 74 can accommodate, mate with, or otherwise engage or support a needle 92 and/or a portion of an injector 90. The needle support component 74 can comprise a port 78, such as an elongate aperture, lumen, or bore that defines a needle axis 94 extending from the proximal portion toward the distal portion of the injector docking device 72. A needle 92, sleeve 91, and/or other portion of an injector 90 can be fitted into the shaft 78 from the proximal portion. In some embodiments, an inner profile of the needle support component 74 can closely match an outer profile of the needle 92, sleeve 91, or other portion of the injector 90.

The eye-contacting surface 76 can be configured for engagement against an external surface of the eye 93. FIGS. 3A-5 illustrate the eye-contacting surface 76 can comprise at least one surface configured to mate against the eye. For example, the surface can comprise a concave or arcuate surface that approximates the external surface of the eye in order to position the injector docking device 72 against the eye 93. The eye-contacting surface can be configured to facilitate alignment of the injector docking device 72 with one or more indicia of the eye 93, such as the cornea, the corneal limbus, and the pupil.

In some embodiments, the eye-contacting surface 76 can comprise a horizontal radius 80 and a vertical radius 82. In accordance with some embodiments, when the eye-contacting surface 76 is engaged against the external surface of the eye 93, the horizontal radius 80 can be oriented transverse relative to the visual axis 95 of the eye 93, and the vertical radius 82 can be oriented normal relative to the visual axis 95 of the eye 93.

In some embodiments, the horizontal radius 80 can define a curved upper edge 84 of the injector docking device 72 that can be aligned with the corneal limbus 96 to facilitate alignment of the injector docking device 72 relative to the visual axis 95 of the eye 93. In some embodiments, the vertical radius 82 can facilitate alignment of the injector docking device 72 so that the needle axis 94 intersects the target outflow region and the anterior chamber angle of the eye 93. In some embodiments, the vertical radius 82 can comprise an angle of between about 10 and 60 degrees, between about 20 and 50 degrees, between about 25 and 45 degrees, between about 30 and 40 degrees, or about 35 degrees from horizontal.

Figure 4:
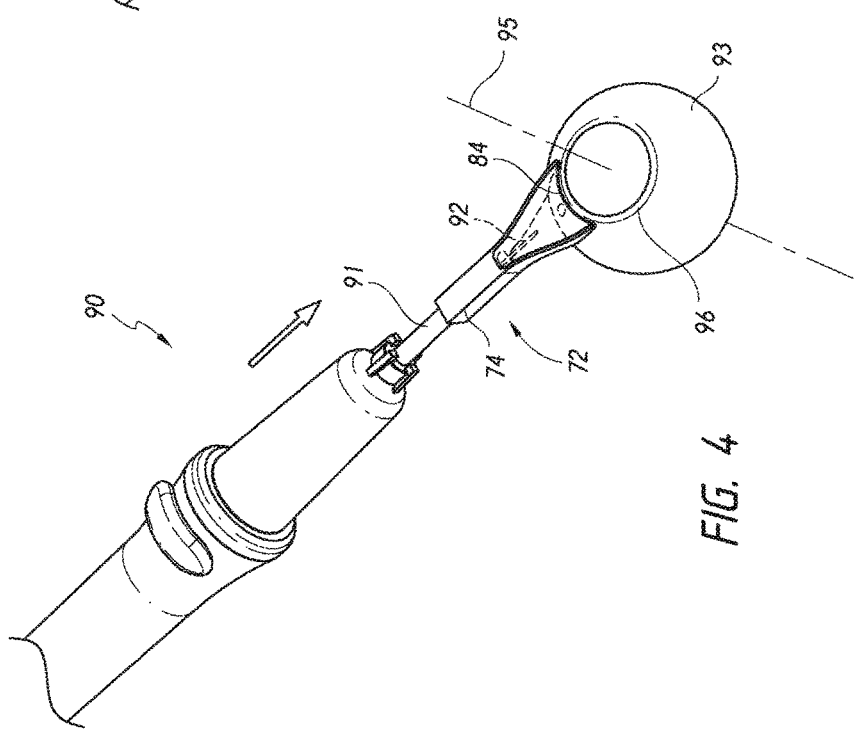
Figure 6:
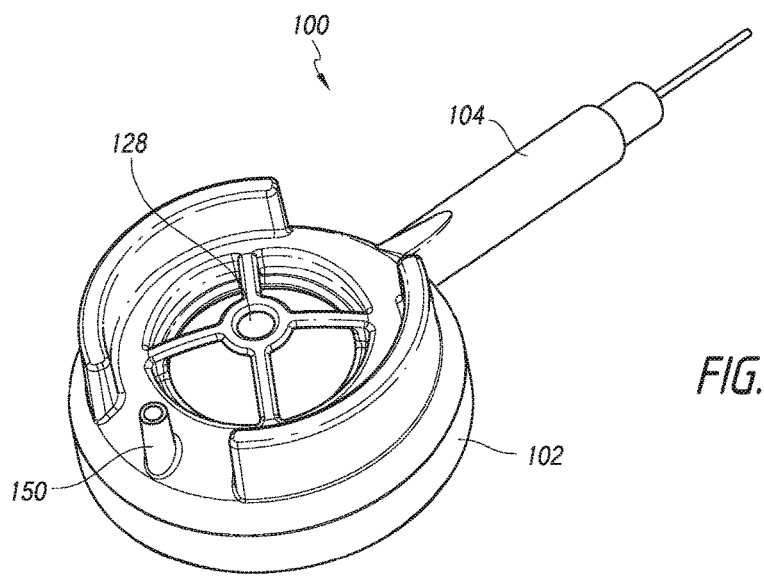
FIG. 6 is a top perspective view of an injector docking device, according to some embodiments.

Referring to FIG. 4, a needle 92, sleeve 91, or other portion of the injector 90 is permitted to extend through the needle support component 74 from the proximal portion toward the distal portion of the injector docking device 72. In this pre-injection configuration, the needle 92 does not extend beyond the distal portion of the injector docking device 72. However, referring to FIG. 5, with the eye-contacting surface 76 engaged against an external surface of the eye 93, the needle 92 can be advanced toward an injection configuration. In moving toward the injection configuration, the needle 92 can be advanced toward the eye 93 such that the needle 92 extends beyond the distal portion of the injector docking device 72 and into the eye 93. Thereafter, a shunt can be released into the eye using any of the procedures for releasing a shunt from any of the inserters disclosed or referred to herein.

In some embodiments, the injector docking device 72 can comprise a longitudinal restriction to restrict a needle 92 from travelling further than a specified distance beyond the distal portion of the injector docking device 72. The specified distance that the needle 92 is permitted to extend beyond the distal portion can be configured to correspond to the maximum distance the implant or shunt carried within the needle 92 is to be placed in the eye 93.

For example, in the injection configuration, the needle 92 can extend a preset distance beyond the injection site so that an inflow end of the shunt can be positioned in the anterior chamber while an outflow end of the shunt is positioned within, adjacent to, or ready to be repositioned within a desired outflow region. In some embodiments, the longitudinal restriction can comprise a shoulder that contacts a portion of the needle 92, sleeve 91, or other portion of the injector 90 during movement of the needle toward the injection configuration. For example, the injector docking device 72 can comprise a shoulder positioned within the lumen of the needle support component 74. Thus, the needle 92, sleeve 91, or other portion of the injector 90 moving through the needle support component 74 can be stopped by a shoulder so that the needle 92 advances only to the specified or preset distance beyond the distal portion.

In some embodiments, all or at least a portion of the injector docking device 72 can be transparent. For example, a distal portion of the injector docking device 72 can be transparent to facilitate visual alignment with an indicium of the eye, monitoring the position of the needle 92, sleeve 91, or other portion of the injector 90, or to otherwise facilitate alignment of the injector docking device 72 with the eye 93. In some embodiments, the distal portion can comprise a longer cross-sectional width than a proximal portion of the injector docking device 72. In some embodiments, the distal portion comprises a tapering cross-sectional width.

FIGS. 6-10 illustrate an embodiment of an injector docking device 100. The injector docking device 100 can comprise a body 102 and a needle support component 104 extending from the body 102. The needle support component 104 can accommodate, mate with, or otherwise engage and support a needle or a portion of an injector to facilitate alignment of the needle or injector relative to the eye.

For example, the needle support component 104 can comprise an elongate aperture or lumen into which a needle, sleeve, or other portion of an injector can be fitted. In some embodiments, an inner profile of the needle support component 104 can closely match an outer profile of the needle, sleeve, or other portion of the injector.

The body 102 can comprise an eye-contacting portion that permits the body 102 to be positioned against an external surface of the eye. The eye-contacting portion of the body 102 can comprise one or more prongs, pads, semi-circular structures, circular structures, annular structures, semi-annular structures, semi-spherical structures, or spherical structures, and can have concave and/or convex shapes for mating against one or more portions of the eye. In some embodiments, the body 102 can comprise a scleral portion 106 and a corneal portion 108.

Figure 7:
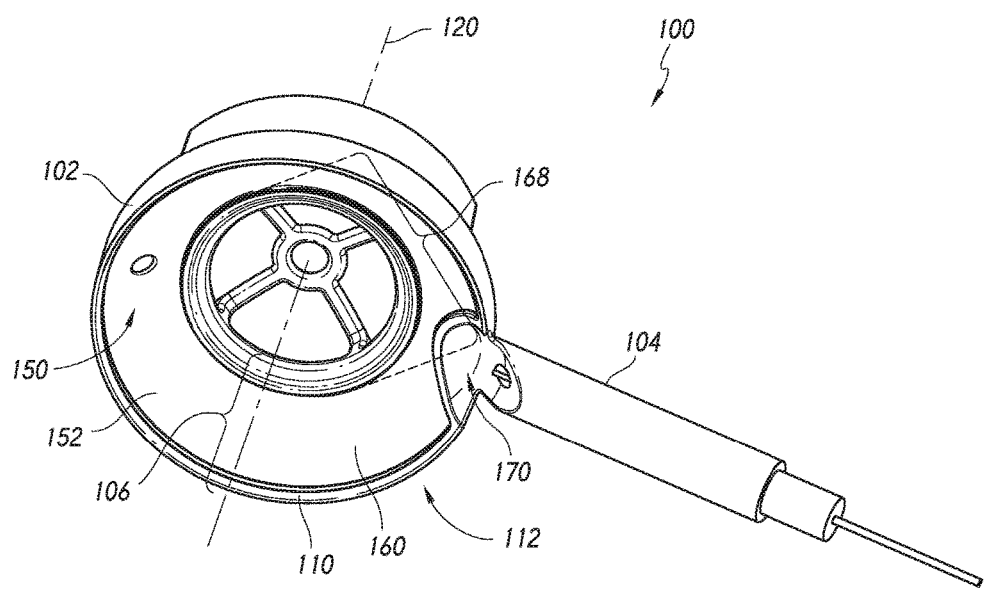
FIG. 7 is a bottom perspective view of the injector docking device of FIG. 6.

Further, as shown in FIG. 7, the body 102 can comprise an eye-contacting portion 110 formed on a first side 112 of the body 102. The eye-contacting portion 110 can extend about a central axis 120 of the body 102. Further, the needle support component 104 can comprise a needle or injector guidance port or bore 122 into which a needle of a delivery device can be passed.

In accordance with some embodiments, the central axis 120 can be intended to align with a straight ahead line of sight of the eye (i.e., a central axis of the eye passing through a center of the cornea). The injector guidance port 122 can define a needle axis 124 extending transversely relative to the eye-contacting portion 110. In some embodiments, the needle axis 124 extends transversely relative to the central axis 120. For example, the needle axis 124 can extend relative to the central axis 120 at an angle of between about 45 degrees and about 90 degrees, between about 60 degrees and about 80 degrees, between about 65 degrees and about 75 degrees, or about 70 degrees.

The relative angle between the central axis 120 and the needle axis 124 can be determined based on the desired outflow region that is being targeted by the injector docking device. Generally, a more anterior or superficial target outflow region can have a higher relative angle compared to a more posterior or deep target outflow region. For example, when targeting an outflow region at about where the rectus tendon 22 inserts onto the sclera 8, the relative angle between the central axis 120 and the needle axis 124 can be higher than when targeting an outflow region posterior to or deep to this location (e.g., when targeting an outflow region, such as the suprachoroidal space). The relative angle between the central axis 120 and the needle axis 124 can also be selected based on the desired target outflow region and the required "entrance angle" (i.e., the relative angle between the needle axis 124 and a surface of the eye).

The injector docking device 100 can include a targeting ring or alignment aperture 128 to facilitate positioning of the injector docking device 100 onto the eye. The targeting ring 128 can comprise a through hole extending from an upper surface of the injector docking device 100 there through to the eye-contacting portion 110. The targeting ring 128 can allow a surgeon to look therethrough to see the eye and visually confirm the position of the injector docking device 100 relative to the eye. For example, the targeting ring 128 can be used to see the cornea and roughly center the injector docking device 100 on the cornea. The targeting ring 128 can be configured to permit the surgeon to see any of the indicia of the eye, such as the cornea, the corneal limbus, and the pupil, to name a few.

FIGS. 6-10 illustrate that the body 102 can have a spherical inner contour along the eye-contacting portion 110 thereof. The eye-contacting portion 110 can extend fully or partially about the central axis 120. As shown in FIGS. 6-10, the eye-contacting portion 110 extends fully about the central axis 120.

The eye-contacting portion 110 can comprise one or more regions configured to contact specific physiological structures of the eye. For example, the eye-contacting portion 110 can comprise an outer section 130 and an inner section 132. The outer section 130 can be configured to overlie sclera of the eye while the inner section 132 can be configured to overlie or abut the corneal limbus and/or the cornea of the eye.

The inner section 132 of the injector docking device 100 can be configured to contact the eye adjacent to the corneal limbus in order to engage the eye, create a seal against the eye, or otherwise facilitate securement of the eye-contacting portion 110 to the eye. For example, the inner section 132 can be positioned posterior to, anterior to, or against the corneal limbus. In some embodiments, the inner section 132 of the injector docking device 100 can have an outer diameter 140 of between about 9 mm and about 20 mm, between about 11 mm and about 18 mm, between about 13 mm and about 16 mm, or about 15 mm. Further, the inner section 132 can have an inner diameter 142 of between about 9 mm and about 14 mm, between about 10 mm and about 13 mm, between about 10.5 mm and about 12 mm, or about 11 mm, 11.5 mm, 12 mm, or 12.5 mm.

Figure 10:
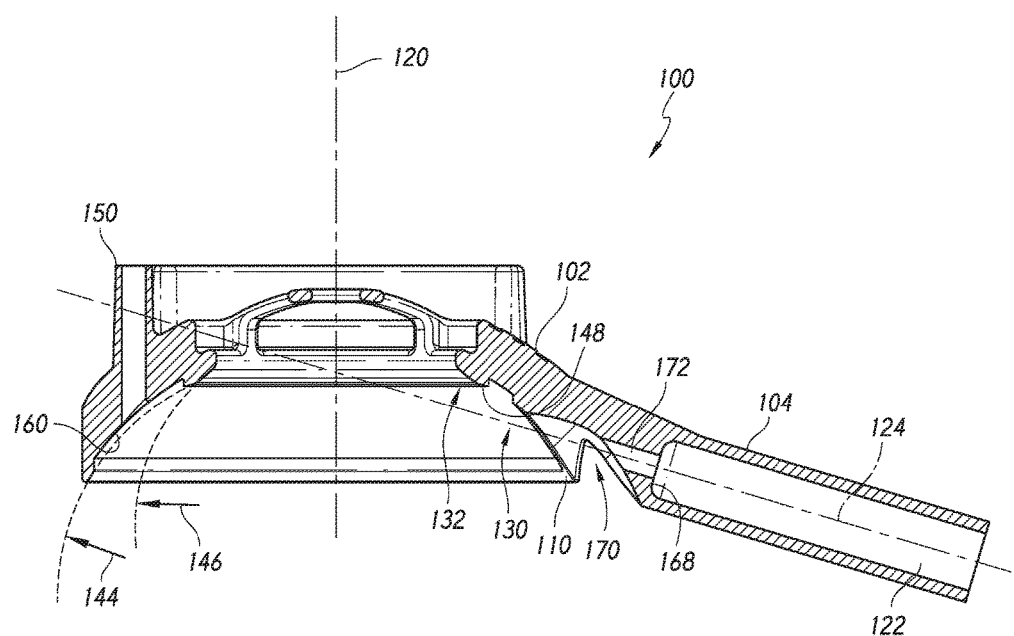
FIG. 10 is a side, cross-sectional view of the injector docking device of FIG. 6 taken along lines 10-10 of FIG. 6.

As shown in FIG. 10, the eye-contacting portion 110 of the injector docking device 100 can have two different radii of curvature that can allow the ring to mate to the sclera and to mate to the cornea. This double-radius docking allows for self-centering of the docking device 100 during the application of suction. Any slight misalignment during the suction application may otherwise cause the device 100 to shift such that the two different suction radius sections create an optimal symmetrical shift. Alternatively or additionally, the cross hair and ring feature 128 in FIG. 9 can permit independent center verification or alignment by centering its features visually to the patient's pupil. For example, the outer section 130 can have a radius of curvature 144 of between about 11 mm and about 14 mm, between about 11.6 mm and about 13.4 mm, between about 11.9 mm and about 12.9 mm, or about 12.4 mm. In some embodiments, the radius of curvature 144 can approximate the radius of curvature of the sclera of the eye in order to better mate against the sclera. The radius of curvature 144 can fall within acceptable ranges of the radius of curvature of the sclera, as known in the art or measured using known methods. See, for example, Measurement of Anterior Scleral Curvature Using Anterior Segment OCT, Choi et al., Optom Vis Sci. 2014 July; 91(7):793-802. doi: 10.1097/OPX.0000000000000298, the entirety of which is incorporated herein by reference.

Further, the inner section 132 can have a radius of curvature 146 of between about 6 mm and about 10 mm, between about 7 mm and about 9 mm, between about 7.6 mm and about 8.2 mm, or about 7.8 mm. The radius of curvature 142 can fall within acceptable ranges of the radius of curvature of the cornea, as known in the art or measured using known methods. See, for example, Curvature Analyses of the Corneal Front and Back Surface, Vojnikovic et al., Coll. Antropol. 37 (2013) Suppl. 1:93-96, the entirety of which is incorporated herein by reference.

In some embodiments, the radii of curvature 144, 146 can also vary from a posterior region and anterior region thereof. For example, the radii of curvature 144, 146 can increase in an anterior direction. Such variability can advantageously allow the outer section 130 and the inner section 132 to better mate against the sclera and cornea, respectively.

In addition, the intersection of the radii of curvature 144, 146 can form a ridge 148 that can mate against the corneal limbus of the eye. Further, the ridge 148 can advantageously further encourage the concentricity or alignment of the injector docking device 100 to the cornea.

However, some embodiments can be created in which the inner and outer sections 130, 132 have a common radius of curvature and a ridge is provided at an intersection of the inner and outer sections 130, 132. In such embodiments, the ridge can extend inwardly toward a central axis of the device and have a height of less than about 1 mm, about 1 mm, about 2 mm, or about 3 mm. The ridge can extend at least partially or entirely around a circular path at the intersection of the inner and outer sections 130, 132.

The injector docking device 100 can use suction and/or one or more frictional components, such as spikes or other engagement features to couple the injector docking device to the eye. In some embodiments, the injector docking device 100 can comprise a vacuum or suction feature that allows the injector docking device 100 to engage the eye. For example, the injector docking device 100 can comprise a vacuum port or bore that is in fluid communication with at least one vacuum pocket or channel to aid in engagement between the eye and the injector docking device 100. The vacuum port can be used to provide vacuum pressure to the injector docking device using a simple syringe, a gravity tube, or electric pump.

For example, the injector docking device 100 can comprise a scleral vacuum pocket or channel and/or a corneal vacuum pocket or channel. In some embodiments, the vacuum port can be coupled to both the scleral vacuum pocket and the corneal vacuum pocket such that a vacuum pressure can be applied via the vacuum port to both pockets simultaneously. However, the vacuum port can also be coupled to only the scleral vacuum pocket or only the corneal vacuum pocket (e.g., if only one type of pocket is present). In some embodiments, the scleral vacuum pocket and the corneal vacuum pocket can have independent vacuum ports for independently applying vacuum pressure or applying different magnitudes of vacuum pressure.

FIGS. 6-10 illustrate that the injector docking device 100 can comprise a scleral vacuum pocket or channel 160. The scleral vacuum pocket 160 can extend at least partially along the eye-contacting portion 110 of the injector docking device 100. For example, in some embodiments, the scleral vacuum pocket 160 can be formed along the outer portion 130 of the injector docking device 100. Further, the depth and width of the scleral vacuum pocket 160 can define the maximum deformation of the sclera when a vacuum pressure is applied. In some embodiments, the scleral vacuum pocket 160 can have a depth of between about 0.2 mm and about 1 mm, between about 0.3 mm and about 0.7 mm, or about 0.5 mm. Further, in some embodiments, the scleral vacuum pocket 160 can have a width of between about 2 mm and about 5 mm, between about 3 mm and about 4 mm, or about 3.5 mm.

In some embodiments, the injector docking device 100 can comprise a secondary corneal vacuum pocket or channel that extends along a corneal portion 108 of the injector docking device 100. The corneal vacuum pocket (not shown) can aid in suction and can be used in combination with the scleral vacuum pocket 160 or alone, instead of the vacuum pocket 160. Similarly to the scleral vacuum pocket 160, the depth and width of the corneal vacuum pocket can define the maximum deformation of the cornea when a vacuum pressure is applied. In some embodiments, the corneal vacuum pocket can have a depth of between about 0.2 mm and about 1 mm, between about 0.3 mm and about 0.7 mm, or about 0.5 mm. Further, in some embodiments, the cornea vacuum pocket can have a diameter of between about 10 mm and about 12 mm, between about 10.5 mm and about 11.75 mm, or about 11.5 mm.

Additionally, in some embodiments that include both the scleral vacuum pocket 160 and a corneal vacuum pocket, the corneal vacuum pocket may be fluidly interconnected to the vacuum source or vacuum port 150 of the scleral vacuum pocket 160. However, a separate vacuum source or vacuum port can also be used. Further, when the injector docking device 100 comprises only a corneal vacuum pocket, a vacuum port can be fluidly interconnected with the corneal vacuum pocket and be positioned in a central location along an outer surface of the body 102 of the injector docking device 100.

In accordance with some embodiments, injector docking device 100 can therefore provide suction on and/or otherwise engage the cornea and/or below corneal limbus (e.g., along the sclera). As noted, an alternative to suction is to provide a frictional or grippy surface, such as ridges, hooks, or spikes that may penetrate or otherwise engage the conjunctiva. Such a surface can enable the surgeon to contact the injector docking device against the eye and achieve suitable frictional and/or mechanical engagement with the eye. However, suction and mechanical engagement can both be used in some embodiments.

In use, the targeting ring 128 can be used to center the injector docking device 100 on the cornea before applying suction and/or mechanically engaging the injector docking device 100 with the eye. Thereafter, suction can be applied with a simple syringe, a gravity tube, or electric pump. The vacuum pressure applied to the eye can be strong enough to couple the injector docking device 100 to the eye in order to allow a surgeon to move the eye using the injector docking device 100. Further, in some embodiments, the vacuum pressure can be adjustable. For example, suction can be adjusted by adjusting the negative pressure and/or the surface area covered by vacuum pocket(s). Suction pressure and surface area are accounted for in the formula: $P=F/A$, $F=P*A$. As such, increasing the surface area can directly increase the suction force.

As noted above, the injector docking device 110 can serve as a precise alignment guide for placement of the deployment device or injector. Accordingly, the injector docking device can comprise a needle support 104 having the injector guidance port 122. The injector guidance port 122 provides a location for the injector to be inserted with guided precision. The injector guidance port 122 can control the angle the needle enters the eye based on the angle of the needle axis 124 relative to the central axis 120. Further, the injector guidance port 122 can have a depth or length that limits the depth to which the needle or shaft of the injector penetrates, as well as the final location of the shunt after implantation. The dimensions of the injector guidance port 122 can be based at least in part on the actuation or movement of the injector in advancing and releasing the shunt. For example, the injector guidance port 122 can comprise a shoulder 168 against which a distal end of a sleeve or component of the injector can be abutted in order to limit distal advancement of the injector relative to the injector guidance port 122. As such, advancement or travel of the needle and shunt can be defined by the actuation of the injector (including the movement of the needle and/or plunger of the injector).

In some embodiments, the injector guidance port 122 of the injector docking device 100 be longer and much larger in diameter than a needle bore 172 thereof (e.g., a diameter of the injector guidance port 122 can be about 5, about 6, about 7, about 8, about 9, about 10, about 11, or about 12 times as large as a diameter of the needle bore 172). Further, the diameter of the needle bore 172 can be much larger in diameter than a needle of the injector (e.g., twice as large) in order to ensure that when inserting the needle into the needle bore 172, the needle does not contact the sidewall of the injector guidance port 122 or the needle port 172 (which can damage or dull the needle).

In accordance with some embodiments, the injector docking device 100 can also comprise a bleb or ballooning pocket 170. For example, in accordance with some embodiments of the methods disclosed herein, when a bleb is created to facilitate placement of an outflow end of the shunt within a target outflow region defined at least in part by the bleb, the bleb pocket 170 can be positioned over the bleb. The bleb pocket 170 can be configured to limit the expansion of the bleb to an optimal shape before the needle enters the conjunctiva. Further, the bleb pocket 170 can enable excess ballooning of the bleb to be pushed below or outside the injector docking device 100. However, as discussed further herein, some embodiments of the procedure can be performed without creating a bleb or otherwise ballooning the target outflow region prior to injecting the shunt into the eye. Accordingly, some embodiments of the injector docking devices disclosed herein can be formed without a bleb pocket 170 incorporated into the body 102 of the injector docking device 100.

Advantageously, the injector docking device 100 can potentially be oriented in all four quadrants of the eye (nasal superior, nasal inferior, temporal superior, or temporal inferior). The surgeon can therefore avoid problem areas of a patient's eye, such as locations of previously failed surgeries (e.g., where there may exist scarred-down tissue or failed Trabeculectomy areas). Further, the surgeon can advantageously assess which quadrants are available by rotating the patient's eye and assess access to the injector guidance port depending on anatomical features of the patient.

"Guided" Ab Externo Implantation Methods

As discussed herein, new methods for ab externo implantation of a shunt can provide a simple and safe procedure that can be performed in an office setting. These new ab externo approaches can use an injector docking device and can enable an outflow end of a shunt to be deployed under/into any of a variety of outflow regions without making a scleral flap or otherwise requiring a conjunctival dissection. A surgeon can inject a fluid ab externo into the target outflow region to create a bleb—before and/or after implantation of the shunt—in order to facilitate positioning of an outflow end of a shunt within the target outflow region. The outflow end of the shunt can be positioned in the subconjunctival space or over-Tenon's space (between Tenon's and conjunctiva), the suprascleral or sub-Tenon's space (between Tenon's and sclera), the intra-Tenon's space (between layers of Tenon's capsule, or in the intra-Tenon's adhesion space), the choroidal and suprachoroidal space, the intrascleral space (between layers of sclera), Schlemm's canal, the vitreous space, the episcleral vein, or the supraciliary space.

Some embodiments of the methods and devices disclosed herein allow a surgeon to use an injector docking device to perform a "guided" procedure in which the injector docking device creates a generally fixed spatial or geometrical relationship between the eye and the injector. This fixed relationship allows the surgeon to use the injector docking device to establish or assist in defining a predetermined entry point for the needle on the surface of the eye and benefit from the support and guidance that the injector docking device provides to the injector as the injector is inserted into or engaged with the injector docking device. The surgeon can perform this guided procedure to advance the needle along a precise trajectory within the eye and ensure accurate placement of the shunt within the eye.

Figure 11:
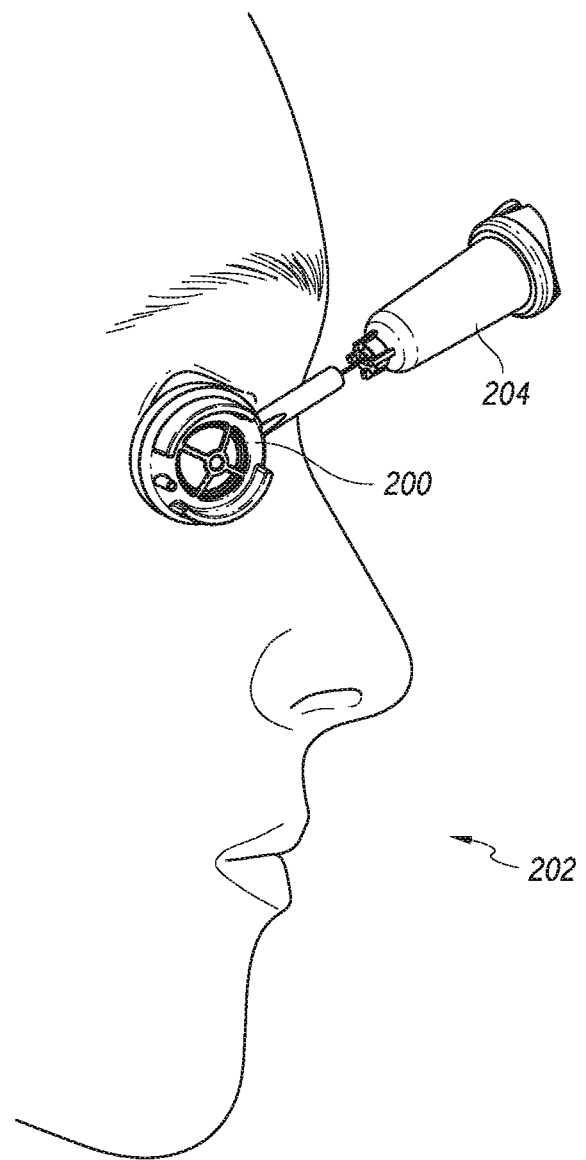
FIGS. 11-20 illustrate a procedure for implanting an intraocular shunt into an eye using an injector and the injector docking device of FIG. 6, according to some embodiments.

FIGS. 11-20 illustrate the steps of a procedure for ab externo implantation of a shunt, according to some embodiments. FIG. 11 illustrates placement of an injector docking device 100 onto an eye of a patient 202. Further, an injector 204 is shown as being inserted into an injector guidance port of the injector docking device 100. FIG. 11 shows that the injector guidance port of the injector docking device 100 is positioned in a superior nasal position. However, as noted above, the injector docking device can be positioned such that the injector guidance port is oriented in any of a variety of directions so that the surgeon can insert the injector into a variety of different quadrants of the eye, including the superior temporal, inferior temporal, and inferior nasal. Further, depending on the placement or injector docking device configuration, the surgeon can position the injector so that the needle accesses the anterior chamber of the eye at a variety of different angles.

Figure 12:
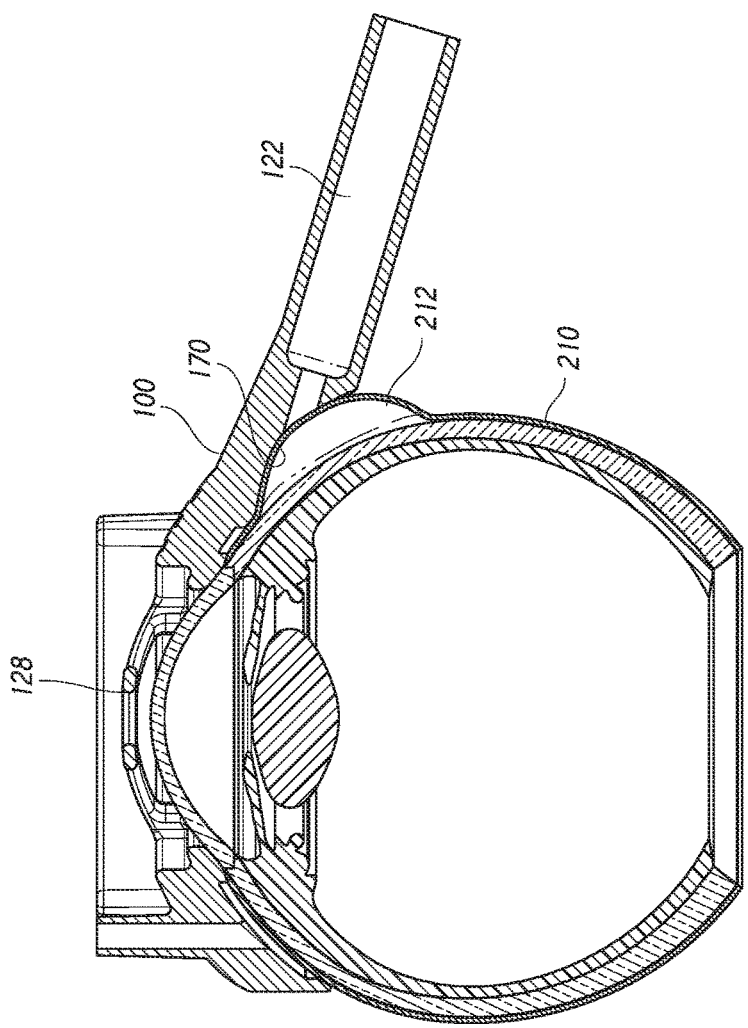

FIG. 12 illustrates an initial placement step of the injector docking device 100 onto an eye 210. Prior to placement of the injector docking device 100 onto the eye 210, a bleb 212 can be formed. The bleb 212 can be formed by an injection prior to the placement of the injector docking device 100. The injection can comprise a BSS, a viscoelastic, an antimetabolite, a drug-eluting solution, water, and/or a combination thereof. After the bleb 212 is formed, the injector docking device 100 can be positioned against the eye, with the bleb pocket 170 positioned over the bleb 212.

Accordance with some embodiments, the formation of the bleb or ballooning of a target outflow region can be performed by positioning a bevel of a small needle (e.g., 27 G or 30 G) within the target outflow region space or potential space, and slowly injecting fluid into the space. For example, by placing the bevel of the needle close to sclera, anterior to Tenon's layer and between conjunctiva and sclera, the conjunctiva can be ballooned away from the sclera. Also, for example, if the bevel of the needle is positioned within Tenon's capsule or within intra-Tenon's adhesion space, fluid can be injected into and absorbed by the Tenon's capsule. Various other spaces or potential spaces can be ballooned to facilitate placement therein of an outflow end of a shunt, according to some embodiments, thus creating a desired target outflow region.

Optionally, the injector docking device 100 can be moved to its final position using the targeting ring 128 to verify alignment with anatomical structures of the eye, such as the cornea or pupil. Further, in some embodiments, after the injector docking device 100 is in its final position, suction can be applied using one or more of the scleral vacuum pocket or the corneal vacuum pocket. Thereafter, the injector can be inserted and readied for actuation. In some embodiments, the injector can comprise a 27 G needle or other suitable size.

Figure 13:
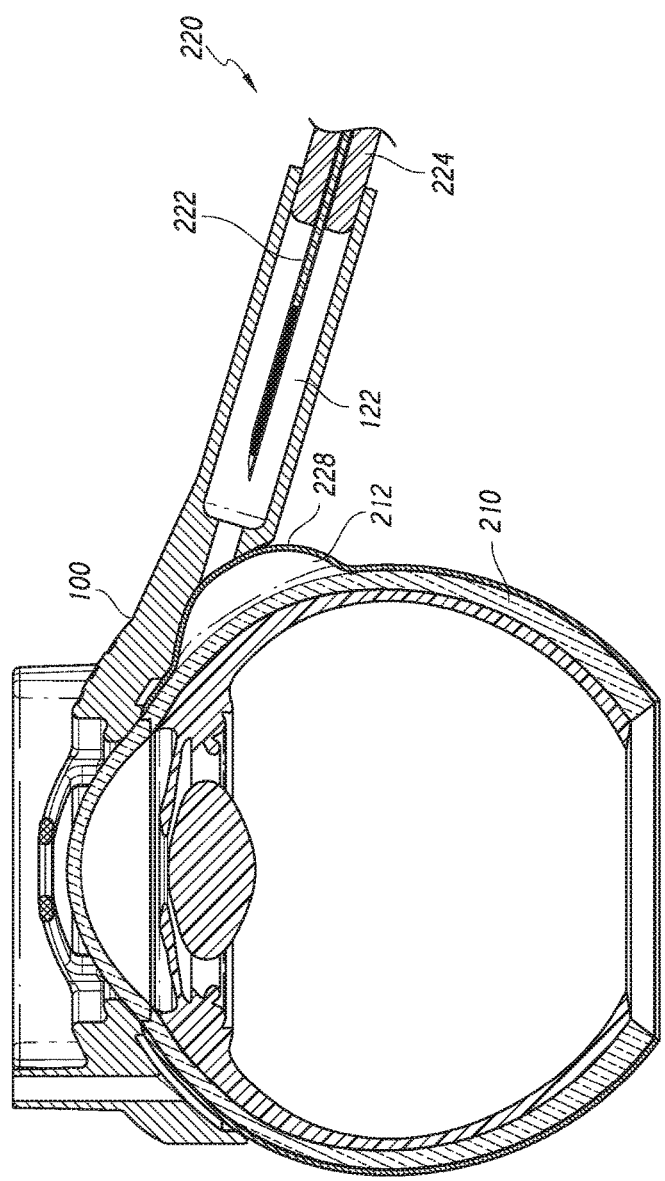

When placing the injector into the injector guidance port 122, the needle of the injector can be in an exposed position or withdrawn into a sleeve or housing of the injector so that the needle is not exposed. For example, as shown in FIG. 13, an injector 220 can be inserted into the injector guidance port 122 in a configuration in which a needle 222 of the injector 220 is exposed or extends distally beyond a sleeve 224 of the injector 220. In this manner, the needle 222 can already be out so surgeon feels it directly when simultaneously advancing the injector 220 further into the injector guidance port 122 and the needle 222 into the bleb 212.

Figure 14:
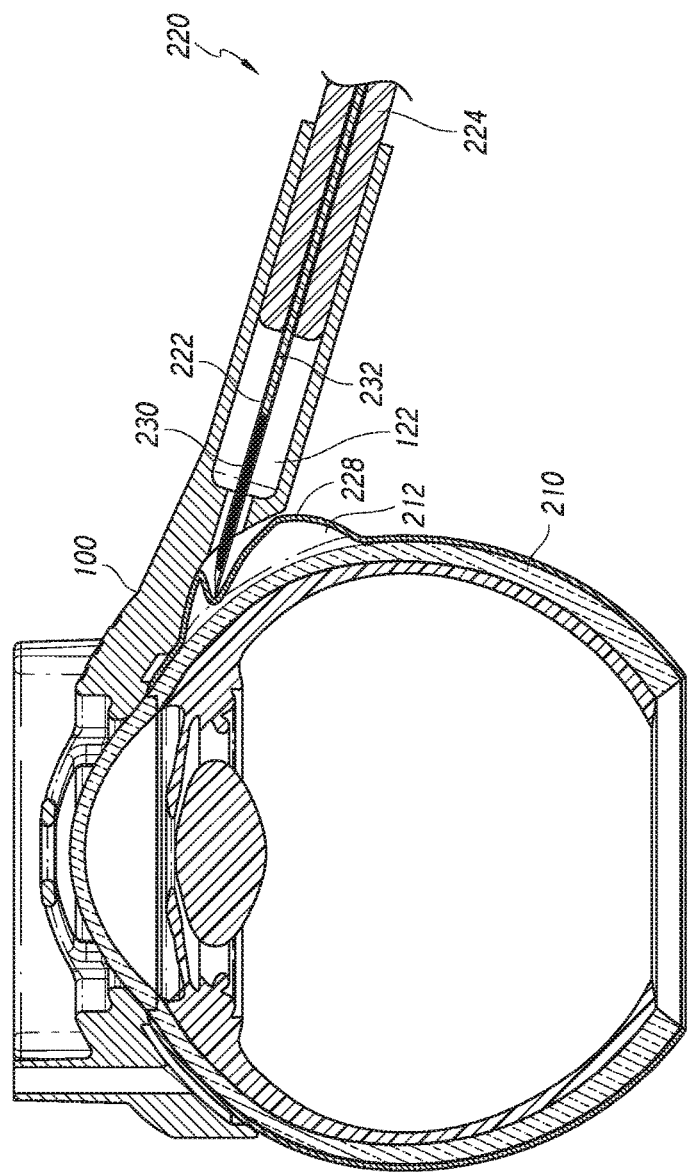

Referring now to FIG. 14, as the needle 222 is advanced, the needle 222 may collapse conjunctiva to sclera before piercing. The shunt 230 and the pusher rod 232 may travel forward with the needle 222. For example, as shown in FIG. 15, the shunt 230 and the pusher rod 232 may travel forward with the needle 222 and penetrate conjunctiva 228 of the eye 210 until reaching to a final position for the shunt 230, which is also a stop position for the sleeve 224 abutting the shoulder 168 of the injector guidance port 122.

In some instances, as the needle penetrates the eye and is advanced through the bleb into the target outflow region, the superficial layer of the target outflow region (e.g., the conjunctiva 228 or bleb 212) may be pushed down, compressed, or deflated. For example, during advancement of the needle 222 into the bleb 212, the bleb 212 may be partially or fully pushed down or compressed (e.g., against the sclera) locally by the needle 222. In the case that the superficial layer of the target outflow region is pushed down, compressed, or deflated, retraction of the needle 222 can pull back or cause the superficial layer of the target outflow region (e.g., the conjunctiva 228 or bleb 212) to rebound to its previously inflated size (e.g., as shown in FIG. 12), thus ensuring that the proximal or outflow end of the shunt 230 is positioned deep to the superficial layer of the target outflow region (e.g., the conjunctiva 228 or bleb 212).

In some embodiments, the "pull back" of the needle 222 or rebounding of the bleb 212 can be further facilitated by a "top-off" injection of fluid into the bleb 212 or target outflow region after the needle 222 has been fully inserted into the eye 210. For example, FIG. 15 also illustrates that after deflation of the bleb 212, a surgeon can add additional fluid to reinflate the bleb 212. This additional fluid can be injected using the needle 222 after the shunt is ejected from the needle 222 or by using a separate needle.

Figure 15:
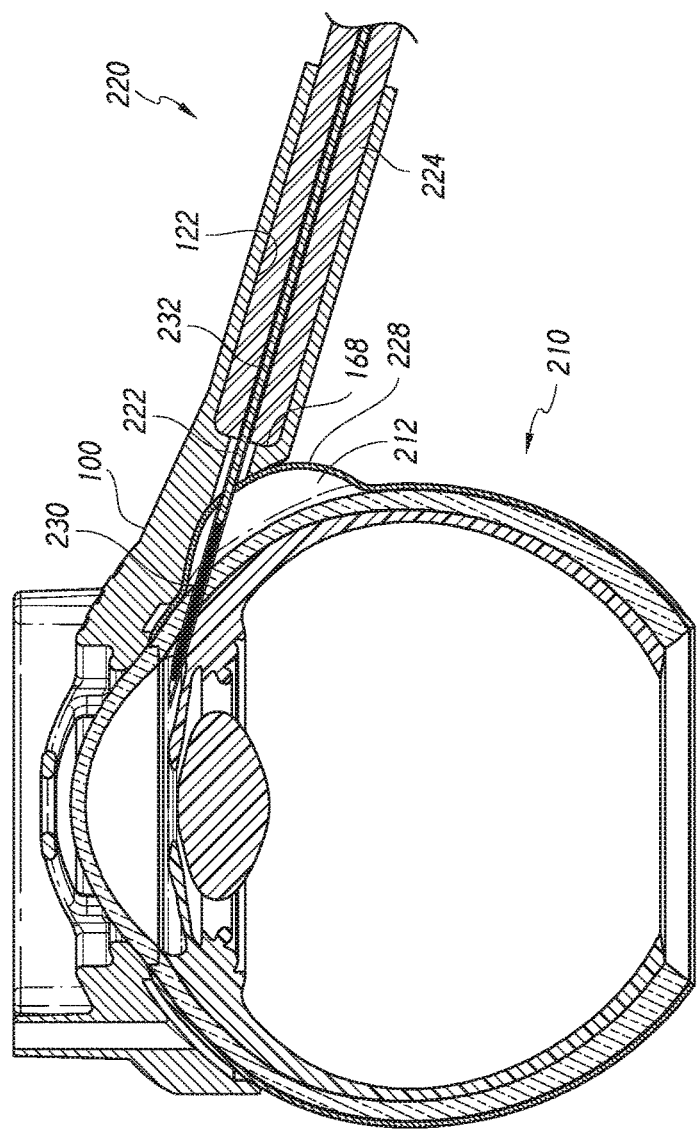
Figure 16:
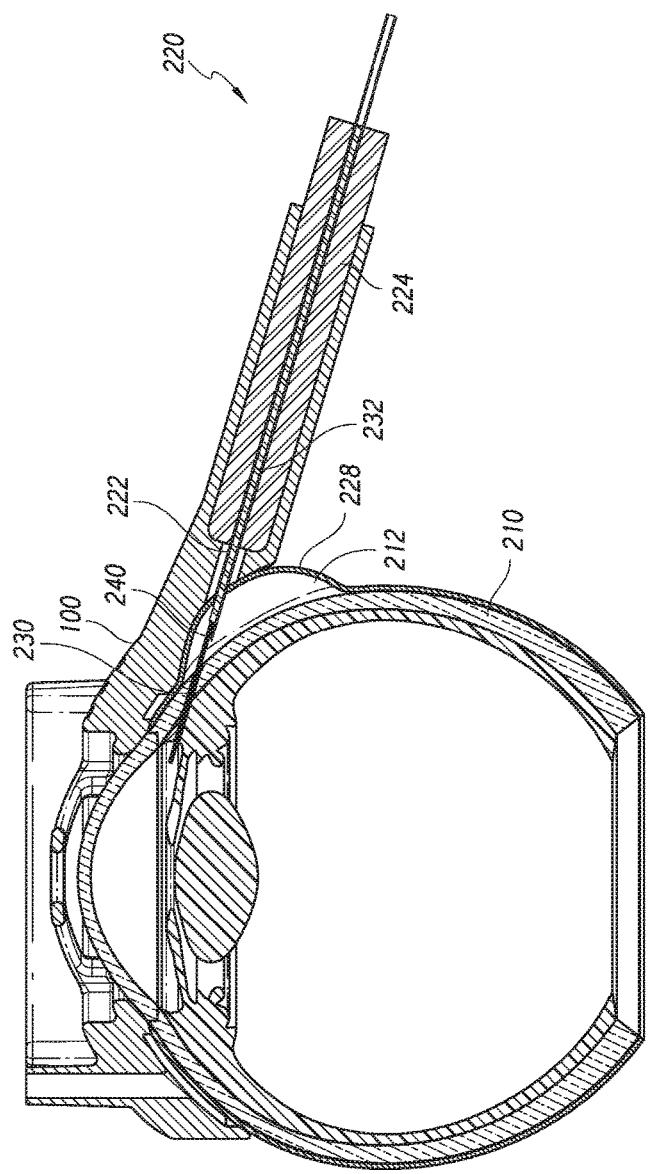
Figure 17:
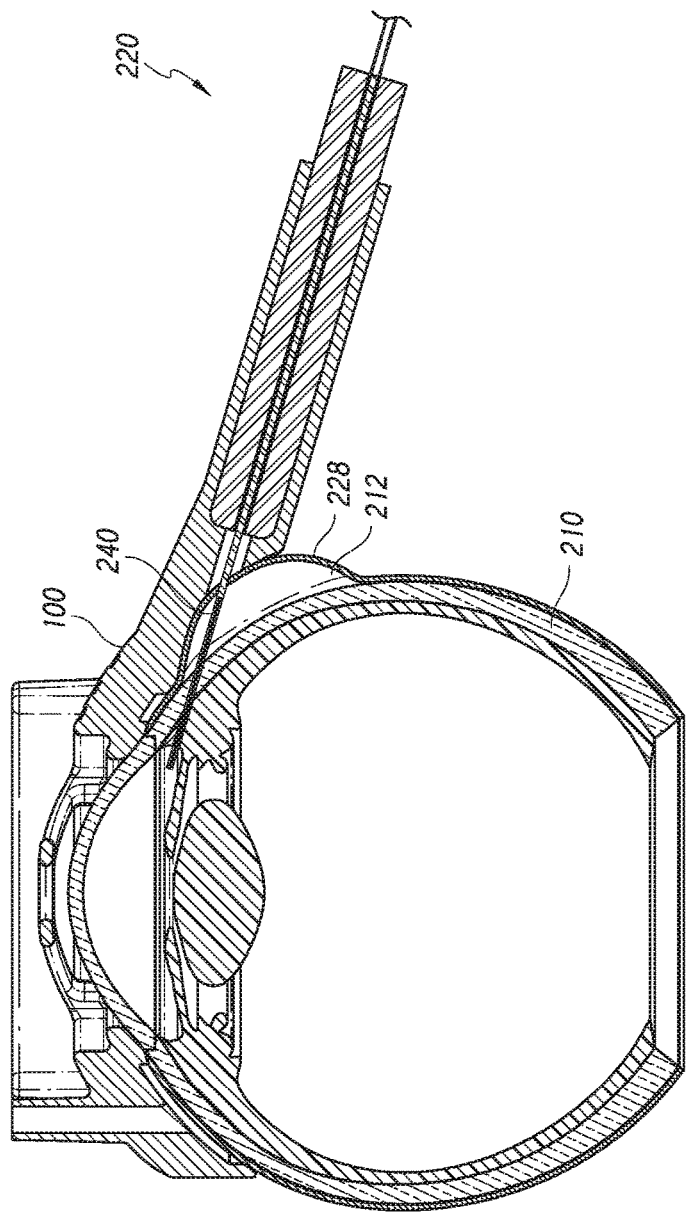

Referring to FIGS. 15-17, the shunt 230 can be advanced to or positioned at a final target position within the eye 210. If the shunt 230 is not already positioned at the distal end of the needle 222 (e.g., during advancement of the needle 222 is illustrated in FIGS. 14 and 15), the shunt 230 can be advanced by the actuation of the pusher rod 232 until reaching a position as illustrated in FIG. 15.

Once the shunt 230 is in its final position, the needle 222 can be partially retracted while position of shunt 230 is maintained by the pusher rod 232. Further, FIGS. 16 and 17 illustrate that the proximal withdrawal of the needle 222 can serve to pull the superficial layer of the target outflow region (e.g., the conjunctiva 228) superficial to an outflow end 240 of the shunt 230. Proximal withdrawal of the needle 222 can therefore pull back the superficial layer of the target outflow region due to friction, but if friction not enough, additional fluid can be injected, as discussed above.

Figure 18:
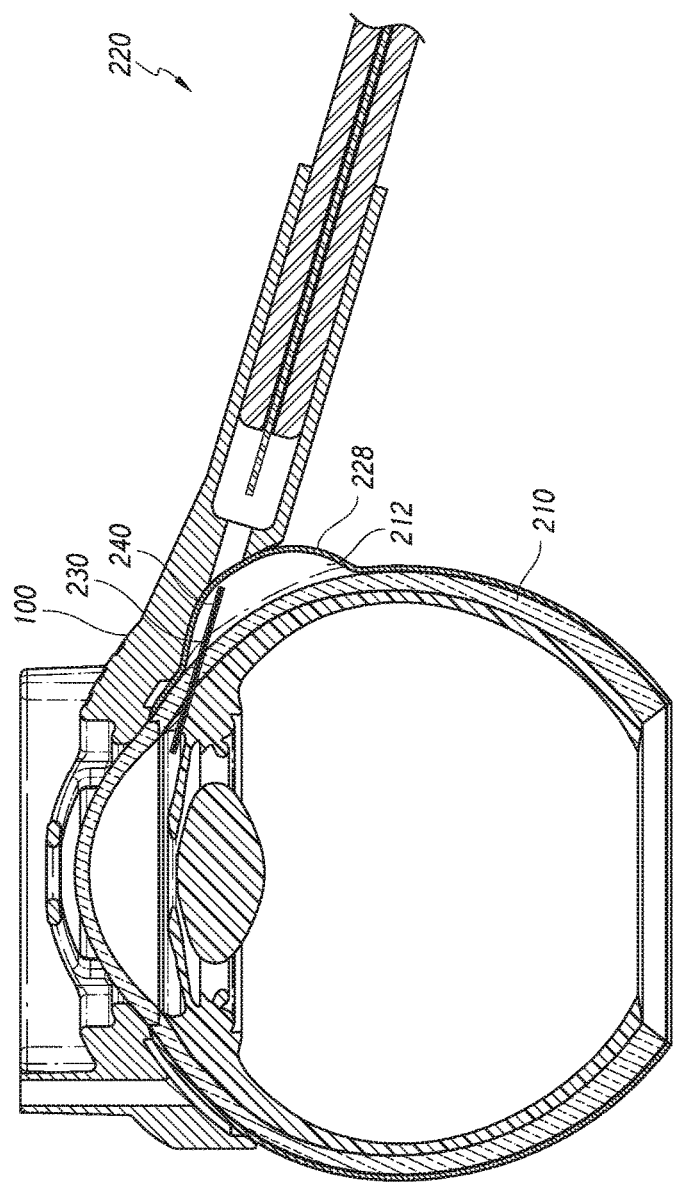
Figure 19:
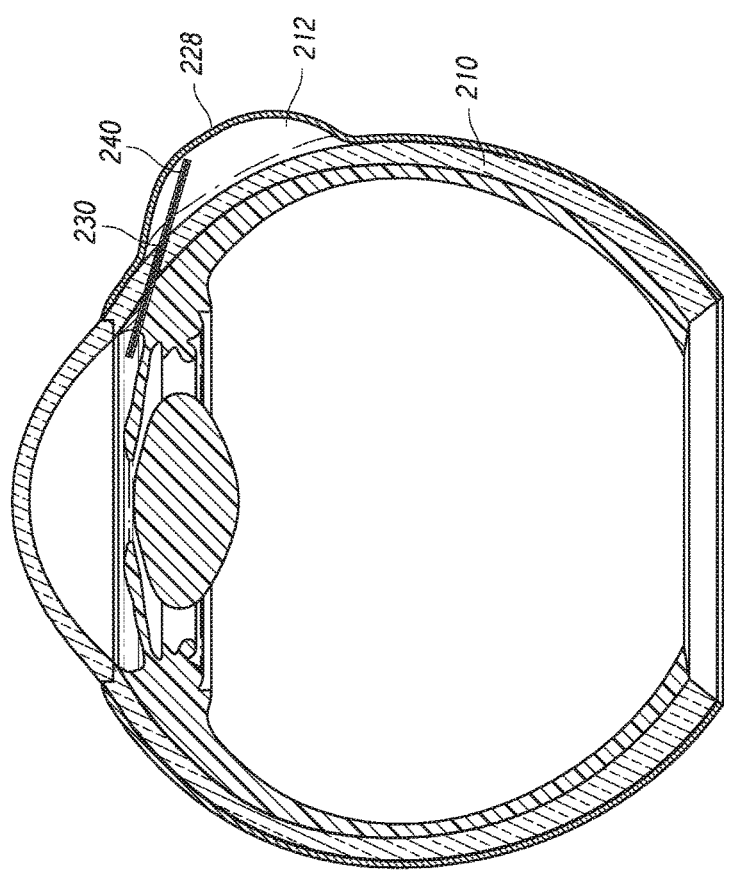

After the needle 222 has been fully withdrawn (as shown in FIG. 17), the pusher rod 232 and injector 220 can be retracted and removed, as shown in FIG. 18. After the pusher rod 232 fully retracted from the bleb 212, the injector docking device 100 can be removed, as shown in FIG. 19.

Figure 20:
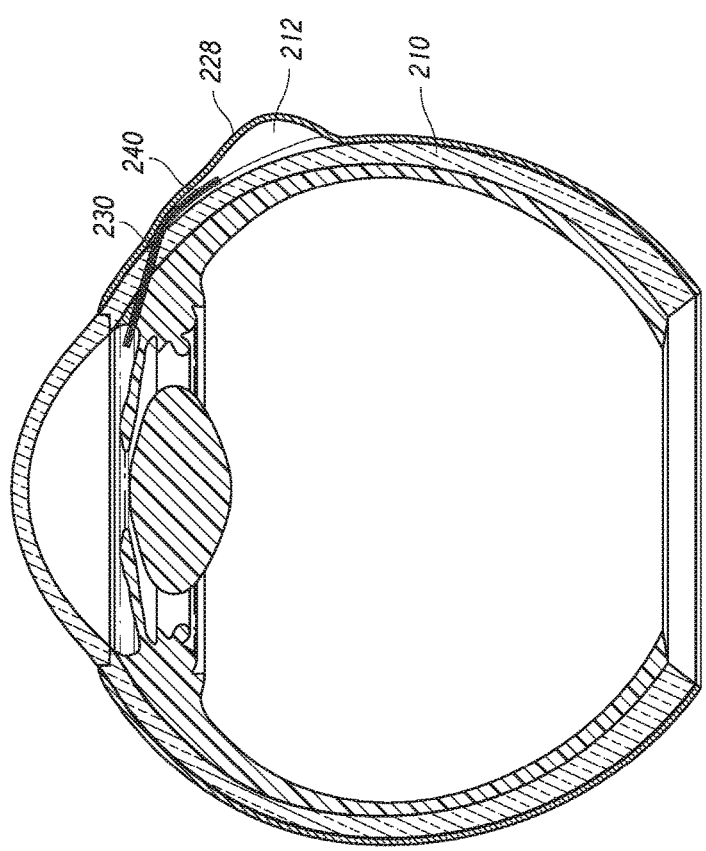

In accordance with some embodiments of the procedure, after the injector docking device is removed, the bleb can optionally be compressed or pushed down by the surgeon (e.g., using a sponge, q-tip, vexel, or finger) to gently urge the outflow end of the shunt toward a deep layer of the target outflow region. For example, as shown in FIG. 20, the bleb 212 can be pushed down from the limbus towards the superior part of the bleb 212 to gently urge the outflow end 240 of the shunt 230 toward a deep layer of the target outflow region. As shown, the outflow end 240 of the shunt 230 can be laid down flat onto or against the sclera. Compression of the bleb may not be necessary, especially if a BSS is used. Additionally, repositioning of the shunt may be done at this moment, if desired. Furthermore, the bleb will continue to deflate and eventually reduce further in size from that illustrated in FIG. 20. The puncture hole in the conjunctiva 228 can be closed with fibrin glue or a small suture, if desired.

In accordance with some embodiments, if the shunt outflow end 240 protrudes from the conjunctiva 228 at this stage in the procedure, the surgeon can balloon the target outflow region by injecting additional fluid into the bleb 212. This ballooning can cause the target outflow region to envelop the outflow end 240 of the shunt 230. Similarly, in some embodiments, when no injector docking device is used, a surgeon can inject fluid into the target outflow region after the injector is removed in order to cause the target outflow region to envelop the outflow end of the shunt, as discussed below.

"Freehand" Ab Externo Implantation Methods and Devices

Figure 21:
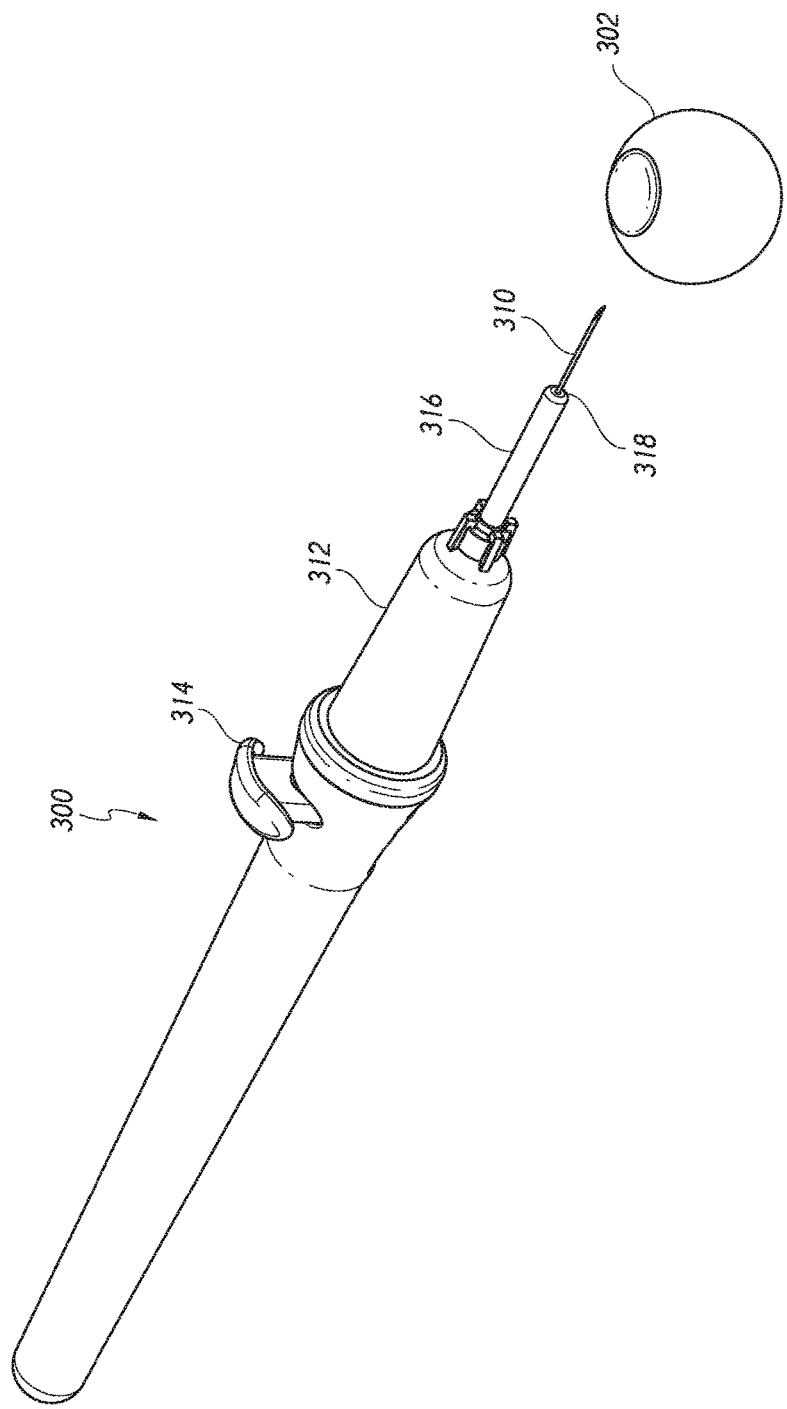
FIG. 21 illustrates another procedure for implanting an intraocular shunt into an eye using only an injector, according to some embodiments.

As noted above, various embodiments of the methods and devices disclosed herein allow a surgeon to use an injector docking device to perform a "guided" procedure in which an injector docking device creates a generally fixed spatial or geometrical relationship that assists in defining an entry point for the needle on the surface of the eye. The surgeon can perform this guided procedure to ensure accurate placement of the shunt within the eye. Additionally however, some embodiments of the methods and devices disclosed herein can enable a surgeon to perform a "freehand" procedure in which an injector docking device is not used. FIG. 21 illustrates an embodiment of a device and procedure in which "freehand" placement of a shunt is performed without an injector docking device.

FIG. 21 shows an injector 300 being used to deliver a shunt into an eye 302. The injector 300 can be any of a variety of injectors, including prior art injectors. However, the methods disclosed herein, whether a prior art injector is used or not, can be advantageous and enable a surgeon to perform ab externo placement of a shunt without creating a scleral flap or otherwise requiring a conjunctival dissection, as discussed above.

Referring to FIG. 21, the injector 300 can comprise a needle 310, a housing 312, an actuator 314, and an actuation mechanism disposed within the housing 312 and responsive to the actuator 314 for releasing the shunt from the needle 310. As discussed above, a surgeon can approach the eye 302 freehand (e.g., without the use of an injector docking device engaged with the eye or otherwise providing a fixed support and predetermined entry point into the eye for the needle of the injector). The surgeon can determine the proper entrance area and entrance angle for the needle without the use of an injector docking device. The surgeon can inject the needle 310 through the conjunctiva and sclera (e.g., similar to the needle track they already do for the Ahmed or Baerveldt tube shunt placements).

Thereafter, the surgeon can compress the actuator 314 in order to cause the actuation mechanism to release the shunt. For example, the actuation mechanism can advance a plunger rod within the needle 310 to distally advance the shunt within the needle 310 and/or cause the needle 310 to be retracted proximally relative to the shunt, thereby exposing the shunt. Features of injectors described in related U.S. Patent Application Publication Nos. 2010/0100104, 2012/0123430, and 2012/0123436 and International Patent Application No. PCT/US2014/065515 can be incorporated into some embodiments of the devices and procedures disclosed herein, the entireties of the disclosures of each of which are incorporated herein by reference.

In addition, according to some embodiments of the procedures disclosed herein, FIG. 21 illustrates that the procedure can be performed without creating a bleb or otherwise ballooning the target outflow region prior to implanting the shunt. Accordingly, without pre-implantation bleb creation or ballooning of the target outflow region, at the end of either a "freehand" procedure or a "guided" procedure (and after the injector removal), the shunt outflow end would stick out of the eye. Thereafter, the surgeon can balloon the target outflow region up around the shunt outflow end or "out" location until the conjunctiva and the target outflow region fully engulf the shunt outflow end, thus positioning the shunt fully inside the bleb or balloon (and the shunt outflow end is positioned within the target outflow region). At that point, the bleb can be pushed down and thereby laying the shunt flat against the sclera, as described herein.

Accordingly, some embodiments of the ab externo methods disclosed herein can be performed without any guidance or assistance from other structures and can rely solely on placement and injection of the needle by the surgeon. These "freehand" procedures may be performed in a surgical setting and can incorporate many of the features of the methods disclosed herein, such as pre- and/or post-implantation bleb creation or ballooning of the target outflow region.

Additional "Guided" Ab Externo Implantation Methods and Devices

In accordance with some embodiments, any of the methods disclosed herein can be implemented using a shunt that has one or more color features to facilitate or confirm placement of the shunt within the eye. For example, in some embodiments, the shunt can comprise one or more rings or indicia at one or more locations along the length of the shunt, such as at discrete intervals, such as every 1 or 2 mm. Further, the shunt can be stained or comprise a color to provide visual contrast against the sclera, conjunctiva, and/or other aspects of the eye to facilitate visualization of the shunt during the procedure. Additionally, in accordance with some embodiments, whether the shunt comprises one or more colored features, the method can be implemented using a gonio lens to verify placement or positioning of the shunt within the eye.

Optionally, in some embodiments, the injector 300 can comprise a sleeve 316 or the housing 312 can be dimensioned provide a longitudinal placement reference or stopper 318 that contacts the outside of the eye 302 once a proper needle depth has been reached. The stopper 318 of the sleeve 316 can be a blunt distal end of the sleeve 316. For example, features of contact sleeves and injectors described in related U.S. Pat. No. 9,192,516 can be incorporated into some embodiments of the devices and procedures disclosed herein, the entirety of the disclosure of which is incorporated herein by reference. Such embodiments can therefore be characterized as semi-guided in that the depth of needle penetration can be limited by the sleeve.

Figure 22:
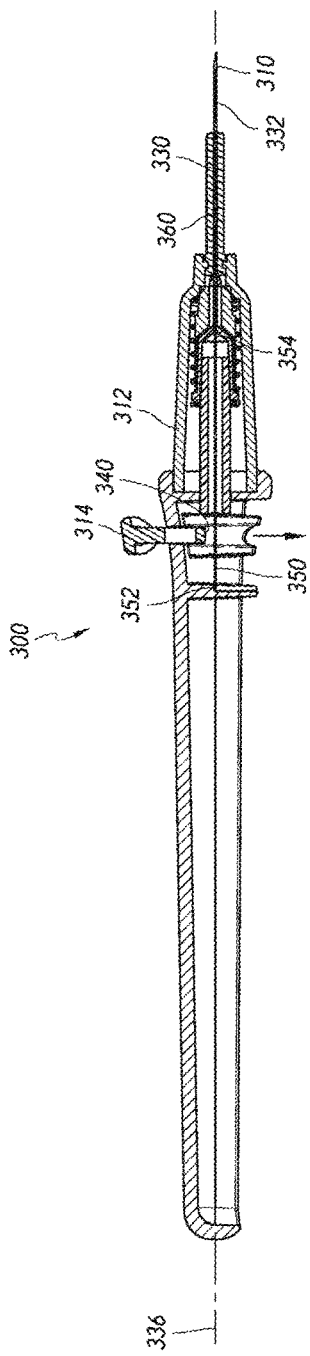
FIG. 22 illustrates a cross-section of the injector shown in FIG. 21, according to some embodiments.

FIG. 22 illustrates a cross-section of the injector 300 shown in FIG. 21, according to some embodiments. The injector 300 can comprise a pusher rod 330 disposed within a lumen of the needle 310. The pusher rod 330 can abut a proximal end of a shunt 332 disposed within the needle 300. Further, the longitudinal position of the pusher rod 330 along a central axis 336 of the injector 300 can be fixed relative to the housing 312. Furthermore, the actuator 314 can comprise an actuator contact portion 340. Upon depression of the actuator 314 into the housing 312, the actuator contact portion 340 can move downwardly until contacting a needle retractor component 350. The needle retractor component can be coupled to the housing 312 at a proximal end 352 and to the needle 310 at a distal end 354.

In use, the surgeon can depress the actuator contact portion 340 until it contacts the needle retractor component 350, and continued depression of the actuator 314 can cause the needle retractor component 350 to deflect away from the central axis 336 of the injector 300. Because the needle retractor component 350 is coupled at its proximal end 352 to the housing 312, the deflection will cause the distal end 354 of the needle retractor component 350 to be moved toward the proximal end 352, thus causing the needle 310 to be proximally withdrawn into the housing 312. As this occurs, the pusher rod 330 can maintain its longitudinal position along the central axis 336, thus causing the shunt 332 to be exposed and released as the needle 310 is proximally retracted relative to the pusher rod 330 and the shunt 332.

Figure 23:
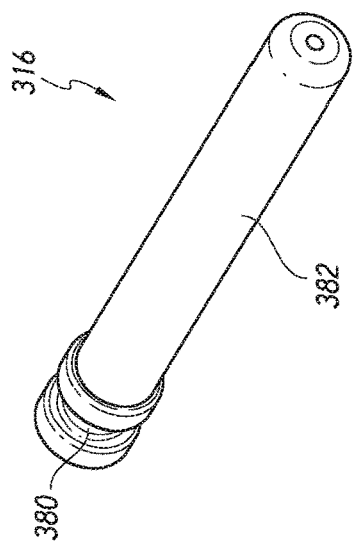

In accordance with some embodiments, the sleeve 316 can cooperate with a modular injector docking device to provide guidance to the injector. FIG. 23 illustrates that the sleeve 316 can comprise a proximal engagement portion 380 that can be coupled to a distal end of a housing of an injector. In some embodiments, the sleeve 316 can be retrofitted onto existing injectors. Further, the sleeve 316 comprises an outer surface 382 that can be used to mate with a corresponding portion of the modular injector docking device. An embodiment of such a modular injector docking device is shown in FIG. 24.

Figure 24:
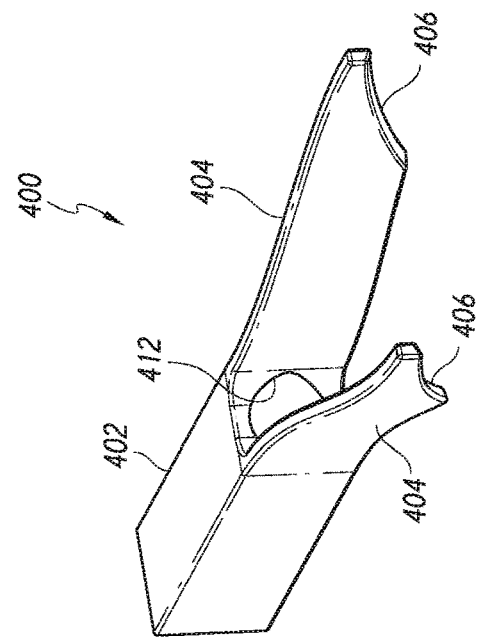
FIGS. 23 and 24 illustrate portions of an injector docking device for use with an injector, according to some embodiments.

In FIG. 24, a modular injector docking device 400 is shown that can comprise a body portion 402 and one or more prongs 404 extending from the body portion 402. The prongs 404 can taper toward tip portions 420 thereof. The tip portions 420 can be used to contact the eye, as discussed below. In accordance with some embodiments, the prongs can comprise an arcuate portion 406, which can be configured to match or mate against the surface of an eye.

The body portion 402 of the injector docking device 400 can comprise a lumen 412 having an inner profile that matches an outer profile of the outer surface 382 of the sleeve 316. As shown in FIGS. 23 and 24, the inner and outer profiles can be generally circular, thus allowing free rotation of the injector docking device 400 about the sleeve 316. However, other profiles can be used that limit or resist relative rotation between the injector docking device 400 and the sleeve 316. For example, triangular, square, or other polygonal shapes can be used. Additionally, one or more notches, grooves, or other surface features and corresponding notches, grooves and surface features can be formed in the injector docking device 400 and the sleeve 316 in order to resist or prevent relative rotational movement between the injector docking device 400 and the sleeve 316.

In use, the modular injector docking device 400 can be coupled to a sleeve 316 of an injector 300, as shown in FIGS. 25 and 26. These figures illustrate another procedure for implanting an intraocular shunt into an eye using an injector and the injector docking device shown in FIGS. 23 and 24, according to some embodiments.

As shown in FIG. 25, the modular injector docking device 400 can be positioned against an eye 410. In accordance with some embodiments, the prongs 404 can be positioned such that the tip portions 420 of the prongs 404 are positioned adjacent to the corneal limbus 430 of the eye 410. The tip portions 420 of the prongs 404 can be positioned adjacent to (e.g., posterior to, anterior to, or against) the corneal limbus. For example, in some embodiments, the tip portions 420 can be positioned within about 4 mm, about 3 mm, about 2 mm, about 1 mm, or against the corneal limbus 430. However, the tip portions 420 can be placed at any suitable location as required to achieve placement of the shunt within the desired target outflow region. As such, the surgeon can use fiducial markers of the eye to align or otherwise position the tip portions 420 against the eye 410.

While maintaining the position of the injector docking device 400, the surgeon can then advance the needle 310 into the eye 410. In doing so, the cooperation between the sleeve 316 and the injector docking device 400 can allow the surgeon to carefully control the trajectory and placement of the needle 310 within the eye 410.

The method illustrated in FIGS. 25 and 26 also illustrates that a bleb 440 can be formed in the eye 410 prior to implantation of the shunt. However, as discussed herein, the bleb 440 can be formed after initial placement of the shunt within the eye, thus allowing more precise visualization for the surgeon in performing a procedure in which the injector docking device is not coupled or removably affixed to the eye.

FIGS. 27-35D illustrate additional injector embodiments in which the injector docking device and the injector are formed unitarily, coupled with each other, or otherwise formed from a single, continuous housing or material to form a single handheld unit. Further, related shunt implantation procedures are also illustrated.

Figure 28:
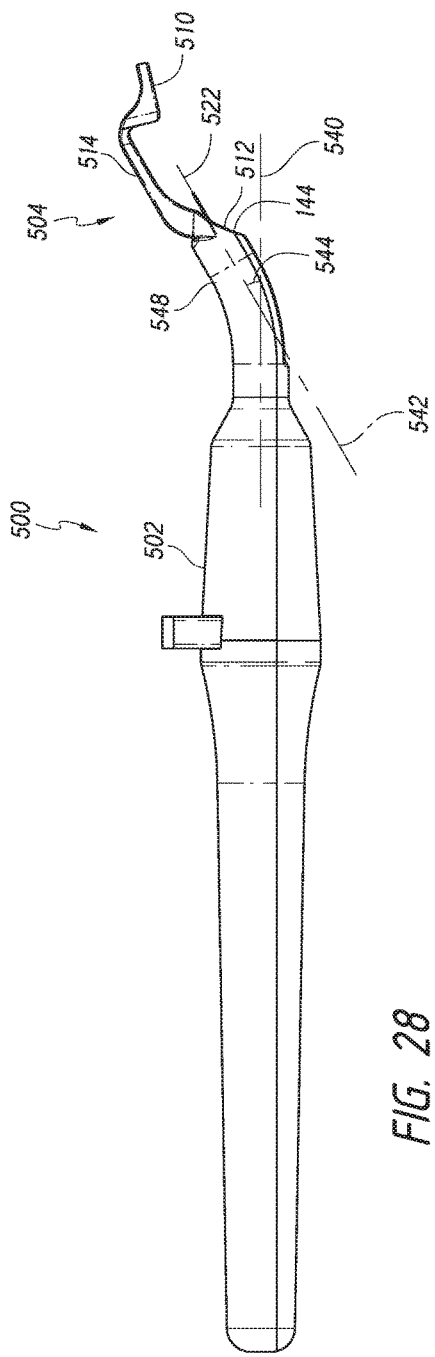
Figure 29:
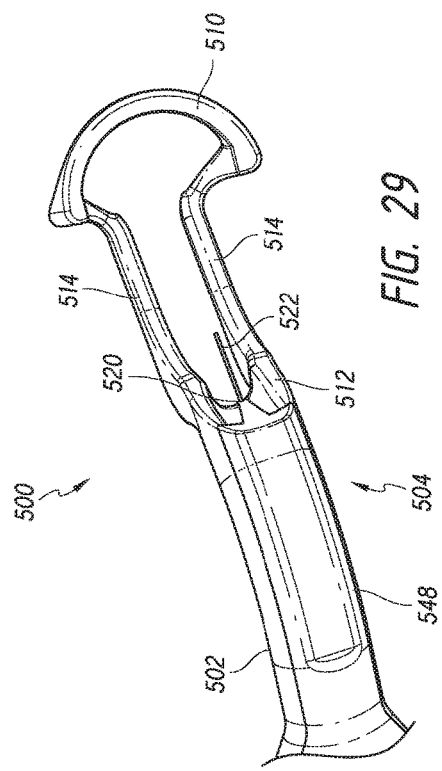

Referring to FIGS. 27-29, an injector 500 can be provided that comprises a housing 502 coupled directly with an injector docking device 504. The injector docking device 504 can be co-molded or otherwise permanently attached to the housing 502. In some embodiments, the injector docking device and the injector housing can be formed from a single, continuous piece of material. For example, the housing 502 can comprise upper and lower halves or left and right halves in which a portion of each half defines sections of the injector docking device 504.

The injector docking device 504 can comprise at least one eye-contacting portion that can be aligned with a fiducial marker of the eye and enable a surgeon to contact the injector docking device 504 against the eye during the implantation procedure. For example, in some embodiments, the injector docking device 504 can comprise a ring-shaped structure similar to the injector docking device illustrated in FIGS. 6-10 and 32-35D. However, in some embodiments, such as that illustrated in FIGS. 27-29, the injector docking device 504 can comprise a partial-ring or half-ring component or a structure having two or more contact portions that can be positioned against the eye during the procedure. Further, in some embodiments, the half-ring component can comprise a vacuum pocket or channel through which suction can be applied to removably couple the injector docking device to the eye. The contact portions of the structure, whether ring shaped or otherwise, can be used to facilitate alignment of the needle with the eye and provide guidance of the needle during the implantation process.

In the embodiment shown, the injector docking device 504 can comprise an opposing arcuate, half-ring component 510 that can serve as a contact portion for initial alignment of the injector docking device 504 with the eye. The injector docking device 504 can also comprise an opposing abutment portion 512 extending adjacent to an outlet 520 of a needle 522, as shown in FIGS. 28 and 29. The opposing abutment portion 512 can be configured to contact the eye during the shunt delivery procedure.

In some embodiments, the half-ring component 510 and the opposing abutment portion 512 can be coupled together via a bridge 514. The bridge 514 can comprise one or more (shown as two) elongate structures that interconnect portions of the half-ring component 510 and the opposing abutment portion 512 to maintain the half-ring component 510 and the opposing abutment portion 512 in a spaced apart relationship. In this manner, the half-ring component 510 and the opposing abutment portion 512 can be positioned on opposing or different portions of the eye, for example, around the cornea. Further, the bridge 514 can comprise an aperture or targeting feature (such as the targeting ring noted herein) that allows the surgeon to visually verify placement of the injector docking device 504 relative to the eye.

The half-ring component 510 and the opposing abutment portion 512 can comprise contact surfaces that complement the external geometries of the eye, thereby facilitating placement of the injector docking device 504 on the eye during the shunt delivery procedure.

In accordance with some embodiments, the half-ring component 510 and the opposing abutment portion 512 can each comprise surfaces that extend along a spherical or ellipsoidal path. In some embodiments, the half-ring component 510 and the opposing abutment portion 512 can each comprise surfaces that extend along a common spherical or ellipsoidal path. For example, the surfaces of the half-ring component 510 and/or the opposing abutment portion 512 can be shaped to match the limbal curvature of the eye. In some embodiments, the surfaces of the half-ring component 510 and/or the opposing abutment portion 512 can have a radius of curvature 144 (as noted above with respect to FIG. 10; the details of which can be the same and are not repeated here for brevity). In some embodiments, the surfaces of the half-ring component 510 and/or the opposing abutment portion 512 can have an annular or rounded shape that can be mated against the limbus between the cornea and the sclera.

Referring again to FIG. 28, the housing 502 can extend along a longitudinal axis 540 and the injector docking device 504 can extend along a longitudinal axis 542. The relative orientation of the longitudinal axis 540 and the longitudinal axis 542 can advantageously enable a surgeon to reach any of the quadrants of the eye during the implantation procedure. For example, the longitudinal axis 540 can extend transversely relative to the longitudinal axis 542. In some embodiments, the longitudinal axis 540 can extend transversely relative to the longitudinal axis 542 at an angle 544 of between about 0 degrees and about 60 degrees, between about 20 degrees and about 50 degrees, between about 30 degrees and about 40 degrees, or about 35 degrees. This angular orientation can therefore provide easier access to different quadrants of the eye.

Additionally, as shown in FIGS. 28 and 29 the injector docking device 504 can comprise a neck section 548 along which the needle 522 can have a substantially straight path. For example, the needle 522 can extend along a straight path along the longitudinal axis 544. Proximal to the neck section 548, the path of the needle 522 can curve slightly and then the needle path can follow a substantially straight path along the longitudinal axis 540. The straight path of the needle 522 in the neck section 548 can advantageously assist the needle 522 in following a straight path as the needle 522 is advanced distally out of the neck section 548 during the implantation procedure.

In accordance with some methods, a shunt delivery procedure can be performed using the injector docking device 504 for initial guidance by placing one or both of the half-ring component 510 and the opposing abutment portion 512 against the eye, such as against at least a portion of the limbus. In some embodiments, the half-ring component 510 and the opposing abutment portion 512 can be placed into contact with the eye along the limbus. However, in other embodiments, either the half-ring component 510 or the opposing abutment portion 512 can be placed in contact with a left or right side of the limbus while the other of the half-ring component 510 or the opposing abutment portion 512 is spaced apart or tilted up from the eye. This initial contact can provide initial confirmation to the surgeon and allow the injector 500 to be initially guided to the target entry point in the eye.

Once the injector 500 has been placed in contact against the eye, whether one or both of the half-ring component 510 or the opposing abutment portion 512 are in contact with the eye, the surgeon can begin advancing the needle tip portion toward the target entry point in the eye.

Referring now to FIGS. 30A-31C, an embodiment of a shunt delivery procedure is shown. As illustrated in FIGS. 30A-30C, the injector 500 can be positioned against an eye 550 with the half-ring component 510 positioned adjacent to or in contact with a right side 560 of the corneal limbus of the eye 550. For example, the half-ring component 510 can be positioned posterior to, anterior to, or against the corneal limbus. Further, a needle of the injector 500 is positioned adjacent to a target outflow area of the eye 550. In the illustrated embodiment, the half-ring component 510 can be positioned in a location opposite the target outflow region along the corneal limbus. The half-ring component 510 can be used for initial guidance of the injector 500. When the half-ring component 510 is placed on the right side limbus 560, the injector can be held or tilted up on the opposite side (i.e., on the left side limbus 562). The injector 500 can then be slowly tilted back down towards the left of the eye 550 until the needle tip portion 570 comes close/touches the sclera 572 on the anticipated entry point (which could be marked beforehand for confirmation). As the needle tip portion 570 reaches the sclera 572 (e.g., at the same time), the half-ring component 510 can fully rest on the right side limbus 560.

In the starting position shown in FIGS. 30A-30C, the needle is now lined up (position and needle entry angle), and the surgeon can then prepare to push the needle into the eye along the straight final needle length section. This may require a slight upwards angled push until the opposing abutment portion 512 comes to rest against the sclera 572, as shown in FIGS. 31A-31C.

In accordance with some embodiments, as the needle tip portion 570 is pushed in, the half-ring component 510 can move away from the eye 550 and is no longer aligned or used. However, as discussed herein and with respect to the embodiments shown in FIGS. 32-35D, some embodiments can be implemented in which both the half-ring component 510 and the opposing abutment portion 512 are placed into initial contact with the eye 550 and maintain that same contact with the eye 550 throughout the implantation procedure.

Figures 32, 33:
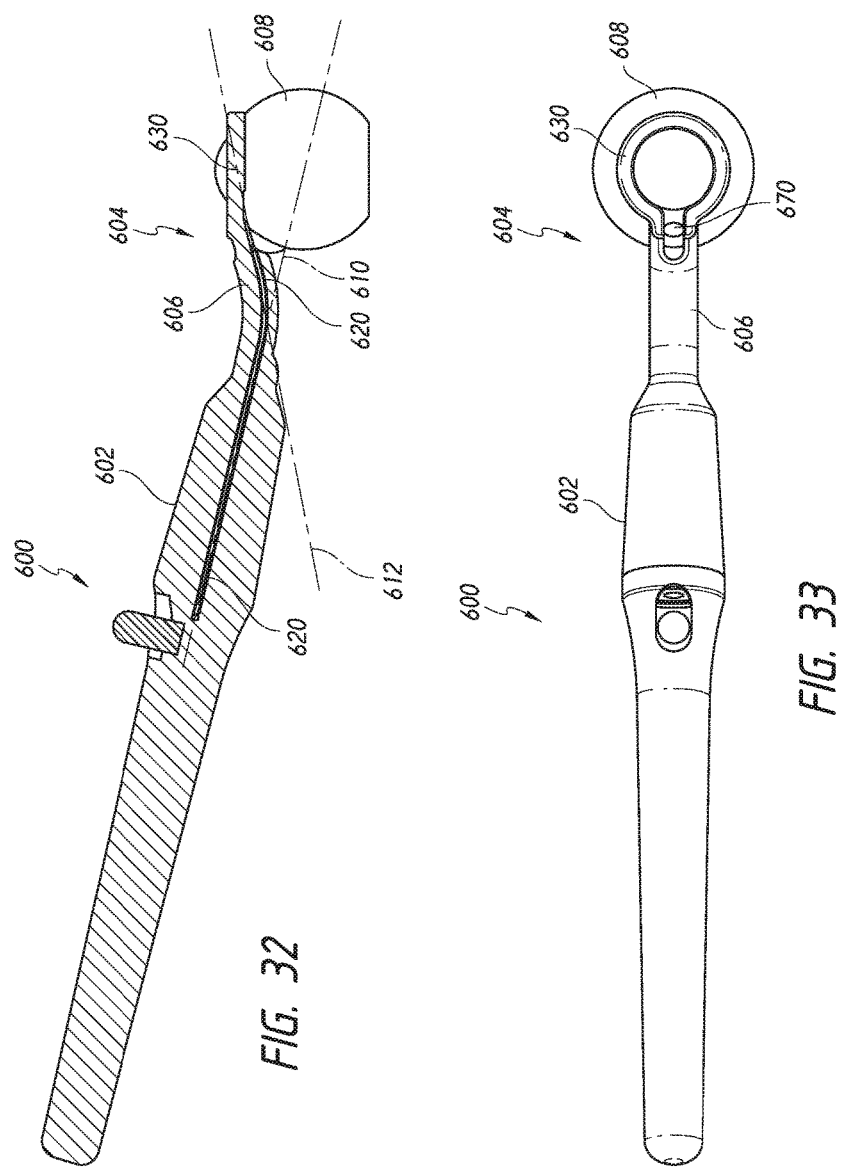
FIGS. 32-35D illustrate yet another injector docking device formed unitarily with an injector, as well as a related procedure for implanting an intraocular shunt into an eye, according to some embodiments.
Figure 34:
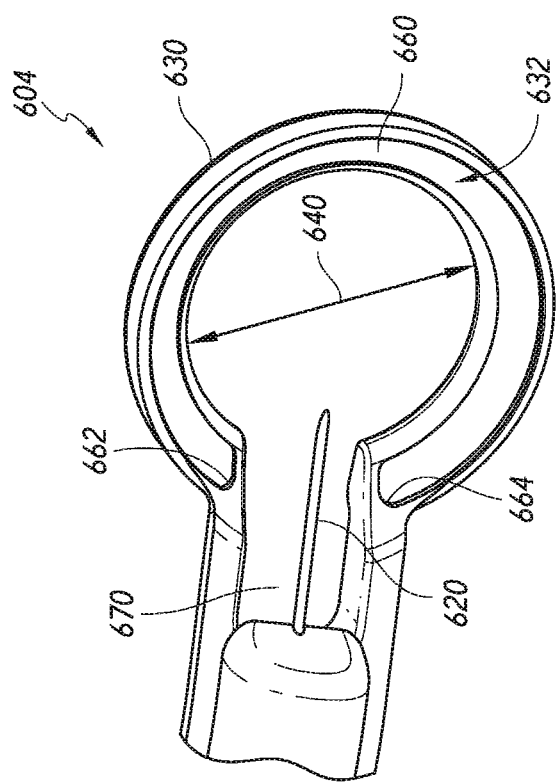

For example, in some embodiments, one or more portions of the injector docking device 504 can comprise a transparent material that allows the surgeon to see the needle location, angle, and path, thereby allowing the surgeon to place the half-ring component 510 and the opposing abutment portion 512 can be in full contact with the eye 550 throughout the procedure. In some embodiments, in a pre-deployment position, the needle tip portion 570 can be recessed into the neck section 548 (as shown in the embodiment of FIGS. 32-34) and, after the surgeon confirms that the needle path is proper through visualization through the transparent injector docking device, the needle tip portion 570 could be advanced distally through or beyond the opposing abutment portion 512.

The docking device of any of the embodiments disclosed herein can be formed from a transparent material. Further, the docking device can have one or more markers, lines, or other indicia that can be used to align the injector docking device with the eye, such as the limbus, sclera, cornea, or other fiducial markers of the eye.

After the correct needle bevel position is confirmed visually (e.g., through a microscope), the surgeon pushes a button or otherwise engages a mechanism that automatically withdraws the needle while holding the shunt stationary within the eye 550. This can be done slowly or very quickly (e.g., in less than about 0.5 seconds). It may be preferable, in some embodiments, to quickly withdraw the needle and release the shunt to minimize any eye movement. Once the needle has been removed from the eye 550, the injector 500 can be removed.

Thereafter, as discussed above and not repeated herein for brevity, the target outflow region can be ballooned in order to ensure that the outflow end of the shunt is positioned within the target outflow region. For example, a bleb can be formed at the entry point of the needle to balloon the conjunctiva, intra-Tenon's adhesion space, or the suprascleral space (and other spaces disclosed herein) to bring the outflow end of the shunt into the respective space. Further, as discussed herein, the ballooned space or bleb can thereafter be carefully swiped down to lay the shunt 680 flat within the target outflow region, and proper shunt position in the target outflow region can be visually confirmed. If necessary, the position of the shunt outflow end can be adjusted manually with forceps from outside of the eye 550.

Figure 31D:
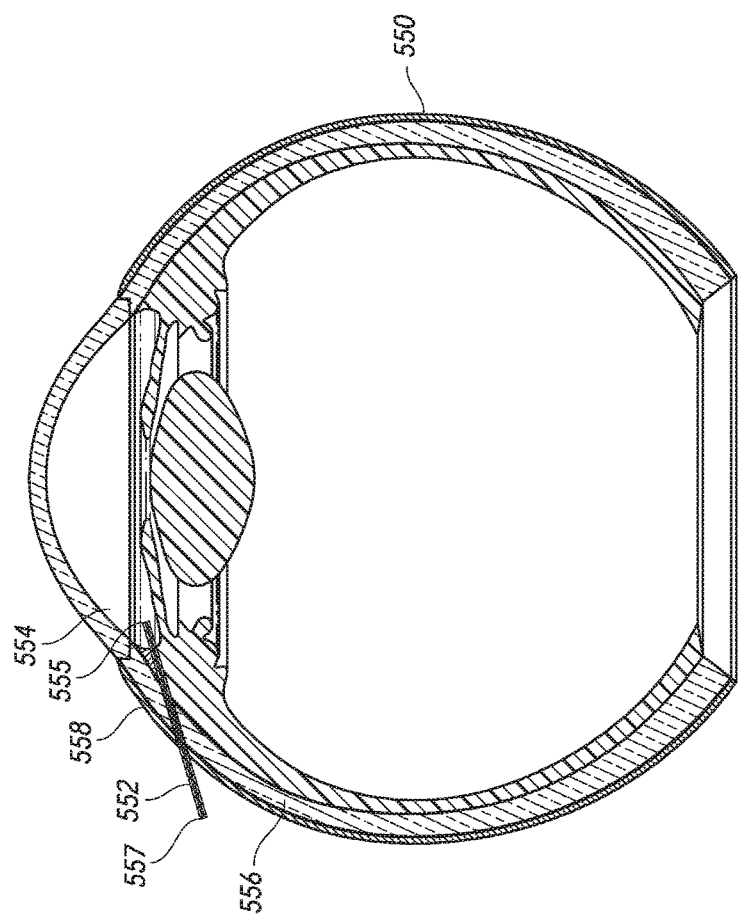
Figure 31E:
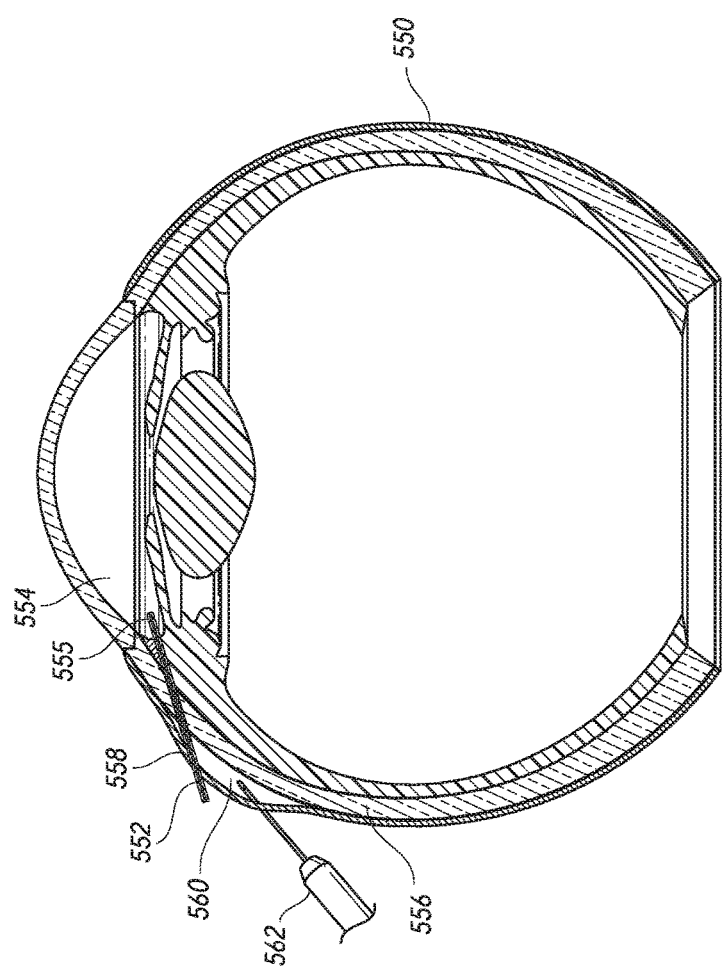
Figure 31F:
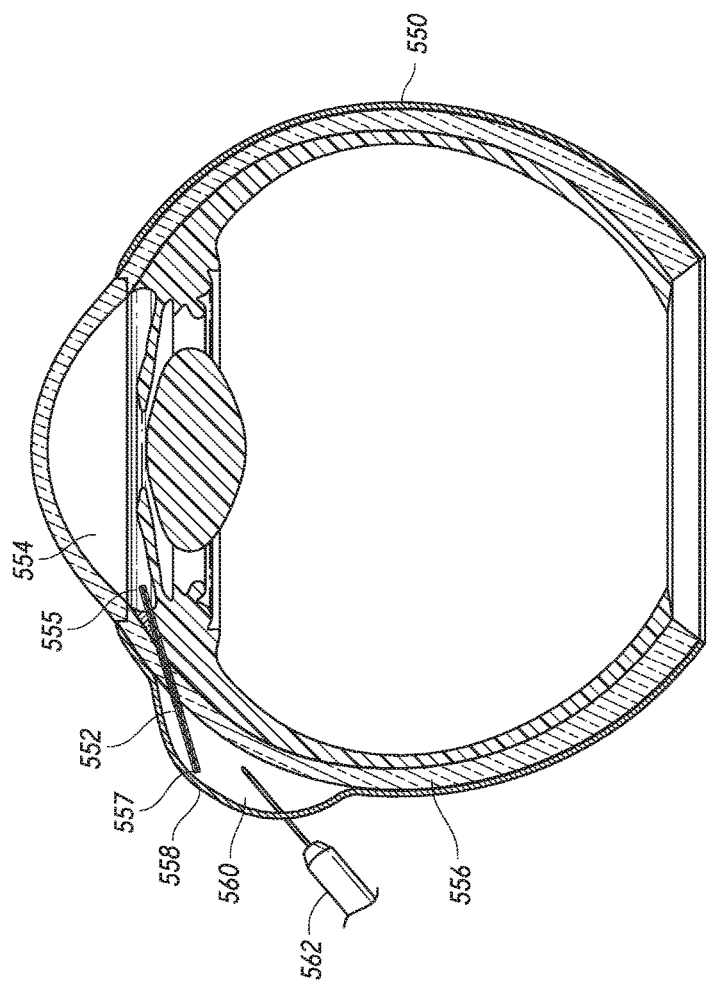

Referring now to FIGS. 31D-31F, after the shunt 552 is released from the injector, a distal or inflow portion of the shunt 552 can be positioned within the eye 550 while a proximal or outflow portion of the shunt 552 initially extends outside of a target outflow region. For example, the outflow portion of the shunt 552 can be positioned within or outside of the eye 550 prior to subsequent repositioning within the target outflow region. As discussed below, a bleb can be formed within the target outflow region in order to balloon the target outflow region around the outflow portion of the shunt 552. By forming a bleb or ballooning the target outflow region, the target outflow region can be manipulated in order to encapsulate or reposition the outflow portion of the shunt 552 within a target outflow region of the eye 550.

Further, although the present procedure is illustrated with regard to the inserter 500, any of the embodiments of injector docking devices or injectors can be implemented to perform the initial placement of the shunt within the eye in preparation for bleb formation after the shunt has been released into the eye 550.

For example, referring to FIG. 31D, placement of a shunt 552 is illustrated such that an inflow end 555 of the shunt 552 is positioned in a final target position within the eye 550. In some embodiments, the inflow end 555 of the shunt 552 is positioned in a region of higher pressure in the eye (e.g., the anterior chamber 554) and an outflow end 557 of the shunt 552 is positioned outside of the eye 550 such that the shunt 552 extends through the sclera 556 and conjunctiva 558.

Referring to FIG. 31E, after the shunt 552 has been placed and has been determined to be properly engaged with the eye tissue (e.g., with a gelatin shunt, a clinician can wait a set period of time for the shunt to hydrate and expand within the eye tissue to reduce shunt migration), the target outflow region can be ballooned. Bleb formation can be performed by using a syringe 562 or other tool to inject an amount of a BSS, lidocaine, viscoelastic, and/or healon mixture into the target outflow region. In FIG. 31E, the target outflow region is illustrated as the subconjunctival space. As the bleb 560 is formed, and with the shunt 552 secured within the underlying eye tissue, the conjunctiva 558 overlying the target outflow region moves proximally toward the outflow end 557 of the shunt 552 until the outflow end 557 of the shunt 552 is swallowed or encapsulated within the eye, as shown in FIG. 31F. The outflow end 557 can be further manipulated in order to position or ensure positioning of the outflow end 557 within the target outflow region. Thereafter, the ballooned space or bleb 560 can be swiped down (e.g., deep to the conjunctiva 558) to lay the shunt 552 flat within the target outflow region.

Referring now to FIGS. 32-35D, an injector 600 can be provided having various features similar to those discussed above with regard to the injector 500. One of the differences is that the injector 600 can have an injector docking device 604 comprising a ring-shaped structure that can be maintained in contact with an eye 608 throughout the shunt implantation procedure. Further, the injector docking device 604 can also comprise a vacuum or suction mechanism similar to that discussed above with respect to the embodiment shown in FIGS. 3A-7.

Referring to FIGS. 32-34, the injector 600 can comprise a housing 602 and a neck section 606. The housing 602 can extend along a longitudinal axis 610 that extends transverse relative to a longitudinal axis 612 of the neck section 606 of the injector docking device 604. As noted above with regard to the embodiment shown in FIGS. 28-30, the relative orientation of the longitudinal axes 610, 612 of the housing 602 and the neck section 606 can advantageously enable a surgeon to reach any of the quadrants of the eye during the implantation procedure. For example, longitudinal axes 610, 612 of the housing 602 and the neck section 606 can extend transversely relative to each other at an angle 544 of between about 0 degrees and about 60 degrees, between about 20 degrees and about 50 degrees, between about 30 degrees and about 40 degrees, or about 35 degrees. This angular orientation can therefore provide easier access to different quadrants of the eye.

Further, as shown in FIG. 32, the neck section 606 of the injector docking device 604 can support a needle 620 along a substantially straight path. For example, the needle 620 can extend along a straight path along the longitudinal axis 612. Proximal to the neck section 606, the path of the needle 620 can curve slightly and then the needle path can follow a substantially straight path along the longitudinal axis 610. The straight path of the needle 620 in the neck section 606 can advantageously assist the needle 620 in following a straight path as the needle 620 is advanced distally out of the neck section 606 during the implantation procedure.

Referring now to FIG. 34, the injector docking device 604 can comprise a ring-shaped structure 630 having an eye-contacting surface 632 that complements the external geometries of the eye, thereby facilitating placement of the injector docking device 604 on the eye during the shunt delivery procedure. The eye-contacting surface 632 of the ring-shaped structure 630 can be configured to extend along a majority of the corneal limbus when positioned against the eye. In some embodiments, the eye-contacting surface 632 can be positioned adjacent to the corneal limbus. For example, the eye-contacting surface 632 can be positioned posterior to, anterior to, or against the corneal limbus.

The eye-contacting surface 632 of the ring-shaped structure 630 can have a concave shape and extend along a spherical or ellipsoidal path. The eye-contacting surface 632 can be shaped to match the scleral curvature of the eye. In some embodiments, the radius of curvature of the eye-contacting surface 632 can approximate the radius of curvature of the sclera of the eye in order to better mate against the sclera. For example, the eye-contacting surface 632 can have a radius of curvature 144 of between about 11 mm and about 14 mm, between about 11.6 mm and about 13.4 mm, between about 11.9 mm and about 12.9 mm, or about 12.4 mm. The radius of curvature can fall within acceptable ranges of the radius of curvature of the sclera, as known in the art or measured using known methods, as discussed above.

In some embodiments, the ring-shaped structure 630 can have an annular or rounded shape having an inner diameter 640 that allows the ring-shaped structure 630 can be mated against the limbus between the cornea and the sclera. For example, the inner diameter 640 can be between about 11 mm and about 14 mm, between about 12 mm and about 13.5 mm, or about 13 mm. Accordingly, in some embodiments, the ring-shape structure 630 can be sized to fit around a limbus of an eye without contacting or having substantial contact with the limbus.

Additionally, the eye-contacting surface 632 can be configured to be coupled to or removably affixed to the eye 608. As noted above in other embodiments, the injector docking device 604 can provide suction on and/or otherwise engage the cornea and/or below corneal limbus (e.g., along the sclera). An alternative to suction is to provide a frictional or grippy surface, such as ridges, hooks, or spikes that may penetrate or otherwise engage the conjunctiva. Such a surface can enable the surgeon to contact the injector docking device 604 against the eye and achieve suitable frictional and/or mechanical engagement with the eye. However, suction and mechanical engagement can both be used in some embodiments.

For example, as shown in FIG. 34, the eye-contacting surface 632 can be formed to include a vacuum pocket or channel 660. The vacuum pocket 660, similar to the other vacuum pocket's discussed herein and other embodiments, can allow the ring-shaped structure 630 of the docking portion 604 to engage or be removably affixed to the eye 608 during the implantation procedure. A corresponding vacuum port can be positioned at either a first or second end 662, 664 of the vacuum pocket and be in fluid communication with a channel and vacuum source via the housing 602 of the injector 600.

As also illustrated FIGS. 33 and 34, the ring-shaped structure 630 can comprise a gap or opening 670 through which the needle 620 can pass. In this manner, with the eye-contacting surface 632 positionable below the limbus of the eye 608, the needle 620 can enter the eye 608 at a location below the limbus, as generally shown in FIG. 32. The opening 670 can extend along less than about ¼, less than about ⅕, less than about ⅙, less than about ⅐, less than about ⅛, less than about ⅑, less than about ⅒, or less than about 1/12 of the circumference of the ring-shape structure 630.

In some embodiments, in a pre-deployment position, the needle 620 can be recessed into the neck section 606 and, after the surgeon confirms that the needle path is proper, the needle 620 could be advanced distally through or beyond the opening 670 and into the eye 608. However, in a pre-deployment position, the needle 620 can also extend into the opening 670. Nevertheless, in order to ensure that the needle 620 does not contact the eye 608 when the eye-contacting surface 632 is first positioned against the eye 608, the needle 620 should not extend into the opening 670 beyond the eye-contacting surface 632 (e.g., beyond a curved plane having a radius of curvature that approximates that of the eye-contacting surface 632).

In accordance with some methods, a shunt delivery procedure can be performed using the injector 600 and the injector docking device 604. Such procedures are very similar to those discussed above with respect to the injector 500, except that the ring-shape structure 630 of the injector docking device 604 extends almost all the way around the limbus and can be affixed to the eye (e.g., via suction and/or mechanical engagement).

Figure 35A:
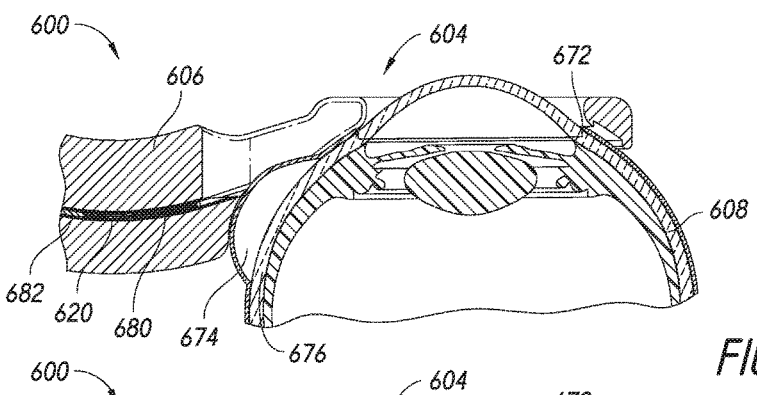

As shown in FIG. 35A, the needle 620 is inside the neck portion 606 and the ring-shape structure 630 is fully engaged around the limbus 672 of the eye 608. In the embodiment shown in FIGS. 35A-35D, the target outflow region 674 (here shown as the subconjunctival space) has already been ballooned and a bleb has been formed. However, as noted above, some embodiments can be performed in which the target outflow region 674 is ballooned after the shunt has been placed in the eye.

Figure 35B:
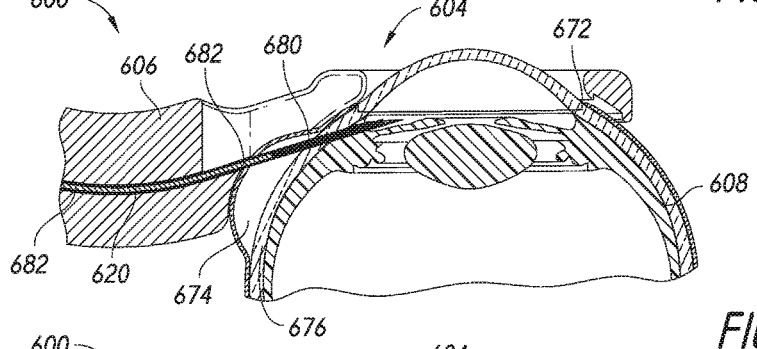

Referring to FIG. 35B, the needle 620 can be advanced out of the injector housing 602 (neck portion 606). The needle 620 preferably comes out straight at the shown angle, as discussed above, but could also come out in a slight curve to allow for a longer channel within the sclera 676. As noted above, the conjunctival or scleral entry point can be at about 4 mm, about 3 mm, or about 2 mm below the limbus. The needle 620 can be advanced through the target outflow region 674, the conjunctiva, sclera 676 and into the anterior chamber angle. The needle 620 carries a preloaded shunt 680 with it and the pusher rod 682 behind the shunt 680. The advancement of the needle 620 can be done either through actuation of a button or a slider, and may be manual or use an energy stored mechanism (e.g., spring loaded actuation, electrical motor, or magnetic movement).

Figure 35C:
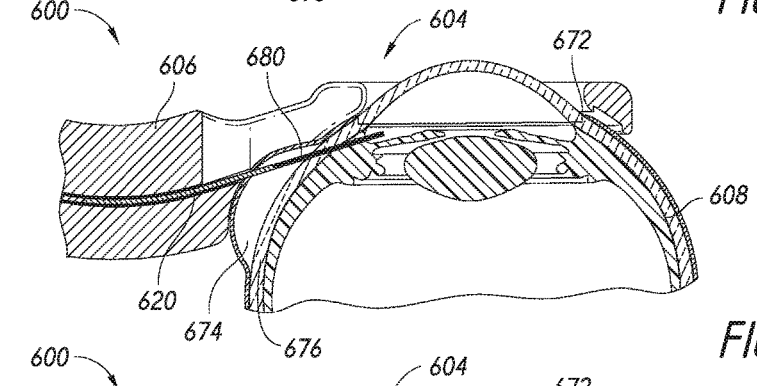
Figure 35D:
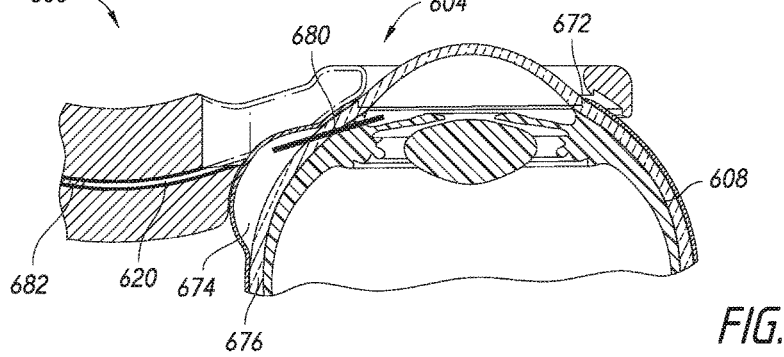

The surgeon can verify that the shunt 680 is properly positioned within the eye. For example, the surgeon can visually verify, through a surgical microscope, for example, that a bevel of the needle 620 is visible inside the eye. As shown in FIGS. 35C and 35D, after the shunt 680 is properly positioned within the eye, the surgeon can activate withdrawal of the needle 620 while holding the pusher rod 682 in place. This withdrawal can be done either through actuation of a button or a slider, and may be manual or use an energy stored mechanism (e.g., spring loaded actuation, electrical motor, or magnetic movement). The shunt 680 is thereby left in its final position, as shown in FIG. 35D.

At this point, the injector 600 can be removed from the eye 608. Thereafter, as discussed above and not repeated herein for brevity, if necessary, the target outflow region 674 can be ballooned in order to ensure that the outflow end of the shunt 680 is positioned within the target outflow region 674. For example, a bleb can be formed at the entry point of the needle to balloon the conjunctiva, intra-Tenon's adhesion space, or the suprascleral space (or other spaces disclosed herein) to bring the outflow end of the shunt 608 into the respective space. Further, as discussed herein, the ballooned space or bleb can thereafter be carefully swiped down to lay the shunt 680 flat within the target outflow region, and proper shunt position in the target outflow region can be visually confirmed. If necessary, the position of the shunt outflow end can be adjusted manually with forceps from outside of the eye 550.

Surgery Steps in Some Embodiments

The following discussion provides a variety of steps that can be performed in ab externo methods for injecting a shunt or stent into a target outflow region of the eye. Advantageously, the shunt can be injected into the temporal superior, temporal inferior, nasal superior, or nasal inferior quadrants in order to provide a conduit or outflow pathway from a region of higher pressure to a region of lower pressure, such as from the anterior chamber to any of the target outflow regions discussed herein. Advantageously, using some embodiments of this procedure, a shunt can be more easily placed in every quadrant of the eye (compared to ab interno approaches) since the injector needle no longer has to go across the entire anterior chamber. These steps can be performed using a "guided" procedure or a "freehand" procedure.

The following discussion provides a variety of actions that can be performed in carrying out some of the embodiments of the procedures disclosed herein. Not all of the following actions are required to be performed in some embodiments, and the following actions may take place in a different order, according to some embodiments. Thus, the presence of a specific action or its specific position in the list of possible actions are not an indication that such an action is required or that such an action must be performed prior to or after another given action.

When using an injector docking device, a surgeon can first measure the eye or confirm that the eye is within a size range and chose a ring or confirm that a given ring is the correct size for the patient. In some embodiments, the injector docking device can fit a range of eye sizes (based on corneal diameter), and in some embodiments, a single injector docking device can fit all eyes.

Step 1. Optionally, the surgeon can inject an antimetabolite into the target outflow region to open the target outflow region (e.g., subconjunctival space or other spaces disclosed herein), and wait for the antimetabolite to dissipate.

Step 2. Optionally, a BSS, lidocaine, viscoelastic, and/or healon mixture can be injected into a target outflow region (e.g., the subconjunctival space or other spaces disclosed herein) from about 2 mm to about 10 mm away of the planned shunt outflow location, to create a ballooned volume. The shunt can be injected into this created space. However, the injection of a mixture into the target outflow region can also be performed after the shunt is injected into the eye, as discussed herein. The exact level or layer (as necessitated by the target outflow region) of injection location can be controlled and can determine the shunt level position (e.g., sub-Tenon's, intra-Tenon's, or over-Tenon's, but still under the top conjunctival layer). The conjunctival entry hole can be closed with a suture or fibrin glue if desired, although the high metabolism of the conjunctiva can close the hole rapidly, such as within an hour of use.

Step 3. Optionally, for easier and straighter shunt placement in a subconjunctival location, the surgeon can perform a small local Tenon adhesion dissection in the area of the planned shunt placement. Such a local dissection can be done using a small gauge needle (e.g., 27 G or 30 G) or small knife. The needle or knife can be inserted into the target outflow region (e.g., subconjunctival space or other spaces disclosed herein) from a few millimeters away (e.g., between about 2 mm to about 10 mm) at a shallow angle (e.g., just like when performing a subconjunctival injection). The needle can then be moved sideways while sliding on the top sclera layer and can thereby cut off the Tenon adhesion to the sclera in that area. This step is optional, but if done can be easily combined with the injection in step 2 using the very same needle. In some embodiments, the surgeon can inject first and then move needle sideways to cut adhesions on the bottom of the ballooning. Alternatively, the surgeon can inject and move simultaneously. The conjunctival entry hole can be closed with a suture or fibrin glue if desired, although the high metabolism of the conjunctiva can close the hole rapidly, such as within an hour of use.

Step 4. If used, an injector docking device (using a targeting ring or other means) can be visually centered on the eye while aligning the injector guidance port near the nasal superior quadrant or other quadrant, as necessary. The surgeon can use markers and/or other guidance features for good alignment or automated vision systems to provide feedback or guidance to the surgeon.

Step 5. If necessary, the patient should be instructed to look temporal inferior (if orienting the injector docking device injector guidance port near the nasal superior quadrant) or other quadrant opposite the position of the injector guidance port, as necessary.

Step 6. Optionally, if using an injector docking device, surgeon can reach maximum high superior placement position, if desired, by rotating needle port of injector docking device to maximal superior position on the nasal side while maintaining clearance for injector. Otherwise, maximum clearance for the injector can be achieved by appropriate placement of the needle port.

Step 7. Optionally, if using an injector docking device, the surgeon can verify that the target outflow region ballooned volume is larger than the bleb pocket space in injector docking device. This can be visually verified by the creation of visibility of excess target outflow region ballooning around the pocket space of the injector docking device.

Step 8. Optionally, if using an injector docking device, the surgeon can secure or engage the injector docking device to the eye (e.g., by drawing vacuum on injector docking device or couple the ring to the eye using frictional coupling mechanism of the injector docking device). In some embodiments, the injector docking device may not be removably fixed or coupled to the eye, but may instead be abutted or positioned against the eye to provide a desired spacing of the injector relative to the eye or a desired entrance angle for the needle into the eye.

Step 9. If using an injector docking device, the surgeon can insert the injector all the way to the injector guidance port of the injector docking device until contacting the internal shoulder or stop of the injector guidance port. The sleeve of the injector can be positioned at the most forward part (i.e., the needle can be retracted into the sleeve), at this point. Alternatively, the needle could protrude beyond the sleeve when the injector is inserted into the injector guidance port, and the entire injector can be moved towards the eye while under sleeve-port guidance and the needle penetrates all layers as described in step 10.

Step 10. The needle can be actuated to move needle through conjunctiva, Tenon's capsule, sclera, and the anterior chamber angle tissue layers and into the anterior chamber. In some embodiments, this is done while the needle is fully guided by the guidance port of the injector docking device. In some embodiments, the shunt and pusher rod behind the shunt will move forward with the needle inside of it. In some embodiments, the conjunctival or scleral entry point can be at about 4 mm, about 3 mm, or about 2 mm below the limbus.

Step 11. The surgeon can then verify that the needle tip is visible in angle to ensure that an inflow end of the shunt is or can be positioned within the anterior chamber.

Step 12. If necessary, the surgeon can inject additional BSS, lidocaine, viscoelastic, and/or healon mixture if necessary to balloon or inflate the target outflow region or re-inflate the already-ballooned target outflow region.

Step 13. If necessary, the surgeon can continue actuation of the injector to advance the shunt to its final position with the inflow and thereof in the anterior chamber and the outflow end thereof in the target outflow region. Surgeon can also verify that the inflow end of the shunt is positioned in anterior chamber.

Step 14. The surgeon can then retract the needle while the shunt is kept stationary in the final position (relative to the eye), for example, using a pusher rod behind the shunt proximal end inside the needle. Thereafter, the pusher rod can be retracted.

Step 15. If using an injector docking device, the surgeon can remove injector docking device.

Step 16. Optionally, the surgeon can massage the bleb away from cornea towards position of shunt (e.g., massage or lay the shunt down towards the deep layer of the target outflow region). The massaging can also move the shunt outflow position away from the conjunctival needle puncture and therefore reduce the chance for a subsequent leakage of aqueous humor). Thus, massaging the bleb can reposition the shunt outflow end to a desired position within the target outflow region.

Several variations of the above sequence are possible and can be used to deploy the shunt outflow end into any of the various spaces disclosed herein. Additionally, some embodiments of the procedure can be performed under guidance.

Further, some embodiments of the procedure, especially those using the injector docking device, can be performed in an office setting rather than a full sterility controlled or operating room setting, as long as all parts that touch the eye are fully sterile before use (e.g. sterilized disposables).

However, if the surgery is done in an operating room, an injector docking device may be unnecessary. In that case, the surgeon can approach freehand through the conjunctiva and sclera similar to the needle track they already do for the Ahmed or Baerveldt tube shunt placements. In accordance with some embodiments, the sleeve of the injector can be dimensioned to act as the longitudinal placement reference/stopper as it stops on the outside of the eye (conjunctiva over sclera). For example, such embodiments are discussed further below.

The ballooning of the eye can be done as a first step as described above or in another variation, the surgeon can place the shunt ab externo without the injector docking device and without ballooning. In such a procedure, after the shunt is released and the injector is removed, the outflow end of the shunt would protrude out of the eye through the conjunctiva while the inflow end of the shunt is positioned within the anterior chamber. The surgeon could then balloon the conjunctiva around the shunt outflow end until the conjunctiva and target outflow region would fully engulf the shunt outflow end such that the shunt is fully inside the newly formed bleb. At that point, the bleb can be pushed down and thereby laying the shunt flat against the sclera, as described above.

Figure 36A:
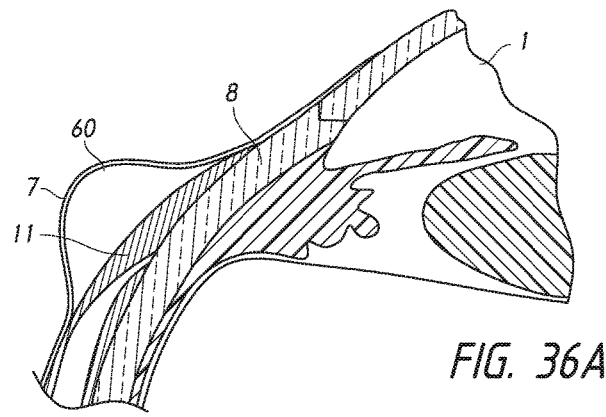
FIGS. 36A-38C illustrate additional procedures and outflow region locations for implanting an intraocular shunt into an eye using an injector and the injector docking device of FIG. 6, according to some embodiments.

Different target outflow regions can be ballooned, as noted above and as shown in FIGS. 36A-38C. For example, FIGS. 36A, 37A, and 38A illustrate examples of the target outflow regions in their ballooned states. FIG. 36A illustrates ballooning of the subconjunctival space 60, FIG. 37A illustrates ballooning of the intra-Tenon's adhesion space 11, and FIG. 38A illustrates ballooning of the suprascleral space 61. Following a procedure similar to that noted above, each of these spaces shown in FIGS. 36A-38A, as well as other spaces noted herein, can be inflated by an injection from a needle bevel is positioned adjacent to or within the space.

Figure 36B:
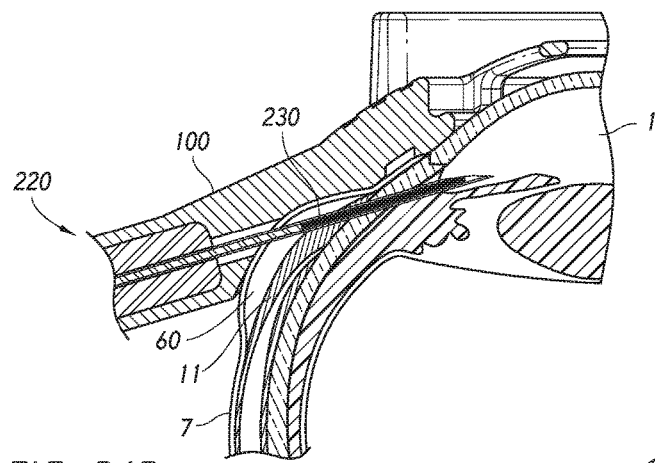
Figure 36C:
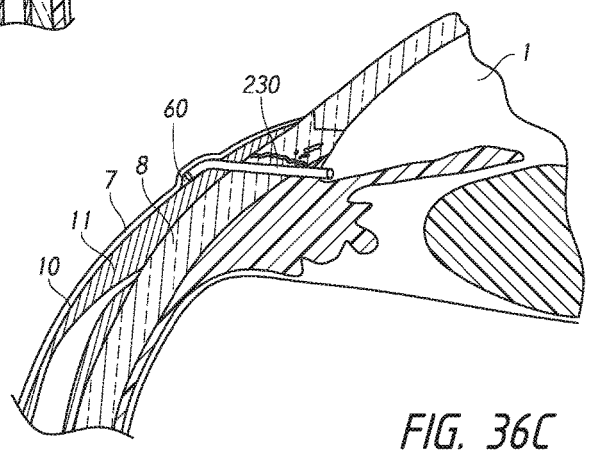
Figure 37A:
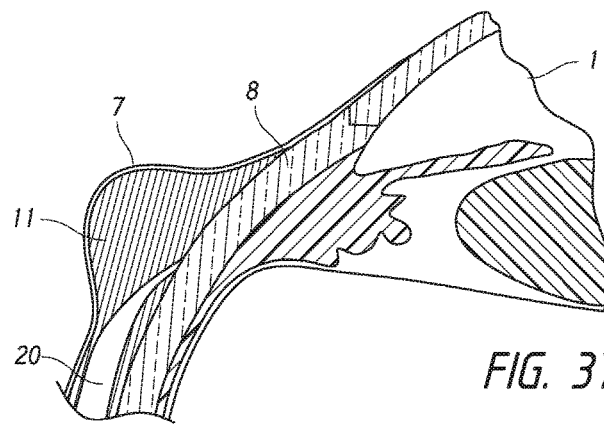
Figure 37B:
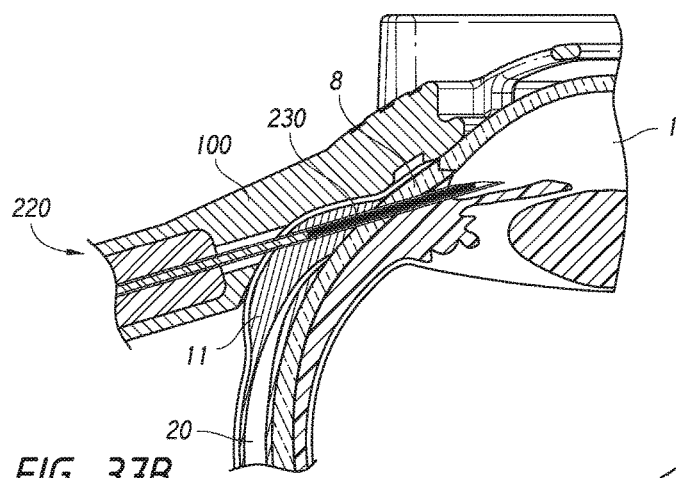
Figure 37C:
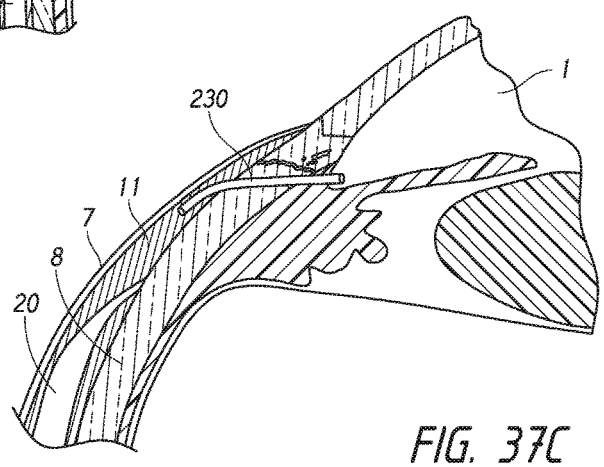
Figure 38A:
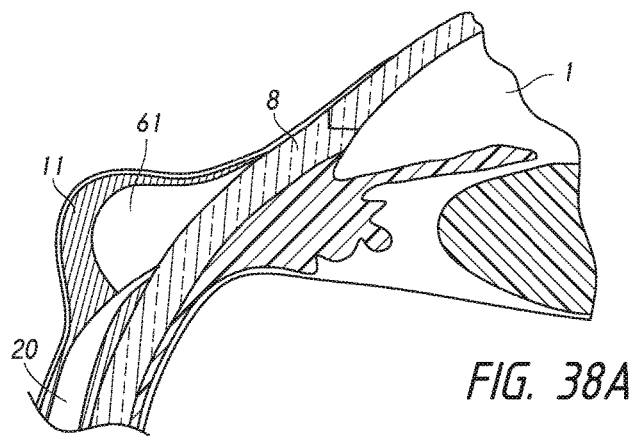
Figure 38B:
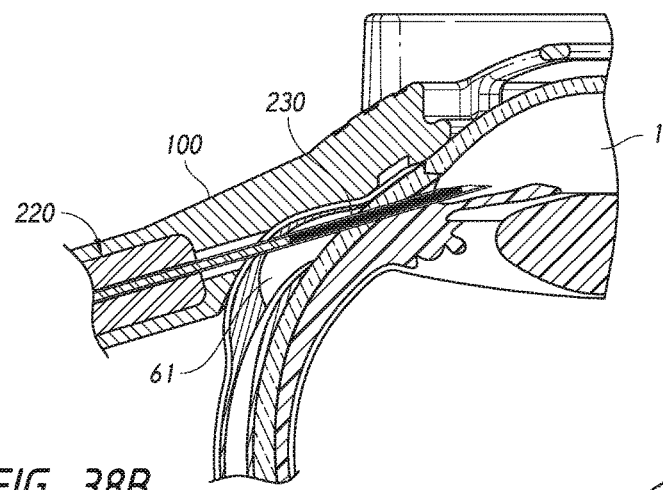
Figure 38C:
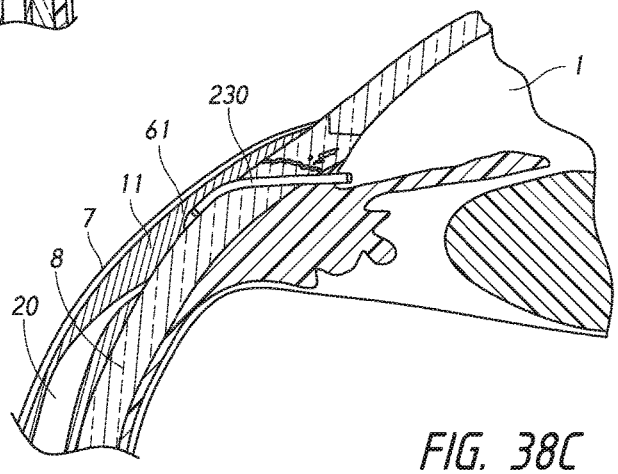

Thereafter, as illustrated in FIGS. 36B, 37B, and 38B, a docking device 100 can be positioned over a bleb created by the injection and inflation of the respective space. Once in position, an injector 220 can deliver and release a shunt 230 into the eye with a distal or inlet end of the shunt positioned in the anterior chamber and a proximal or outflow end of the shunt positioned in the respective space, which is the target outflow region. Finally, as shown in FIGS. 36C, 37C, and 38C, after manual and/or eventual diffusion and deflation of the bleb, the outflow end of the shunt can be positioned within the subconjunctival space 60, the intra-Tenon's adhesion space 11, and the suprascleral space 61, respectively. As noted herein, the target outflow region can include any of the several spaces disclosed herein other than those shown in FIGS. 36-38C. For example, some methods can involve forming a bleb in other target outflow regions or potential spaces in order to facilitate placement of the outflow end of the shunt thereat, including the subconjunctival space or over-Tenon's space (between Tenon's and conjunctiva), the suprascleral or sub-Tenon's space (between Tenon's and sclera), the intra-Tenon's space (between layers of Tenon's capsule, or in the intra-Tenon's adhesion space), the choroidal and suprachoroidal space, the intrascleral space (between layers of sclera), Schlemm's canal, the vitreous space, the episcleral vein, or the supraciliary space.

Shunt Materials

In some embodiments, the material selected for the shunt can be a gelatin or other similar material. For example, a gelatin used for making the shunt can be a gelatin Type B from bovine skin. A preferred gelatin is PB Leiner gelatin from bovine skin, Type B, 225 Bloom, USP. Another material that may be used in the making of the shunts is a gelatin Type A from porcine skin, also available from Sigma Chemical. Such gelatin is available is available from Sigma Chemical Company of St. Louis, Mo. under Code G-9382. Still other suitable gelatins include bovine bone gelatin, porcine bone gelatin and human-derived gelatins. In addition to gelatins, microfistula shunt may be made of hydroxypropyl methylcellulose (HPMC), collagen, polylactic acid, polyglycolic polyglycolic acid, hyaluronic acid and glycosaminoglycans.

If a gelatin shunt is used, the delivery of the shunt can be performed by wetting an inside the hollow shaft of the delivery device with a balanced salt solution (e.g., Dulbecco's Phosphate Buffered Saline), a steroid, or other drug prior to implantation. Such priming ensures that the shunt remains flexible before implantation. Further, an amount of a BSS, steroid, or other drug can be optionally injected through the hollow shaft, and in some embodiments, through the implant, into a target space to create a primed space for outflow and to deliver a drug, such as an antifibrotic to that new drainage space.

The shunt material can be cross-linked. For example, when a gelatin is used, cross-linking can increase the inter- and intramolecular binding of the gelatin substrate. Any means for cross-linking the gelatin may be used. In some embodiments, the formed gelatin shunts can be treated with a solution of a cross-linking agent such as, but not limited to, glutaraldehyde. Other suitable compounds for cross-linking include 1-ethyl-3-(3-dimethylaminopropyl)carbodiimide (EDC). Cross-linking by radiation, such as gamma or electron beam (e-beam) may be alternatively employed.

Drug-Eluting Shunts

In accordance with some embodiments, the shunt can comprise a drug or drug-eluting portion for drug delivery to one or more target locations within the eye. A drug-eluting portion can be provided in combination with any of the embodiments disclosed or taught herein. Therefore, some embodiments also relate to administering a pharmaceutical or drug via implantation of a shunt or plug, as discussed herein, to any of the variety of target locations discussed herein.

For example, any of the shunts or systems disclosed herein can be modified to incorporate a drug-eluting portion.

Thus, some embodiments provide a shunt that also operates as a drug delivery device inside the eye.

In some embodiments, at least a section of the shunt can comprise one or more drugs to provide a drug-eluting portion. In some embodiments, one or more drugs can be provided along the entire length of the shunt. However, in some embodiments, one or more drugs can be provided along less than the entire shunt or along only a portion of the shunt.

For example, a drug can be integrated into only one of the ends of the shunt to provide a single drug-eluting end which can be placed into the anterior chamber or location of lower pressure. Further, other than being formed along an end of the shunt, the drug-eluting portion can also be formed along an intermediate portion of the shunt. Accordingly, embodiments can provide a targeted drug release inside the anterior chamber, inside the sclera, and/or in the subconjunctival space or other target drainage location, depending on the location and configuration of the drug-eluting portion(s).

In some embodiments, the shunt can comprise multiple drug-eluting portions, which can each be formed to provide different dissolving times and/or have different drugs embedded therein. Accordingly, in some embodiments, two or more drugs can be delivered simultaneously on independent release timings.

For example, the shunt can comprise multiple dissolvable sections, which can each be formed to provide different dissolving times and/or have different drugs embedded therein.

Further, in some embodiments, the shunt can be impregnated or coated with one or more pharmaceutical and/or biological agents, e.g., drugs, biologics, pharmaceuticals, and/or other chemicals. The agent may be selected to regulate the body's response to the implantation of the shunt and the subsequent healing process. The agent can be carried by the shunt for delivery to the target location(s).

The impregnation and/or coating of the agent can be completely or partially along an interior or exterior portion of a shunt. In some embodiments, the pharmaceutical and/or biological agent may coat and/or impregnate an entire exterior of the shunt, an entire interior of the shunt, or both. Alternatively, the pharmaceutical and/or biological agent may coat and/or impregnate a portion of an exterior of the shunt, a portion of an interior of the shunt, or both.

In some embodiments in which the agent is impregnated into the shunt, the shunt itself can be partially or completely dissolvable. By including the biologics, pharmaceuticals, drugs, or other chemicals in the liquid gelatin, the formed shunt will be impregnated with the biologics, pharmaceuticals, drugs, or other chemicals.

As noted above, whether the agent is impregnated into and/or coated onto the body of the shunt, the drug-eluting dissolvable portion(s) can extend along the entire length or only a portion of the length of the shunt.

Further, in some embodiments, a time-release or controlled-release drug can be provided by means of an impregnated portion or coating to provide a desired dissolution rate. Such drug-eluting portion(s) of the shunt can provide a drug delivery, even without aqueous flow.

For example, some methods can comprise treatment with a drug or pharmaceutical, such as by implanting an intraocular shunt that has been coated and/or impregnated with a pharmaceutical and/or biological agent, by treating the eye topically with a pharmaceutical and/or biological agent, and/or by injecting a pharmaceutical and/or biological agent into the anterior chamber and/or a target outflow region, including any target outflow regions discussed or referenced herein, prior to or after releasing a shunt from the device. Suitable agents may include, for example, any of those disclosed in the following U.S. Pat. Nos. 8,785,394; 8,062,657; 7,799,336; 7,790,183; 7,033,605; 6,719,991; 6,558,686; 6,162,487; 5,902,283; 5,853,745; and 5,624,704; and U.S. Patent Publication No. 2008/0108933; the content of each of these references is incorporated by reference herein its entirety. Further examples of suitable agents include anti-mitolic pharmaceuticals such as Mitomycin-C or 5-Fluorouracil, anti-VEGF (such as Lucentis, Macugen, Avastin, VEGF or steroids), anti-coagulants, anti-metabolites, angiogenesis inhibitors, steroids, anti-inflammatories, antibiotics, brimonidine, timolol, prostaglandin analogs (such as travoprost, latanoprost, and tafluprost), prostamides (such as bimatoprost), cyclosporin, pilocarpine, corticosteroids and other steroid derivatives (such as hydrocortisone, dexamethasone, beclomethasone dipropionate, triamcinolone, triamcinolone acetate, cortisol benzoate), or other agents for treating conditions of the eye, such as glaucoma, dry eye, allergy, or conjunctivitis, to name a few.

Aspects related to embodiments of drug delivery shunts are discussed in copending U.S. Application Publication No. 2012/0197175, filed on Dec. 8, 2008, U.S. Application Publication No. 2014/0236066, filed on Feb. 19, 2013, the entireties of each of which is incorporated herein by reference.

A drug-eluting shunt implementing any of the features discussed or referenced herein can be implanted into any area of the eye to achieve drainage into any of the target areas discussed or referenced or referenced herein. For example, the shunt can be implanted into the suprachoroidal space (with one end in the anterior chamber and the other end in the suprachoroidal space or with the entire shunt being completely suprachoroidal) with the ability to deliver drugs at either or both ends or along an intermediate portion thereof. Some methods can be implemented such that multiple shunts (with the same or different drugs and with the same or different release timings) can be implanted in different places (e.g., the subconjunctival space, the suprachoroidal space, the anterior chamber, etc.). Other methods and procedures can be performed to incorporate any of the shunts discussed or referenced herein. Further, additional procedures for delivering drug-eluting plugs or shunts within the eye can be performed using one or more of the systems or devices disclosed herein. For example, the present disclosure can be used in combination with any of the shunts, plugs, or methods disclosed in U.S. Patent Application No. 62/344,899, filed Jun. 2, 2016, the entirety of which in incorporated herein by reference.

As used herein, "controlled release" or "time-release" may refer to the release of an agent such as a drug from a composition or dosage form in which the agent is released according to a desired profile over an extended period of time. For example, such release can effect delivery of an active over an extended period of time, defined herein as being between about 60 minutes and about 2, 4, 6, 8 or even 12 hours. Controlled release profiles may include, for example, sustained release, prolonged release, pulsatile release, and delayed release profiles. Controlled release may also be defined functionally as the release of over 80 to 90 percent (%) of the active ingredient after about 60 minutes and about 2, 4, 6 or even 8 hours. Controlled release may also be defined as making the active ingredient available to the patient or subject regardless of uptake, as some actives may never be absorbed by the animal.

In contrast to immediate release compositions, controlled release compositions may permit delivery of an agent to a subject over an extended period of time according to a predetermined profile. Such release rates can provide therapeutically effective levels of agent for an extended period of time and thereby provide a longer period of pharmacologic or diagnostic response as compared to conventional rapid release dosage forms. Such longer periods of response may provide many benefits that are not achieved with the corresponding short acting, immediate release preparations.

The foregoing description is provided to enable a person skilled in the art to practice the various configurations described herein. While the subject technology has been particularly described with reference to the various figures and configurations, it should be understood that these are for illustration purposes only and should not be taken as limiting the scope of the subject technology.

There may be many other ways to implement the subject technology. Various functions and elements described herein may be partitioned differently from those shown without departing from the scope of the subject technology. Various modifications to these configurations will be readily apparent to those skilled in the art, and generic principles defined herein may be applied to other configurations. Thus, many changes and modifications may be made to the subject technology, by one having ordinary skill in the art, without departing from the scope of the subject technology.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method Clauses present elements of the various steps in a sample order, and are not meant to be limited to the specific order or hierarchy presented.

Terms such as "top," "bottom," "front," "rear" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Furthermore, to the extent that the term "include," "have," or the like is used in the description or the claims, such term is intended to be inclusive in a manner similar to the term "comprise" as "comprise" is interpreted when employed as a transitional word in a claim.

The word "exemplary" is used herein to mean "serving as an example, instance, or illustration." Any embodiment described herein as "exemplary" is not necessarily to be construed as preferred or advantageous over other embodiments.

A reference to an element in the singular is not intended to mean "one and only one" unless specifically stated, but rather "one or more." Pronouns in the masculine (e.g., his) include the feminine and neuter gender (e.g., her and its) and vice versa. The term "some" refers to one or more. Underlined and/or italicized headings and subheadings are used for convenience only, do not limit the subject technology, and are not referred to in connection with the interpretation of the description of the subject technology. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

While certain aspects and embodiments of the inventions have been described, these have been presented by way of example only, and are not intended to limit the scope of the inventions. Indeed, the novel methods and systems described herein may be embodied in a variety of other forms without departing from the spirit thereof. The accompanying claims and their equivalents are intended to cover such forms or modifications as would fall within the scope and spirit of the inventions.

What is claimed is:

1. An injector docking device for placing an intraocular shunt into an eye, the injector docking device comprising:
    a body comprising an elongate eye-contacting component having a pair of prongs comprising at least one eye-contacting portion, the pair of prongs having proximal ends spaced apart by a gap and separate distal ends; and
    a needle support component coupled to the proximal ends of the pair of prongs, the needle support component comprising a needle port extending to the gap of the pair of prongs, the needle port defining a needle axis extending in a direction of the at least one eye-contacting portion, wherein the distal ends of the pair of prongs diverge to increase a size of the gap in a direction away from the needle support component.

2. The injector docking device of claim 1, wherein the needle support component comprises a shaft having the needle port extending therethrough, the needle port comprising a lumen within the shaft.

3. The injector docking device of claim 1, wherein the eye-contacting portion comprises an adhesion component for coupling the injector docking device to the eye.

4. The injector docking device of claim 3, wherein the adhesion component comprises a plurality of spikes.

5. The injector docking device of claim 1, wherein the eye-contacting portion comprises an arcuate eye-contacting surface for alignment of the injector docking device relative to an indicium of the eye and alignment of the needle axis to the eye.

6. The injector docking device of claim 1, wherein each of the pair of prongs taper toward a tip portion configured to contact the eye.

7. The injector docking device of claim 1, comprising a bleb pocket adjacent to the needle port, the bleb pocket comprising a concavity extending into the body from the eye-contacting component toward an upper portion of the body.

8. A device for placing an intraocular shunt into an eye, the device comprising:
    an injector docking device comprising: an annular eye-contacting component having a gap; and a needle support component coupled to the annular eye-contacting component, the needle support component comprising a needle port adjacent to the gap, the needle port defining a needle axis extending through the gap toward the annular eye-contacting component; and
    an inserter comprising a sleeve positionable within the needle port so that an outer surface of the sleeve is opposite to an inner surface of the needle port, wherein the sleeve is configured to move relative to the injector docking device along the needle axis.

9. The injector docking device of claim 8, comprising a bleb pocket adjacent to the needle port, the bleb pocket comprising a concavity extending away from the eye-contacting component.

10. The device of claim 8, wherein the needle port comprising a lumen extending through the needle support component.

11. The device of claim 8, wherein the sleeve and the injector docking device are rotatable relative to each other around the needle axis.

12. The device of claim 8, wherein the sleeve and the injector docking device comprise a cross-sectional profile that is transverse relative to the needle axis, and wherein the cross-sectional profile of the sleeve and the injector docking device are configured to resist rotation relative to each other around the needle axis.

13. The device of claim 12, wherein cross-sectional profile of any of the sleeve and the injector docking device comprises a polygonal shape configured to resist rotation of the sleeve and the injector docking relative to each other.

14. The device of claim 12, wherein any of the sleeve and the injector docking device comprise a ridge or a groove configured to mate with the other of the sleeve and the injector docking device.

15. An injector docking device for placing an intraocular shunt into an eye, the injector docking device comprising:
an elongate eye-contacting component having a pair of prongs comprising at least one eye-contacting portion, the pair of prongs having proximal ends spaced apart by a gap and distal end portions that each comprise an angled eye-contacting surface;
a needle support component coupled to the proximal ends of the pair of prongs, the needle support component comprising a needle port extending to the gap of the pair of prongs, the needle port defining a needle axis extending in a direction of the at least one eye-contacting portion; and
a bleb pocket adjacent to the needle port, the bleb pocket comprising a concavity extending away from the eye-contacting component.

16. The injector docking device of claim 15, wherein the needle port comprising a lumen extending through the needle support component.

17. The injector docking device of claim 15, wherein each of the pair of prongs taper toward a tip portion configured to contact the eye.

18. The injector docking device of claim 15, wherein the distal end portions of the pair of prongs diverge to increase a size of the gap in a direction away from the needle support component.

* * * * *